United States Patent
Messeguer Peypoch et al.

(10) Patent No.: US 9,040,701 B2
(45) Date of Patent: May 26, 2015

(54) APAF-1 INHIBITOR COMPOUNDS

(75) Inventors: Ángel Messeguer Peypoch, Barcelona (ES); Alejandra Moure Fernández, Barcelona (ES); Daniel González Pinacho, Barcelona (ES); Isabel Masip Masip, Barcelona (ES); Enrique Pérez Payá, Barcelona (ES); Natividad García Villar, Barcelona (ES); Ester Monlleó Mas, Barcelona (ES); Juanlo Catena Ruiz, Barcelona (ES)

(73) Assignee: LABORATORIOS SALVAT, S.A., Barcelona (ES)

( * ) Notice: Subject to any disclaimer, the term of this patent is extended or adjusted under 35 U.S.C. 154(b) by 0 days.

(21) Appl. No.: 13/387,240

(22) PCT Filed: Jul. 29, 2010

(86) PCT No.: PCT/ES2010/000349
§ 371 (c)(1),
(2), (4) Date: Jan. 26, 2012

(87) PCT Pub. No.: WO2011/012746
PCT Pub. Date: Feb. 3, 2011

(65) Prior Publication Data
US 2012/0122868 A1    May 17, 2012

(30) Foreign Application Priority Data
Jul. 30, 2009 (ES) .................................. 200901757

(51) Int. Cl.
| | | |
|---|---|---|
| C07D 241/06 | (2006.01) | |
| C07D 241/08 | (2006.01) | |
| C07D 401/12 | (2006.01) | |
| C07D 403/12 | (2006.01) | |
| C07D 403/14 | (2006.01) | |
| C07D 405/12 | (2006.01) | |
| C07D 405/14 | (2006.01) | |
| C07D 409/12 | (2006.01) | |
| C07D 409/14 | (2006.01) | |

(52) U.S. Cl.
CPC ............ *C07D 241/08* (2013.01); *C07D 401/12* (2013.01); *C07D 403/12* (2013.01); *C07D 403/14* (2013.01); *C07D 405/12* (2013.01); *C07D 405/14* (2013.01); *C07D 409/12* (2013.01); *C07D 409/14* (2013.01)

(58) Field of Classification Search
CPC .................................................... C07D 241/08
USPC ............... 514/235.8, 255.02, 253.01, 253.09, 514/254.01, 252.13; 544/385, 372, 379
See application file for complete search history.

(56) References Cited

U.S. PATENT DOCUMENTS

| | | | | |
|---|---|---|---|---|
| 3,560,503 A | * | 2/1971 | Anand et al. ................... | 544/279 |
| 5,281,585 A | * | 1/1994 | Duggan et al. .................. | 514/79 |

FOREIGN PATENT DOCUMENTS

| | | |
|---|---|---|
| EP | 0493813 A1 | 7/1992 |
| EP | 0538882 A1 | 4/1993 |
| EP | 1698703 A1 | 9/2006 |
| GB | 1284582 A | 8/1972 |
| JP | 4234375 A | 8/1992 |
| JP | 5117246 A | 8/1992 |
| JP | 2006502418 A | 1/2006 |
| WO | WO9600391 * | 1/1996 |
| WO | 2004030522 A2 | 4/2004 |
| WO | 2005052177 A1 | 9/2005 |
| WO | 2007060524 A1 | 5/2007 |
| WO | 2008009758 A1 | 1/2008 |

OTHER PUBLICATIONS

Bali, S., et al. "Corneal Graft Rejection: A Review of Literature and Recent Advances." WebmedCentral.com. (2010), pp. 1-9.*
Patani, G.A., et al. "Bioisosterism: A Rational Approach in Drug Design." Chem. Rev. (1996), vol. 96, pp. 3147-3176.*
Mayo Clinic. "Alzheimer's treatments: What's on the horizon?" © Mar. 2013.*
Mitsos, C. "Isosteres in Medicinal Chemistry." © 2006, pp. 1-7.*
G Malet, et al.; "Small molecule inhibitors of Apaf-1-related caspase-3/-9 activation that control mitochrondrial-dependent apoptosis," Cell Death and Differentiation, 2006, pp. 1523-1532, vol. 13.
Base De Datos Registry (CAS) EN STN, Recuperado on Line el Dia Nov. 5, 2010, Feb. 17, 2008, RN 1003895-61-1; RN 1003895-57-5; RN 1003895-55-3; RN 1003895-53-1.
Göktalay, Gökhan, et al.; "Glycyl-glutamine inhibits nicotine conditioned place preference and withdrawal," European Journal of Pharmacology, 2006, pp. 95-102, vol. 530.
Saxena, Ranjna, et al.; "Studies in Potential Filaricides. 5. 3-Ethyl-8-methyl-1,3,8-triazabicyclo[4.4.0]decan-2-one, a New Antifilarial Agent," Journal of Medicinal Chemistry, 1971, pp. 929-930, vol. 14.
Supplemental European Search Report, Jan. 21, 2013.

* cited by examiner

*Primary Examiner* — Noble Jarrell
*Assistant Examiner* — John S Kenyon
(74) *Attorney, Agent, or Firm* — Tristan A. Fuierer; Moore & Van Allen, PLLC

(57) ABSTRACT

Derivatives of 2,5-piperazinedione of formula (I) are apoptotic peptidase activating factor 1 (Apaf-1) inhibitors, therefore they are useful as active pharmaceutical ingredients for the prophylaxis and/or treatment of a pathological and/or physiological condition associated with an increase of apoptosis.

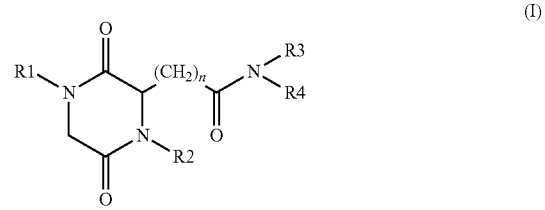

(I)

13 Claims, No Drawings

APAF-1 INHIBITOR COMPOUNDS

CROSS-REFERENCE TO RELATED APPLICATIONS

This application is filed under the provisions of 35 U.S.C. §371 and claims the priority of International Patent Application No. PCT/ES2010/000349 filed on 29 Jul. 2010 entitled "APAF-1 Inhibitor Compounds" in the name of Ángel MES-SEGUER PEYPOCH, et al., which claims priority of Spanish Patent Application No. p200901757 filed on 30 Jul. 2009, both of which are hereby incorporated by reference herein in their entirety.

The present invention relates to compounds for the prophylaxis and/or treatment of disorders caused by apoptotic cell death or for the prevention of degenerative processes caused by apoptotic cell death.

STATE OF THE ART

Apoptosis or programmed cell death is a complex physiological phenomenon involved in the maintenance of cell homeostasis. Apoptosis is regulated by various cell control mechanisms due to its key role in health maintenance. Many pathologies are based on apoptosis dysfunction. Therefore, an excess of apoptotic cell death can affect tissue functionality (e.g. cardiomyocyte death in the cases of myocardial infarction), whereas an excessively inhibited apoptosis entails uncontrolled cell survival (e.g. neoplastic processes). The cell components regulating apoptosis are in constant dynamic equilibrium in a healthy cell. There are at least two well characterized activation pathways for the apoptotic caspase cascade. One of them, the extrinsic pathway, is activated by extracellular signaling and requires the participation of specific membrane receptors. The intrinsic pathway corresponds to cellular stress, toxic agents, radiation, oxidizing agents, $Ca^{2+}$ overloading, DNA injury; it is activated in response to oncogenes and involves mitochondrial destabilization. In some pathophysiological conditions (for example, anoxia in cells of organs to be transplanted, treatment with toxic substances), apoptosis increases and an excessive number of cells die, crippling the functionality of the affected tissue and compromising its survival in some cases.

The molecular apoptosis induction mechanisms entail the activation of proteins with protease activity called caspases which are also known as effectors of apoptosis. The formation of a molecular complex called apoptosome is necessary to enable activating the caspases. Apoptosome is formed by cytochrome c, pro-caspase-9 and the apoptotic peptidase activating factor 1 (Apaf-1). It has been demonstrated that Apaf-1 inhibition inhibits the formation of the apoptosome complex and that it causes an apoptosis inhibition (measured through caspase 3 activation). In cell assays in which apoptosis is induced by means of hypoxia (reducing the air oxygen concentration) or by means of chemical compounds, an increase of cell survival has been observed when the latter have been previously treated with apoptosis inhibitors.

Likewise, during the process of removing and transplanting an organ, its cells are subjected to a hypoxia condition which can lead to cell death compromising the organ viability and functionality. Therefore, for example, only 70% of all the corneas donated for transplant are suitable to be implanted. This is due to the fact that apoptotic cell death occurs during cornea storage. A similar situation occurs during kidney and heart transplants. There are solutions on the market for transporting organs exclusively providing buffered and sterile environments but they do not contain any active molecule which prevents apoptotic cell death.

The study of the mechanisms involved in apoptosis has allowed identifying different potential pharmacological targets. Therefore, inhibitors acting at different levels of the apoptotic cascade such as transcription factors, kinases, regulators of mitochondrial membrane permeabilization and inhibitors of the caspase family have been designed.

Since the formation of apoptosome is a key step in the apoptotic cascade and the subsequent activation of the caspases, the inhibition of Apaf-1 activation can have a greater impact on apoptosis inhibition than other pharmacological targets studied. There are indications in the scientific literature about the therapeutic implications of Apaf-1 inhibition. Therefore the transduction of an Apaf-1 dominant negative by means of an adenovirus in an animal model of Parkinson's was more effective than the transduction of a caspase-1 dominant negative by means of an adenovirus.

Document WO2007060524 describes derivative compounds of [1,4]diazepan-2,5-dione of the following formula as apoptosis inhibitors.

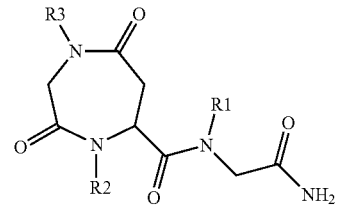

Document WO2008009758 describes the compounds of the following formula as UBC13-UEV interaction inhibitors which can be used in the preparation of pharmaceutical compositions for anti-tumor therapy or for the treatment and/or prophylaxis of diseases associated with metabolic pathways involving the enzyme UBC13, metabolic pathways involving transcription factor NF-kB, or pathways involving PCNA or RAD6. Although they can be considered as structurally similar to those of the present invention, they have a different use.

$$R-(CR_1R_2)_q-CO-N(R_3)-C(R_4R_5)-CO-NH_2$$

It is therefore desirable to provide new Apaf-1 inhibitor compounds.

DESCRIPTION OF THE INVENTION

The present invention provides new derivative compounds of 2,5-piperazinedione of formula (I) having APAF-1 inhibiting activity.

Therefore, a first aspect of the invention relates to compounds of formula (I)

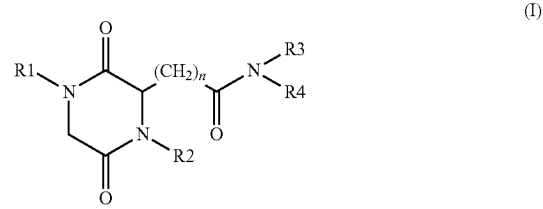

and pharmaceutically acceptable salts thereof, wherein:
R1 and R2 are independently selected from —H, —$C_{1-5}$ alkyl, —$C_{2-5}$ alkenyl, —$(CH_2)_{0-3}$-cycloalkyl, —$(CH_2)_{1-3}$- heterocycle, —(CH$_2$)$_{0-3}$-aryl, —(CH$_2$)$_{0-3}$-heteroaryl, —(CH$_2$)$_{1-2}$—CH(aryl)$_2$, —(CH$_2$)$_{1-2}$—CH(aryl)(heteroaryl) and —(CH$_2$)$_{1-2}$—CH(heteroaryl)$_2$, R3 is selected from —H, —C$_{1-5}$ alkyl, —C$_{2-5}$ alkenyl, —(CH$_2$)$_{0-3}$-cycloalkyl, —(CH$_2$)$_{1-3}$-heterocycle, —(CH$_2$)$_{1-3}$-aryl, —(CH$_2$)$_{1-3}$-heteroaryl, —(CH$_2$)$_{1-3}$—CONR5R6, —(CH$_2$)$_{1-2}$—CH(aryl)$_2$, —(CH$_2$)$_{1-2}$—CH(aryl)(heteroaryl) and —(CH$_2$)$_{1-2}$—CH(heteroaryl)$_2$, R4 is selected from —H, —C$_{1-5}$ alkyl, —(CHR7)$_{1-3}$—CO—NR5R6, —(CHR7)$_{1-3}$—CO—OR5, —(CH$_2$)$_{1-3}$—NR5R6, —(CH$_2$)$_{1-3}$—CO[NCHR7CO]$_m$NH$_2$ and —(CH$_2$)$_{1-3}$—CO[NCHR7CO]$_m$OR5, n is an integer selected from 1 and 2;

m is an integer selected from 1, 2 and 3;

R5 and R6 are independently selected from —H, —C$_{1-5}$ alkyl and —(CH$_2$)$_{0-3}$-aryl, R7 is selected from —H, —C$_{1-5}$ alkyl, —(CH$_2$)$_{1-3}$-aryl and —(CH$_2$)$_{1-3}$-heteroaryl, such that when m is greater than 1 the R7 substituents can be equal to or different from one another, wherein the C$_{1-5}$ alkyl, C$_{2-5}$ alkenyl, cycloalkyl and heterocycle groups can be optionally substituted with one or several substituents selected independently from halogen, OR5, OCF$_3$, SH, SR5, NR5R6, NHCOR5; COOH, COORS, OCOR5, aryl and heteroaryl, wherein the aryl and heteroaryl groups can be optionally substituted with one or several substituents selected independently from halogen, CF3, OR5, OCF$_3$, SH, SR5, NH$_2$, NHCOR5; NO$_2$, CN, COR5, COOR5, OCOR5, CONR5R6, —(CH$_2$)$_{0-3}$NR5R6, SO$_2$NH$_2$, NHSO$_2$CH$_3$, C$_{1-5}$ alkyl, aryl and heteroaryl, wherein the heterocycle and heteroaryl groups can be optionally substituted on a secondary nitrogen atom with C$_{1-5}$ alkyl, cycloalkyl or —(CH$_2$)$_{0-3}$-aryl, on the condition that when R2 is 2-(4-fluorophenyl)ethyl, R4 is —CH$_2$—CO—NH$_2$ and n is 1, then:

if R1 is 2-(4-fluorophenyl)ethyl, R3 is not 2-(4-methoxyphenyl)ethyl, 2-(2-pyridyl)ethyl or 2-(2,4-dichlorophenyl)ethyl, and if R1 is 2-(2,4-dichlorophenyl)ethyl, R3 is not 2-(4-methoxyphenyl)ethyl or 2-(2-pyridyl)ethyl.

In a particular embodiment of the invention, R1 is —C$_{1-5}$ alkyl or —(CH$_2$)$_{0-3}$-aryl.

In another particular embodiment of the invention, R2 is —C$_{1-5}$ alkyl, —(CH$_2$)$_{0-3}$-aryl, —(CH$_2$)$_{0-3}$-heteroaryl or —(CH$_2$)$_{1-2}$—CH(aryl)$_2$.

In another particular embodiment of the invention, R3 is —H, —C$_{1-5}$ alkyl, —(CH$_2$)$_{1-3}$-heterocycle, —(CH$_2$)$_{1-3}$-aryl or —(CH$_2$)$_{1-3}$-heteroaryl.

In another particular embodiment of the invention, R4 is —H, —(CHR7)$_{1-3}$—CO—NR5R6, —(CHR7)$_{1-3}$—CO—OR5 or —(CH$_2$)$_{1-3}$—CO[NCHR7CO]$_m$NH$_2$.

In another particular embodiment of the invention, n is 1.

In another particular embodiment of the invention, m is 1.

In another particular embodiment of the invention, R5 is —H or —C$_{1-5}$ alkyl.

In another particular embodiment of the invention, R6 is —H.

In another particular embodiment of the invention, R7 is —H, —C$_{1-5}$ alkyl, —(CH$_2$)$_{1-3}$-aryl or —(CH$_2$)$_{1-3}$-heteroaryl.

A second aspect of the present invention relates to a compound of formula (I), or a pharmaceutically acceptable salt thereof for use as an active pharmaceutical ingredient, particularly for use in the prophylaxis and/or treatment of a pathological and/or physiological condition associated with an increase of apoptosis, wherein the pathological and/or physiological condition associated with an increase of apoptosis is selected from organ or cell preservation, particularly transplant or conservation; cytotoxicity prevention, particularly cytotoxicity mediated by chemicals, by physical agents such as radiation, acoustic trauma, burns, or by biological agents such as hepatitis virus infection; pathologies due to hypoxia conditions, such as heart attack or cerebral infarction; eye pathologies, such as injuries caused by eye surgery, age-related macular degeneration, diabetic retinopathy, retinitis pigmentosa or glaucoma; neurodegenerative diseases, such as Alzheimer's, Huntington's, Parkinson's or amyotrophic multiple sclerosis; diabetes, particularly preservation of islets of Langerhans or diabetes-associated cytotoxicity such as, for example, nephrotoxicity; osteoarthritis; arthritis; inflammation or immunodeficiencies, such as AIDS-associated CD4$^+$ T lymphocyte depletion.

Another aspect of the present invention relates to the use of a compound of formula (I) or of a pharmaceutically acceptable salt thereof for the manufacture of a medicament intended for the prophylaxis and/or treatment of a pathological and/or physiological condition associated with an increase of apoptosis, particularly one of the aforementioned conditions.

Another aspect of the present invention relates to a method of prophylaxis and/or treatment of an individual or organ suffering or susceptible to suffering a pathological and/or physiological condition associated with an increase of apoptosis, particularly one of the aforementioned conditions, comprising the administration of a therapeutically effective amount of a compound of formula (I) or of a pharmaceutically acceptable salt thereof to said individual or organ together with sufficient amounts of pharmaceutically acceptable excipients.

The compounds of formula (I) and the pharmaceutically acceptable salts thereof, particularly the compounds of formula (I) described as examples or as intermediates are preferred.

The compounds of the present invention can be used alone or in combination with one or more compounds which are useful for the prophylaxis and/or treatment of a pathological and/or physiological condition associated with an increase of apoptosis, such as organ or cell preservation, particularly transplant or conservation; cytotoxicity prevention, particularly cytotoxicity mediated by chemicals, by physical agents such as radiation, acoustic trauma, burns, or by biological agents such as hepatitis virus infection; pathologies due to hypoxia conditions, such as heart attack or cerebral infarction; eye pathologies, such as injuries caused by eye surgery, age-related macular degeneration, diabetic retinopathy, retinitis pigmentosa or glaucoma; neurodegenerative diseases, such as Alzheimer's, Huntington's, Parkinson's or amyotrophic multiple sclerosis; diabetes, particularly preservation of islets of Langerhans or diabetes-associated cytotoxicity such as, for example, nephrotoxicity; osteoarthritis; arthritis; inflammation or immunodeficiencies, such as AIDS-associated CD4$^+$ T lymphocyte depletion.

The term "C$_{1-5}$ alkyl", alone or in combination, means a linear- or branched-chain alkyl group having 1 to 5 carbon atoms.

The term "C$_{2-5}$ alkenyl", alone or in combination, means a linear- or branched-chain group having 2 to 5 carbon atoms and having one or more unsaturated bonds.

The term "cycloalkyl", alone or in combination, refers to a stable monocyclic radical of 3 to 7 members, which is saturated or partially saturated, and which only consists of carbon and hydrogen atoms. Examples of cycloalkyl are the following: cyclopropyl, cyclopentyl, cyclohexyl, 1-cyclohexenyl, cycloheptyl.

The term "heterocycle", alone or in combination, means a saturated or partially unsaturated heterocycle of 5 to 10 links, containing one or several heteroatoms chosen from nitrogen, oxygen and sulfur. For the purposes of this invention, the heterocycle can be a monocyclic or bicyclic ring system which can include condensed ring systems. Examples of heterocycle groups are tetrahydrofuranyl (THF), dihydrofuranyl, dioxanyl, morpholyl, piperazinyl, piperidinyl, 1,3-dioxolanyl, imidazolidinyl, imidazolinyl, pyrrolidyl, pyrrolidinyl, tetrahydropyranyl, dihydropyranyl, and the like.

The term "aryl", alone or in combination, refers to a mono- or polycyclic aromatic ring system containing carbon ring atoms. The preferred aryls are monocyclic or bicyclic aromatic ring systems of 5-10 members, such as phenyl or naphthyl having optionally one or several substituents, preferably from one to three selected independently from halogen, $CF_3$, OH, ORS, $OCF_3$, SH, SRS, $NH_2$, NHCOR5; $NO_2$, CN, COR5, COOR5, OCOR5, CONR5R6, —$(CH_2)_{0-3}$NR5R6, $SO_2NH_2$, $NHSO_2CH3$, $C_{1-5}$ alkyl, aryl and heteroaryl.

The term "heteroaryl", alone or in combination, refers to an aromatic or partially aromatic heterocycle containing at least one ring heteroatom selected from O, S and N. Heteroaryls thus includes heteroaryls condensed to other classes of rings, such as aryls, cycloalkyls and heterocycles which are not aromatic. Examples of heteroaryl groups include: pyrrolyl, isoxazolyl, isothiazolyl, pyrazolyl, pyridyl, oxazolyl, thiazolyl, imidazolyl, triazolyl, furyl, thienyl, pyrimidyl, benzisoxazolyl, benzoxazolyl, benzothiazolyl, dihydrobenzofuranyl, indolinyl, pyridazinyl, indazolyl, isoindolyl, dihydrobenzothienyl, indolizinyl, quinazolinyl, naphthyridinyl, isobenzylfuranyl, benzimidazolyl, benzofuranyl, benzothienyl, quinolyl, indolyl, isoquinolyl, dibenzofuranyl, benzothiophenyl, tetrahydrobenzothiophenyl and the like.

The expression "optionally substituted with one or several substituents" means that a group can be unsubstituted or substituted with one or several substituents, preferably with 1, 2, 3 or 4 substituents, provided that said group has 1, 2, 3 or 4 positions susceptible to be substituted.

The term "pharmaceutically acceptable salts" means those salts which conserve the efficiency and the biological properties of the free bases or free acids and which do not cause discomfort in a biological sense or in any other sense.

According to the invention, the compounds of formula (I) and their pharmaceutically acceptable salts are useful for the prophylaxis and/or treatment of a pathological and/or physiological condition associated with an increase of apoptosis by means of their APAF-1 inhibiting activity.

Unless defined otherwise, all the technical and scientific terms used herein have the same meaning as those commonly understood by a person skilled in the field of the invention. Methods and materials which are similar or equivalent to those described herein can be used in practicing the present invention. Throughout the description and claims the word "comprises" and its variants do not aim to exclude other technical features, additives, components, steps or stereoisomers of the compounds involved. For the persons skilled in the art, other objects, advantages and features of the invention will be inferred partially from the description and partially from practicing the invention.

The compounds of formula (I) can be prepared following different methods known by any person skilled in the field of organic synthesis, particularly through the general processes shown in the following schemes. The starting materials for the preparative methods are commercially available or they can be prepared by means of methods of the literature. Unless indicated otherwise, the meaning of groups R1, R2, R3, R4, R5, R6 and R7 are those described in the general formula (I).

The compounds of formula (I) can be obtained from the methods and schemes described below:

Scheme 1

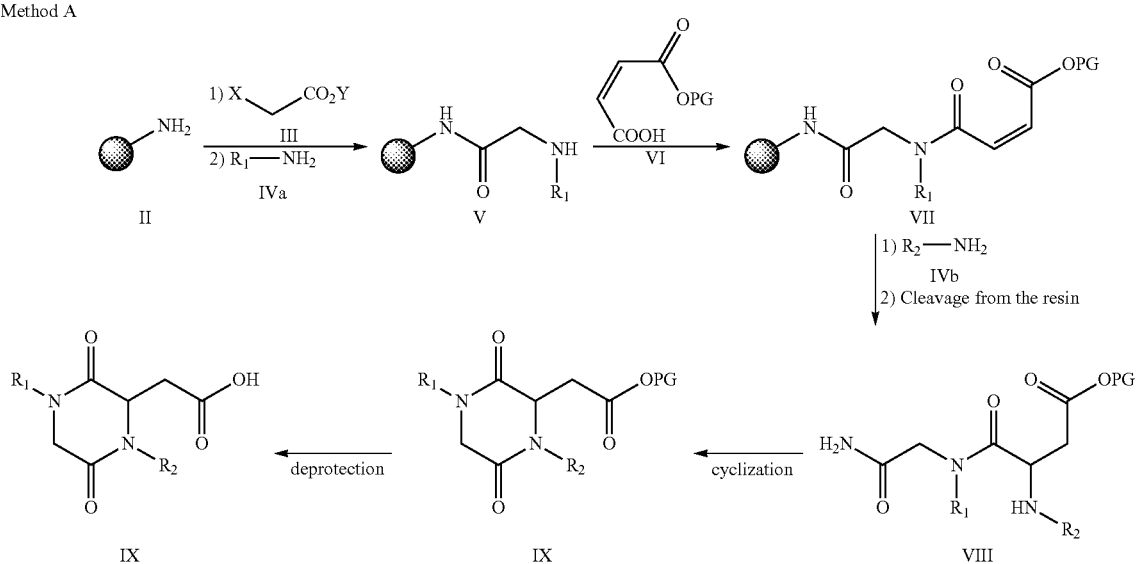

According to Method A, once the fluorenemethyloxycarbonyl group is deprotected, the amine II bound to the solid support is acylated with an acylating agent III, wherein X represents a leaving group, for example a halogen and Y represents OH or halogen. When Y represents a halogen, for example chloroacetyl chloride, the reaction can be performed in the presence of a base such as triethylamine. When Y represents —OH, for example bromoacetic acid, the reaction can be carried out in the presence of a suitable coupling agent, for example N,N'-diisopropylcarbodiimide. In both cases the reaction can be performed in an inert solvent which is capable of swelling the resin, such as N,N-dimethylformamide or methylene chloride and at room temperature or under microwave irradiation to minimize the reaction time. Then, the amine IVa is coupled using a tertiary amine as a base. The reaction can be carried out at room temperature or under microwave irradiation.

A carboxylic acid VI, wherein PG represents a protecting group, such as allyl, is reacted with the amine V to obtain the amide VII, using a coupling agent, such as for example the combination of N,N'-diisopropylcarbodiimide and 1-hydroxybenzotriazole. An amine IVb is then added, by means of Michael reaction using a base and a solvent, such as N,N-dimethylformamide or dimethyl sulfoxide to obtain the intermediate VIII after cleavage from the resin using a mixture of trifluoroacetic acid, dichloromethane and water. The intermediate VIII is cyclized (intermediate IX) and deprotected in basic medium yielding the intermediate acid X.

The intermediate X can alternatively be prepared in the solid phase according to scheme 2, wherein the amine V' can be prepared from the amine IVa either by means of a reductive amination reaction with a glyoxylate in THF-AcOH using a reducing agent such as NaBH$_3$CN, or alternatively by means of alkylation with a bromoacetate or a bromoacetamide using a tertiary amine as a base. Subsequently, it is coupled to the acid VI to obtain the amide VII'. An amine IVb is then added and by means of Michael reaction and subsequent in situ cyclization produces the intermediate ester IX which through basic treatment yields compound X.

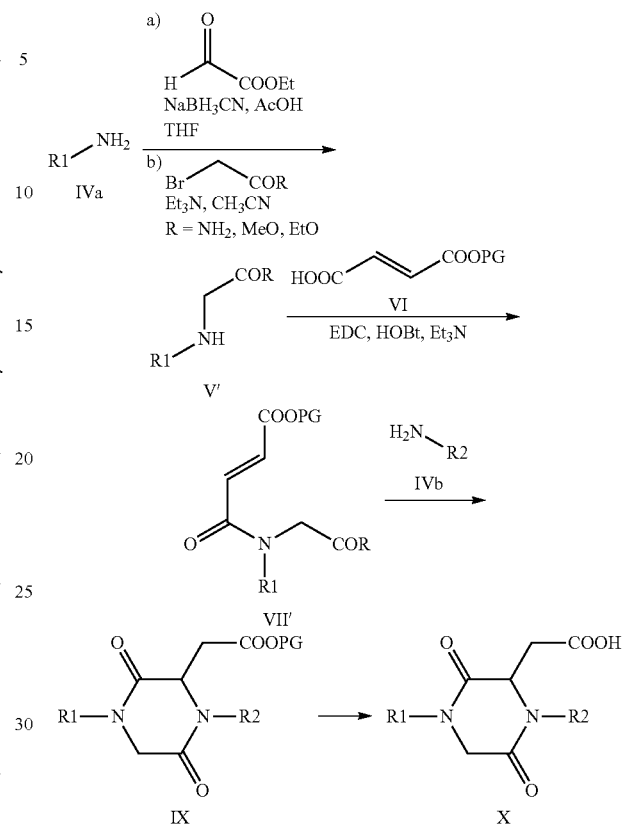

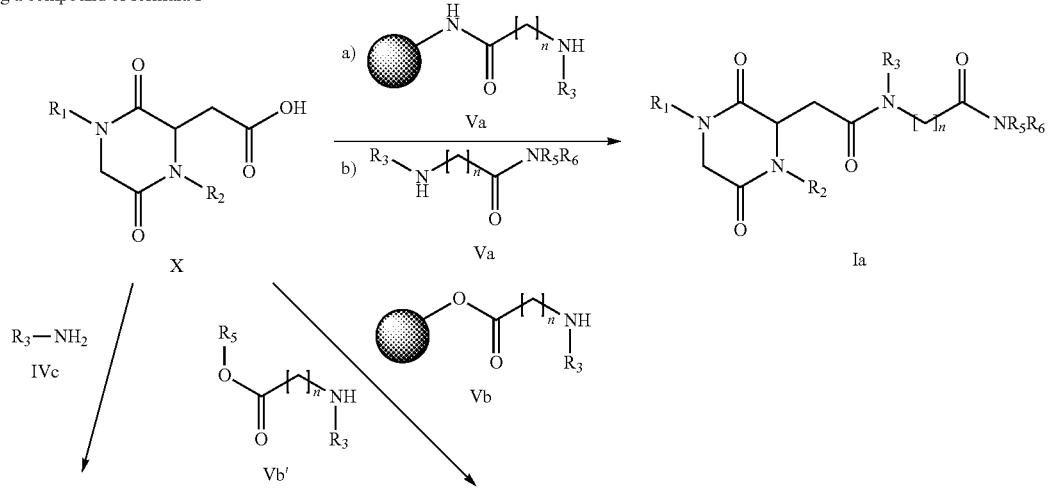

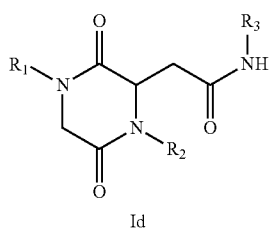

Id

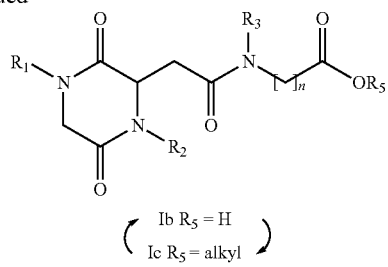

(Ib R₅ = H
Ic R₅ = alkyl)

A compound of formula Ia can be obtained from the intermediate X by coupling with an amine bound to a solid support Va or Va', obtained according to the methodology indicated above, in the presence of a coupling agent such as, for example, the combination of HATU and HOBT. The compound of formula Ib can be obtained in the manner similar to the synthesis of compound Ia, except in the case of solid phase in which the starting solid support (IIb) has a halogen group instead of an amino group, such as for example, the chlorotrityl resin, obtaining an acid after cleavage from the resin. The ester Ic can be synthesized by esterification of the corresponding acid Ib by means of common esterification methods in organic synthesis, such as for example, using methanol in an acid medium such as sulfuric acid. In the case of Ib, it can be obtained by means of saponifying the ester Ic. The compounds of formula Id can be obtained by reacting the intermediate X with a primary amine IVc.

An alternative strategy for obtaining the compounds of formula I can be carried out by means of acylating the amine II with an amino acid of formula XI (Method B).

Method B

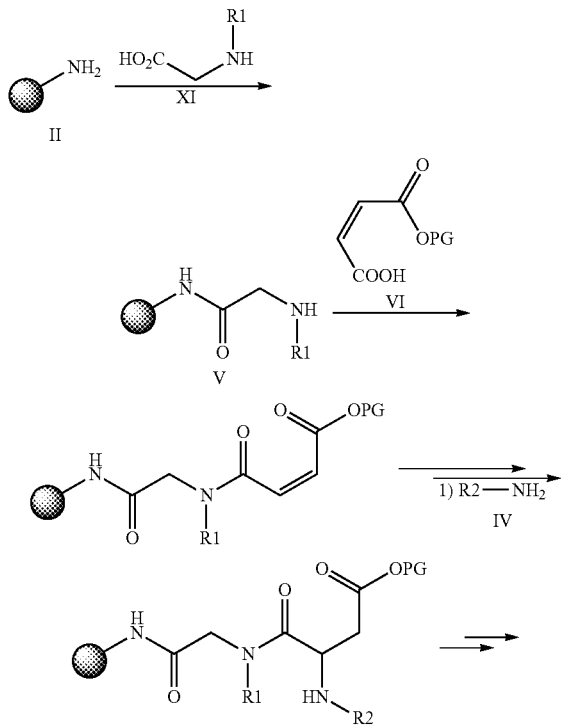

-continued

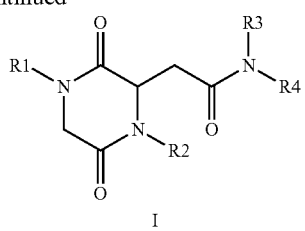

I

As is obvious for a person skilled in the field of the invention, it is possible to combine some of the steps of method A with some of the steps of method B to obtain a compound of formula I.

Alternatively, it is possible to obtain the compounds of formula Ie and If as shown in the scheme described below.

Scheme 3

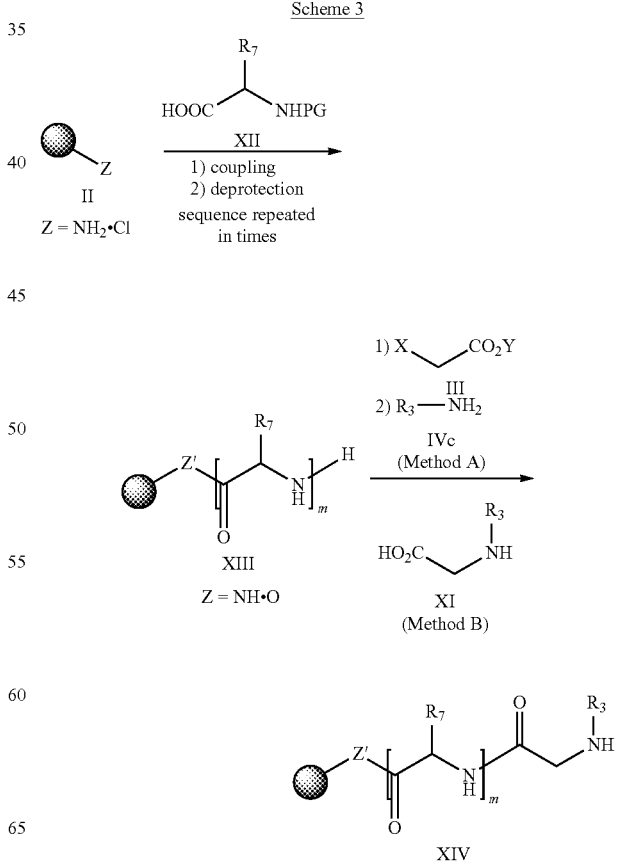

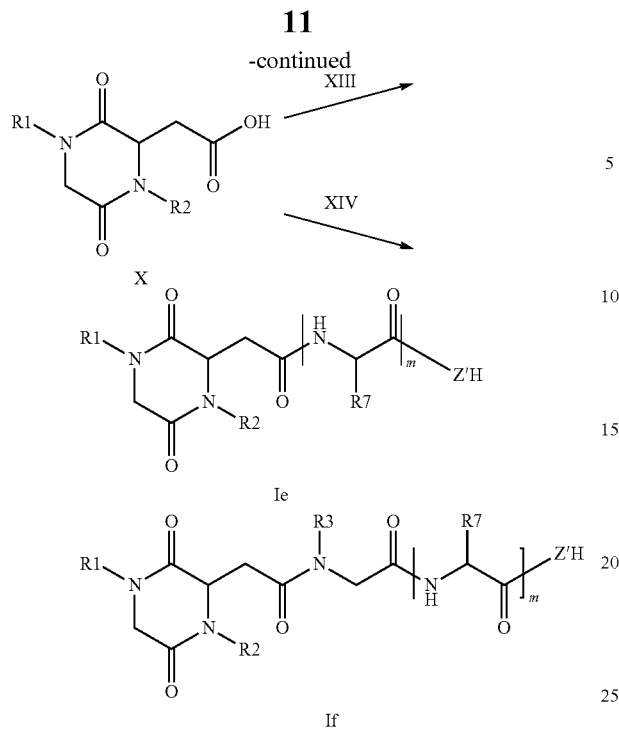

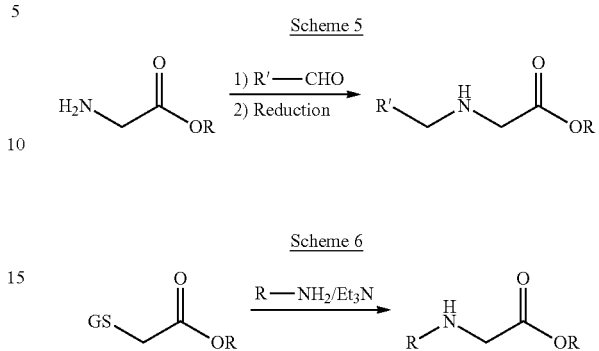

The peptide XIII and the pseudopeptide XIV which will be bound to the acid X can be obtained by means of standard peptide synthesis reactions. Therefore, the amine IIa (Z=NH$_2$) or chloride IIb (Z=Cl) resin can be reacted with a suitably protected amino acid (XII), using a suitable coupling agent. Optionally the process can sequentially be repeated, previously deprotecting the amine, to obtain the peptide XIII. The carboxylic acid X then reacts with XIII to obtain the compound Ie.

By combining the amino acid units (XIII) with a glycine unit (following method A or B), the pseudopeptide XIV is obtained, which will lead to obtaining If in the manner similar to that described above.

The primary amines used IVa, IVb and IVc are commercially available or can be obtained by means of known methods (March, Advanced Organic Chemistry, 1991, Ed. John Wiley & Sons) or by using, for example, the schemes described below.

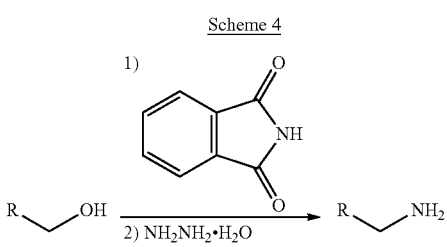

An amine can be obtained by Mitsunobu reaction starting from alcohol and potassium phthalimide in the presence of, for example, diethyl azodicarboxylate (DEAD) and triphenylphosphine in tetrahydrofuran as solvent and the subsequent release with hydrazine hydrate. (Mitsunobu, *J. Am. Chem. Soc.* 1972, 94, 679-680)

The N-substituted glycines V and XI can be synthesized by means of some of the methods shown below, such as for example, reductive amination of the corresponding glycine with a suitable aldehyde (Scheme 5) using reducing agents such as NaBH$_4$, NaBH$_3$CN or NaBH(AcO)$_3$ or by the nucleophilic substitution of an ester with an amine R—NH$_2$ (Scheme 6).

EXAMPLES

Abbreviations

AcOEt Ethyl acetate
Brine Saturated NaCl solution
DCM Dichloromethane
DIC N,N'-diisopropylcarbodiimide
DIPEA N,N-diisopropylethylamine
DMF N,N-dimethylformamide
DMSO Dimethyl sulfoxide
EDC 1-(3-dimethylaminopropyl)-3-ethylcarbodiimide
Eq. Molar equivalent
Et$_3$N Triethylamine
Fmoc 9-fluorenylmethoxycarbonyl
IPA Isopropyl alcohol
HATU 2-(1H-7-azabenzotriazol-1-yl)-1,1,3,3-tetramethyluronium hexafluorophosphate
HOBT 1-hydroxybenzotriazole
HPLC High performance liquid chromatography
HRMS High resolution mass spectrometry
MeOH Methanol
PyBOP Benzotriazol-1-yloxy-trispyrrolidinophosphonium hexafluorophosphate
RP Reverse phase
rt Room temperature
tr Retention time
UV Ultraviolet
TFA Trifluoroacetic acid The following examples serve to better illustrate the invention but they must not be considered as limiting the same.

The nomenclature used in the present document is based on the CFW_CHEMICAL_NAME function in Chemdraw for Excel version 12.

General Data:

The compounds were synthesized using a polystyrene AM RAM resin acquired from Rapp Polymere GmbH (Germany). In the reactions polystyrene syringes with a polyethylene disc were used using an HS501 digital IKA Labortechnik stirrer. In the reactions carried out by microwaves, a CEM Discover model with 10 ml glass reactors was used.

The products were analyzed by:

Method A: By means of an RP-HPLC using a Hewlett Packard Series 1100 (UV detector 1315A) equipment using an X-Terra C18 (15×0.46 cm, 5 μm) reverse phase column. The wavelength used for the UV detection was 210 nm. Mixtures of $CH_3CN$—$H_2O$ with 0.1% TFA at 1 ml/min were used as mobile phase. The analyses were conducted with a gradient from 20% to 70% of $CH_3CN$ (10 min), and from 70% to 100% (8 min).

Method B: The products were analyzed using an Agilent 1100 HPLC equipment, provided with a UV detector of variable wavelength and a mass spectrometer model 1100 VL. The wavelength used for the UV detection was 210 nm, whereas the MS detector has been operated in positive electrospray ionization mode and a 100 to 1300 m/z scan has been performed. Concerning chromatographic separation, the column used was a Kromasil 100 C18 (4.0×40 mm, 3.5 μm) set at 50° C., and 5 μl have been injected. For the elution one of the two solvent gradients described below was followed: 5-100% B in 7 min, 5% B 7-8.5 min. The flow rate of the mobile phase is 1.4 ml/min. Solvent A consists of 0.2% formic acid in water, whereas B is 0.2% formic acid in acetonitrile.

Method C: using Waters HPLC-UV-MS equipment provided with a detector having diodes in series and a mass spectrometer model EMD1000. The wavelength used for UV detection was 210 nm, whereas the MS detector has been operated in a positive electrospray ionization mode and a 100 to 1000 m/z scan has been performed. Concerning chromatographic separation, the column used was a Kromasil C18 (2.1×50 mm, 3.5 μm) set at 50° C. and 2 μl have been injected. For the elution, the following gradient was followed: 5-100% B, 0-5 min, 100% B, 5-6.5 min, 5% B, 6.5-8 min. The flow rate of the mobile phase is 0.5 ml/min.

The high resolution mass spectrometry was carried out by HPLC-HRMS using a Waters Acquity HPLC equipment coupled to a Waters orthogonal acceleration time of flight mass spectrometer model LCT Premier XE. The chromatographic analysis was conducted by means of a Waters Acquity C18 column (10×2.1 mm, 1.7 μm).

Mixtures of $CH_3CN$—$H_2O$ with 20 mM formic acid at 0.3 ml/min were used as the mobile phase. The analyses were conducted with a gradient from 50% to 100% of $CH_3CN$ in 6 min.

Intermediate VI

VI: (Z)-2-butenedioic acid allyl ester 1.8 ml allyl alcohol (26 mmol, 1.3 eq.) were added to a 2 g solution of maleic anhydride (20 mmol) in chloroform. The reaction mixture was stirred at reflux for 5 h. The resulting solution was treated with 1N HCl and was extracted with chloroform. The organic extracts were washed with a saturated sodium chloride solution, dried on anhydrous magnesium sulfate and filtered. The solvent was evaporated at reduced pressure, and the residue obtained was identified as intermediate VI in the form of an oil (95% purity, 85% yield).

Intermediates X

X.1: 2-(4-(2,4-dichlorophenethyl)-1-(3,3-diphenyl-propyl)-3,6-dioxopiperazin-2-yl)acetic acid

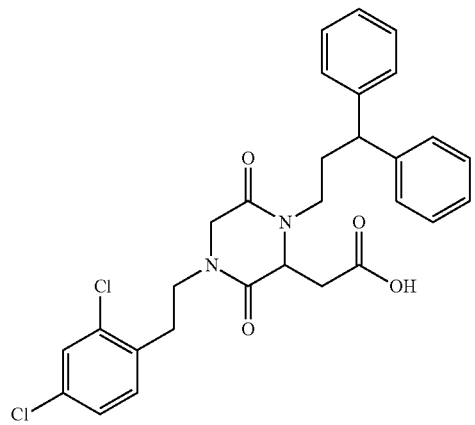 [SMILES: O=C(O)CC1C(=O)N(CCc2ccc(Cl)cc2Cl)CC(=O)N1CCC(c1ccccc1)c1ccccc1]

A mixture of 2 g of Fmoc-Rink Amide AM polystyrene resin (0.61 mmol/g resin, 1.22 mmol) and 12 ml of 20% piperidine in DMF was stirred in a microwave reactor for 2 min at 35° C. The resin was filtered and washed with DMF (3×15 ml), isopropyl alcohol (3×15 ml) and DCM (3×15 ml). The resin was treated with a solution of bromoacetic acid (III, 840 mg, 5 eq.) and N,N'-diisopropylcarbodiimide (1.15 ml, 5 eq.) in DMF (12 ml). The reaction mixture was stirred for 2 min at 60° C. in a microwave reactor. The resin was filtered and washed with DMF (3×15 ml), isopropyl alcohol (3×15 ml) and DCM (3×15 ml). A solution of 2,4-dichlorophenethylamine (IVa, 1.035 ml, 5 eq.) and triethylamine (0.85 ml, 5 eq.) in 12 ml of DMF was added to the resin and the suspension was stirred for 2 min at 90° C. activated by microwaves. The supernatant was removed and the reaction was repeated in the same conditions. The resin V obtained was filtered and washed with DMF (3×15 ml), isopropyl alcohol (3×15 ml) and DCM (3×15 ml). Then, the resin was treated with a solution of (Z)-2-butenedioic acid allyl ester (VI, 957 mg, 5 eq.), HOBT (825 mg, 5 eq.) and DIC (770 μL, 5 eq.) in DCM:DMF (2:1, 123 ml). The reaction mixture was stirred at room temperature for 30 min and was filtered. The resin was dried and washed with DMF (3×15 ml), isopropyl alcohol (3×15 ml) and DCM (3×15 ml). Then, a solution of 3,3-diphenylpropylamine (IVb, 1.29 g, 5 eq.) and triethylamine (0.85 ml, 5 eq.) in 12 ml of DMF was added to the resin and the suspension was stirred for 3 h at room temperature. The resin was filtered and the reaction was repeated for 16 h at the same temperature. The supernatant was removed and the resin was dried and washed with DMF (3×15 ml), isopropyl alcohol (3×15 ml) and DCM (3×15 ml). Cleavage from the solid phase was performed by treatment with a 60:40:2 TFA/DCM/water mixture (20 ml) for 30 min at room temperature.

The reaction mixture was filtered and the solvents were evaporated at reduced pressure. Cyclization was then performed by treating the residue obtained with 20 ml of dioxane for 1.5 h at reflux (monitoring the reaction by HPLC). A 1:2 solution (9 ml) of 4N sodium hydroxide and allyl alcohol was then added and the mixture was stirred for 45 min at reflux. The crude reaction product was acidified with 1N hydrochloric acid and the solvent was evaporated. The resulting solution was extracted with ethyl acetate (3×50 ml) and the organic extracts were washed with a saturated NaCl solution (2×100 ml); they were dried on anhydrous MgSO4 and were evaporated at reduced pressure to obtain 450 mg of the desired product (X, 70% purity, 95% yield at 210 nm). HRMS (M+H)$^+$ calculated for $C_{29}H_{29}Cl_2N_2O_4$, 539.1504, experimental, 539.1514.

The following compounds were prepared by following a method similar to that described in the example above but by using different amines:

| Ex. | Structure | Compound | HRMS (M + H)$^+$: Calculated | Experim. |
|---|---|---|---|---|
| X.2 | 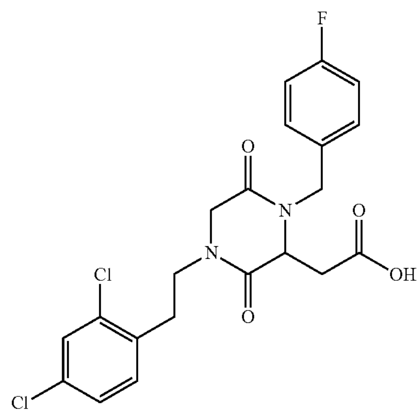 [SMILES: O=C(O)CC1C(=O)N(CCc2ccc(Cl)cc2Cl)CC(=O)N1Cc1ccc(F)cc1] | 2-(4-(2,4-dichlorophenethyl)-1-(4-fluorobenzyl)-3,6-dioxopiperazin-2-yl)acetic acid | $C_{21}H_{19}Cl_2FN_2O_4$ 453.0784 | 453.0782 |
| X.3 | 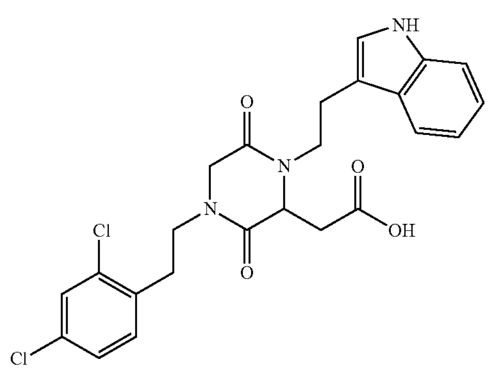 [SMILES: O=C(O)CC1C(=O)N(CCc2ccc(Cl)cc2Cl)CC(=O)N1CCc1c[nH]c2ccccc12] | 4-(2,4-dichlorophenethyl)-2-(1-(2-(1H-indol-3-yl)ethyl)-3,6-dioxopiperazin-2-yl) acetic acid | $C_{24}H_{23}Cl_2N_3O_4$ 488.1144 | 488.1131 |
| X.4 | 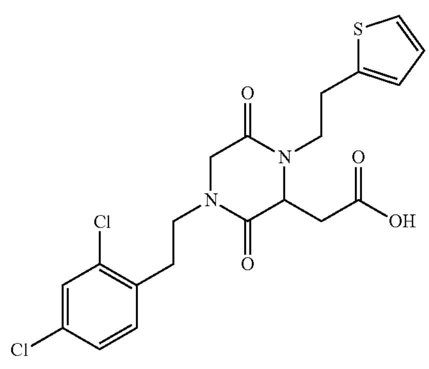 [SMILES: O=C(O)CC1C(=O)N(CCc2ccc(Cl)cc2Cl)CC(=O)N1CCc1cccs1] | 2-(4-(2,4-dichlorophenethyl)-3,6-dioxo-1-(2-(thiophen-2-yl)ethyl)piperazin-2-yl) acetic acid | $C_{20}H_{20}Cl_2N_2O_4S$ 455.0599 | 455.0594 |

-continued

| Ex. | Structure | Compound | HRMS (M + H)+: Calculated | Experim. |
|---|---|---|---|---|
| X.5 | 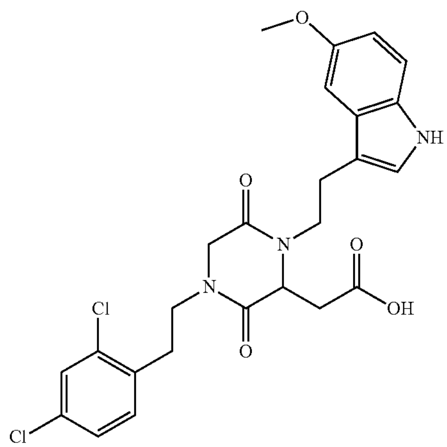 [SMILES: COc1ccc2[nH]cc(CCN3C(=O)CN(CCc4ccc(Cl)cc4Cl)C(=O)C3CC(=O)O)c2c1] | 2-(4-(2,4-dichlorophenethyl)-1-(2-(5-methoxy-1H-indol-3-yl)ethyl)-3,6-dioxopiperazin-2-yl) acetic acid | $C_{25}H_{25}Cl_2N_3O_5$ 518.1250 | 518.1270 |
| X.6 | 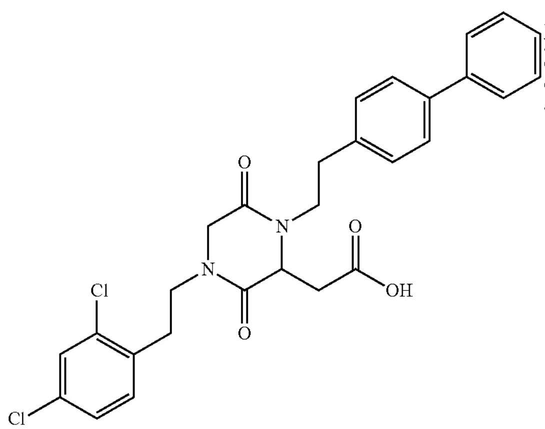 [SMILES: O=C(O)CC1C(=O)N(CCc2ccc(Cl)cc2Cl)CC(=O)N1CCc1ccc(-c2ccccc2)cc1] | 2-(1-(2-([1,1'-biphenyl]-4-yl)ethyl)-4-(2,4-dichlorophenethyl)-3,6-dioxopiperazin-2-yl) acetic acid | $C_{28}H_{26}Cl_2N_2O_4$ 515.1348 | 525.1348 |
| X.7 | 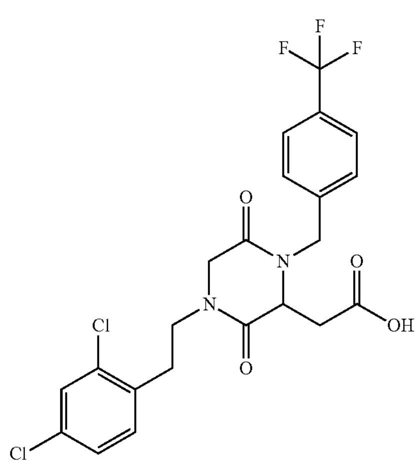 [SMILES: O=C(O)CC1C(=O)N(CCc2ccc(Cl)cc2Cl)CC(=O)N1Cc1ccc(C(F)(F)F)cc1] | 2-(4-(2,4-dichlorophenethyl)-3,6-dioxo-1-(4-(trifluoromethyl)benzyl)piperazin-2-yl) acetic acid | $C_{22}H_{19}Cl_2F_3N_2O_4$ 503.0752 | 503.0757 |

X.13: 2-(4-(2,4-dichlorophenethyl)-3,6-dioxo-1-(4-(trifluoromethyl)benzyl)piperazin-2-yl)acetic acid

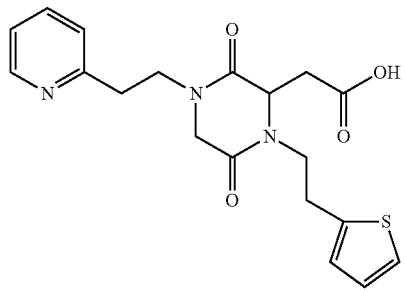 [SMILES: O=C(O)CC1C(=O)N(CCc2ccccn2)CC(=O)N1CCc1cccs1]

Step 1 Intermediate V'

7.55 mL of Et₃N and 2.50 g (27 mmol) of bromoacetamide were added to a solution of 5 g (41 mmol) of 2-(2-pyridyeethylamine in 300 mL of dioxane. The resulting mixture is heated to reflux overnight. The solution is evaporated to dryness and purified in silica gel using a mixture of AcOEt:MeOH:NH₃ (10:1:0.01) as eluent, yielding 2.39 g of the intermediate V'. Method B: tr: 0.261, m/z: 180.

Step 2: Intermediate VII'

4.90 mL of Et₃N, 3.24 g (24 mmol) of HOBT, 4.60 g (24 mmol) of EDC and the product of step 1 are added to a solution consisting of 2.31 g (16.0 mmol) of maleic acid monoethyl ester in 100 mL of DMF. The suspension formed is kept under stirring at rt for 18 h. It is then treated with water and AcOEt is added, the organic phase is separated and the aqueous phase is extracted one more time with AcOEt. The organic phases are pooled and are successively washed with saturated NaHCO₃ solution and brine. It is subsequently dried on anhydrous Na₂SO₄, the solvent is filtered and evaporated at reduced pressure. 1.5 g of the compound identified as example VII'.13 are obtained. Method B: tr: 1.094, m/z: 306.

Step 3: Intermediate IX 0.8 mL (5.89 mmol) of Et₃N and 1.5 g of the intermediate VII'.13 (4.91 mmol) were added to a solution of 2-thiophenylethylamine (0.63 mL, 5.4 mmol) in 40 mL of dioxane and the resulting solution was stirred for 18 h at reflux. The solution was evaporated to dryness and was purified by means of silica gel column chromatography, using a (10:1:0.01) mixture of AcOEt:MeOH:NH₃ as eluent, yielding 510 mg of an oil identified as intermediate IX.13 ethyl (2-(3,6-dioxo-4-(2-(pyridin-2-yeethyl)-1-(2-(thiophen-2-yeethyl)piperazin-2-yl)acetate). Method A: tr: 2.289, m/z: 416.

The following intermediates were prepared in the manner similar to intermediate IX.13:

| Int. | structure | name | method | tr | m/z |
|---|---|---|---|---|---|
| IX.3 | 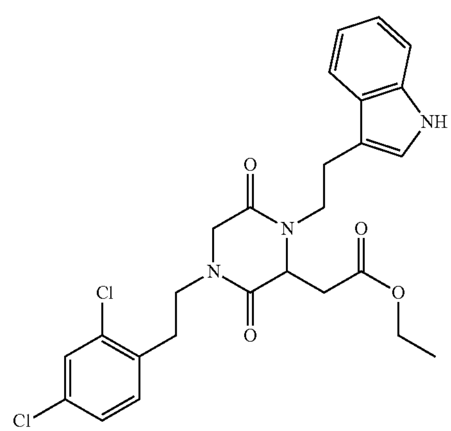 [SMILES: CCOC(=O)CC1C(=O)N(CCc2ccc(Cl)cc2Cl)CC(=O)N1CCc1c[nH]c2ccccc12] | Ethyl 2-(1-(2-(1H-indol-3-yl)ethyl)-4-(2,4-dichlorophenethyl)-3,6-dioxopiperazin-2-yl)acetate | B | 4.100 | 516 518 |
| IX.4 | 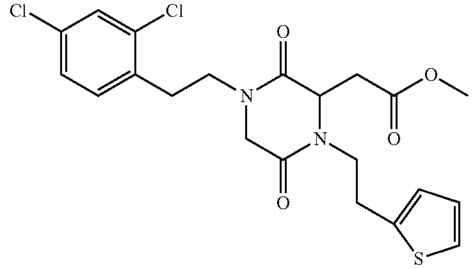 [SMILES: COC(=O)CC1C(=O)N(CCc2ccc(Cl)cc2Cl)CC(=O)N1CCc1cccs1] | Methyl 2-(4-(2,4-dichlorophenethyl)-3,6-dioxo-1-(2-(thiophen-2-yl)ethyl)piperazin-2-yl)acetate | B | 3.984 | 469 471 |

| Int. | structure | name | method | tr | m/z |
|---|---|---|---|---|---|
| IX.8 | 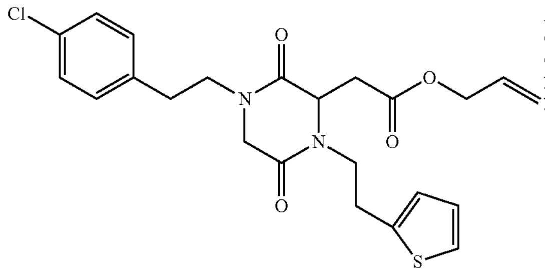 [SMILES: C=CCOC(=O)CC1C(=O)N(CCc2ccc(Cl)cc2)CC(=O)N1CCc1cccs1] | Allyl 2-(4-(4-chlorophenethyl)-3,6-dioxo-1-(2-(thiophen-2-yl)ethyl)piperazin-2-yl)acetate | B | 4.019 | 461 463 |
| IX.9 | 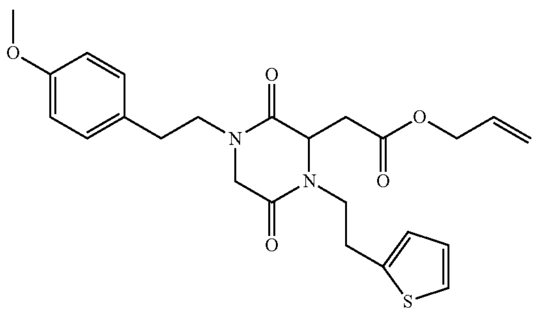 [SMILES: C=CCOC(=O)CC1C(=O)N(CCc2ccc(OC)cc2)CC(=O)N1CCc1cccs1] | Allyl 2-(4-(4-methoxyphenethyl)-3,6-dioxo-1-(2-(thiophen-2-yl)ethyl)piperazin-2-yl)acetate | B | 3.734 | 457 |
| IX.10 | 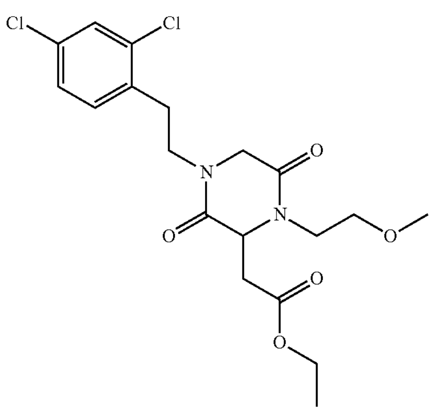 [SMILES: CCOC(=O)CC1C(=O)N(CCc2ccc(Cl)cc2Cl)CC(=O)N1CCOC] | Ethyl 2-(4-(2,4-dichlorophenethyl)-1-(2-methoxyethyl)-3,6-dioxopiperazin-2-yl)acetate | B | 3.637 | 431 433 |
| IX.11 | 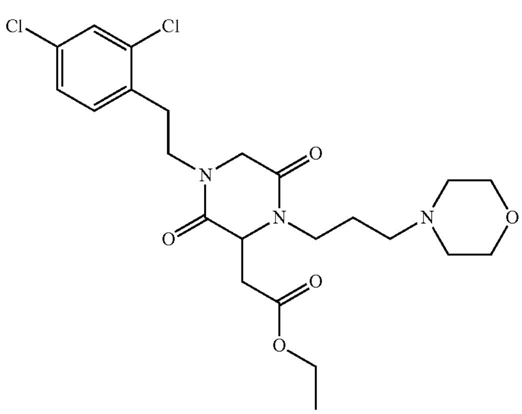 [SMILES: CCOC(=O)CC1C(=O)N(CCc2ccc(Cl)cc2Cl)CC(=O)N1CCCN1CCOCC1] | Ethyl 2-(4-(2,4-dichlorophenethyl)-1-(3-morpholinopropyl)-3,6-dioxopiperazin-2-yl)acetate | B | 2.737 | 500 502 |

-continued

| Int. | structure | name | method | tr | m/z |
|---|---|---|---|---|---|
| IX.12 | 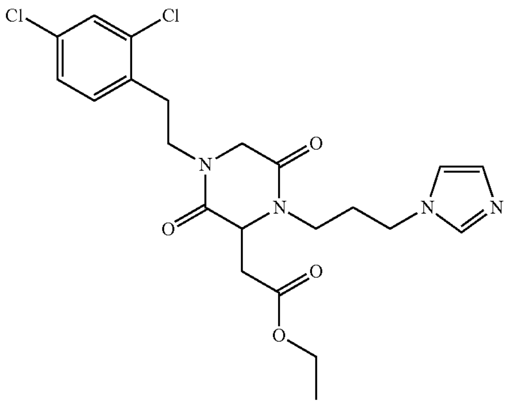 [SMILES: CCOC(=O)CC1C(=O)N(CCc2ccc(Cl)cc2Cl)CC(=O)N1CCCn1ccnc1] | Ethyl 2-(1-(3-(1H-imidazol-1-yl)propyl)-4-(2,4-dichlorophenethyl)-3,6-dioxopiperazin-2-yl)acetate | B | 2.739 | 482 484 |
| IX.14 | 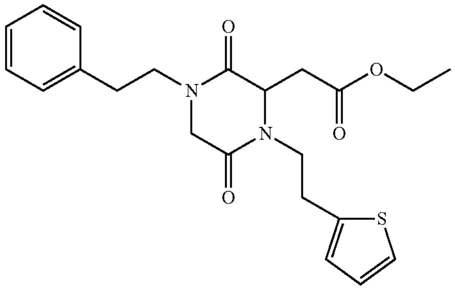 [SMILES: CCOC(=O)CC1C(=O)N(CCc2ccccc2)CC(=O)N1CCc1cccs1] | Ethyl 2-(3,6-dioxo-4-phenethyl-1-(2-(thiophen-2-yl)ethyl)piperazin-2-yl)acetate | B | 3.665 | 415 |
| IX.15 | 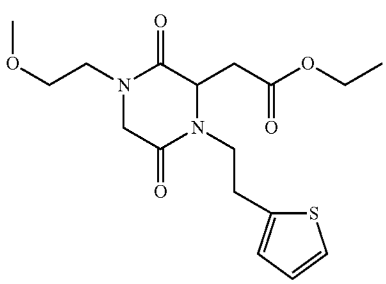 [SMILES: CCOC(=O)CC1C(=O)N(CCOC)CC(=O)N1CCc1cccs1] | Ethyl 2-(4-(2-methoxyethyl)-3,6-dioxo-1-(2-(thiophen-2-yl)ethyl)piperazin-2-yl)acetate | B | 2.858 | 369 |
| IX.16 | 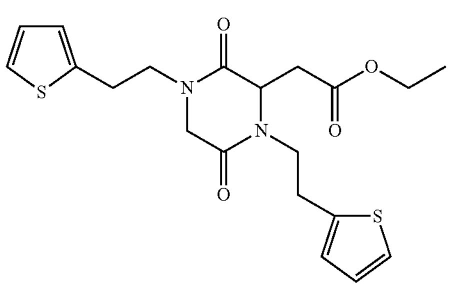 [SMILES: CCOC(=O)CC1C(=O)N(CCc2cccs2)CC(=O)N1CCc1cccs1] | Ethyl 2-(3,6-dioxo-1,4-bis(2-(thiophen-2-yl)ethyl)piperazin-2-yl)acetate | B | 3.560 | 421 |
| IX.17 | 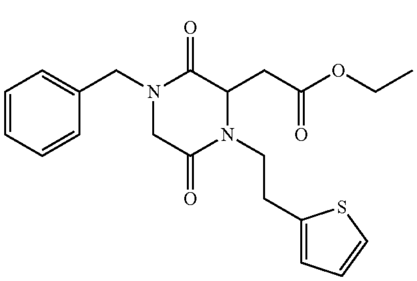 [SMILES: CCOC(=O)CC1C(=O)N(Cc2ccccc2)CC(=O)N1CCc1cccs1] | Ethyl 2-(4-benzyl-3,6-dioxo-1-(2-(thiophen-2-yl)ethyl)piperazin-2-yl)acetate | B | 3.538 | 401 |

| Int. | structure | name | method | tr | m/z |
|---|---|---|---|---|---|
| IX.18 | 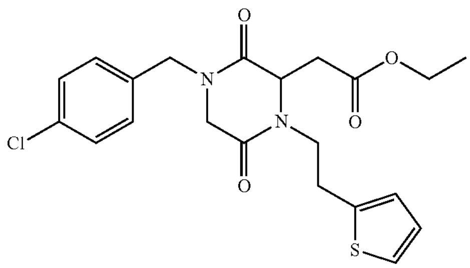 [SMILES: CCOC(=O)CC1C(=O)N(Cc2ccc(Cl)cc2)CC(=O)N1CCc1cccs1] | Ethyl 2-(4-(4-chlorobenzyl)-3,6-dioxo-1-(2-(thiophen-2-yl)ethyl)piperazin-2-yl)acetate | B | 4.358 | 435 |
| IX.19 | 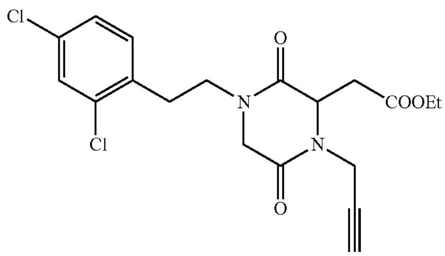 [SMILES: C#CCN1C(=O)CN(CCc2ccc(Cl)cc2Cl)C(=O)C1CC(=O)OCC] | Ethyl 2-(4-(2,4-dichlorophenethyl)-3,6-dioxo-1-(prop-2-yn-1-yl)piperazin-2-yl)acetate | C | 4.233 | 411 |
| IX.22 | 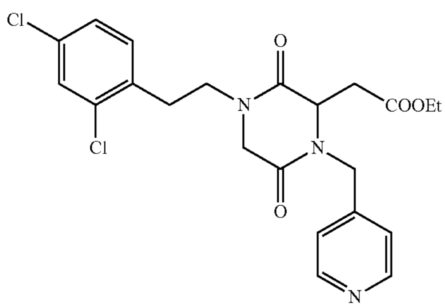 [SMILES: CCOC(=O)CC1C(=O)N(CCc2ccc(Cl)cc2Cl)CC(=O)N1Cc1ccncc1] | Ethyl 2-(4-(2,4-dichlorophenethyl)-3,6-dioxo-1-(pyridin-4-ylmethyl)piperazin-2-yl)acetate | C | 3.412 | 464 |

Step 4: intermediate X 1.6 mL of a solution of 1N LiOH were added to a solution of 550 mg (1.32 mmol) of intermediate IX.13 in 15 mL of a MeOH:THF mixture (1:3), and it was left to stir at rt the overnight. It is then diluted in AcOEt and washed with water, the aqueous phase is acidified with a 1N HCl solution until pH=7 and is extracted with AcOEt. Finally, the organic phases are pooled, dried on anhydrous $Na_2SO_4$, filtered and the solvent is evaporated at reduced pressure. 330 mg of a colorless oil identified as intermediate X.13 are obtained.

Method B: tr: 1.768, m/z: 388

The following intermediates were prepared in the manner similar to intermediate X.13:

| Int. | structure | name | method | tr | m/z |
|---|---|---|---|---|---|
| X.8 | 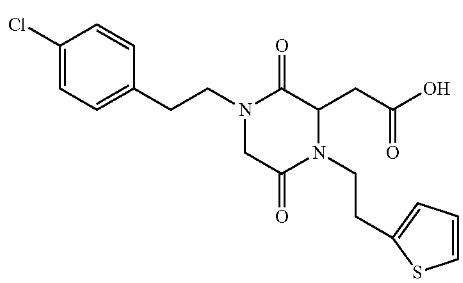 [SMILES: O=C(O)CC1C(=O)N(CCc2ccc(Cl)cc2)CC(=O)N1CCc1cccs1] | 2-(4-(4-chlorophenethyl)-3,6-dioxo-1-1(2-(thiophen-2-yl)ethyl)piperazin-2-yl) acetic acid | B | 3.314 | 4214 23 |

-continued
| Int. | structure | name | method | tr | m/z |
|---|---|---|---|---|---|
| X.9 | 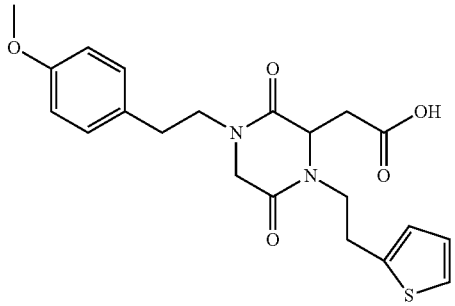 [SMILES: COc1ccc(CCN2CC(=O)N(CCc3cccs3)C(CC(=O)O)C2=O)cc1] | 2-(4-(4-methoxyphenethyl)-3,6-dioxo-1-(2-(thiophen-2-yl)ethyl)piperazin-2-yl) acetic acid | B | 3.007 | 417 |
| X.10 | 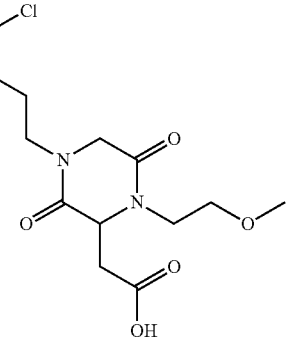 | 2-(4-(2,4-dichlorophenethyl)-1-(2-methoxyethyl)-3,6-dioxpiperazin-2-yl) acetic acid | B | 2.979 | 403 405 |
| X.11 | 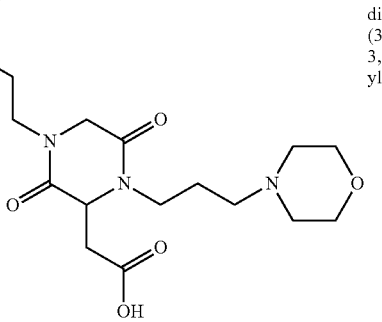 | 2-(4-(2,4-dichlorophenethyl)-1-(3-morpholinopropyl)-3,6-dioxopiperazin-2-yl) acetic acid | B | 2.359 | 472 474 |
| X.12 | 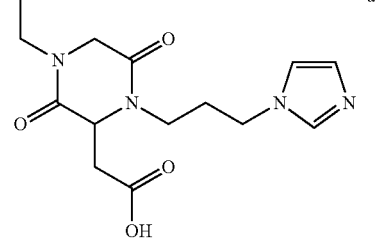 | 2-(1-(3-(1H-imidazol-1-yl)propyl)-4-(2,4-dichlorophenethyl)-3,6-dioxopiperaizn-2-yl) acetic acid | B | 2.302 | 454 |

-continued
| Int. | structure | name | method | tr | m/z |
|---|---|---|---|---|---|
| X.13 | 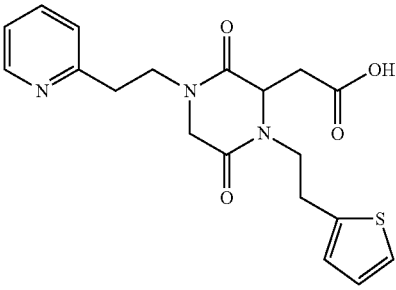 [SMILES: O=C(O)CC1C(=O)N(CCc2ccccn2)CC(=O)N1CCc1cccs1] | 2-(3,6-dioxo-4-(2-(pyridin-2-yl)ethyl)-1-(2-(thiophen-2-yl)ethyl)piperazin-2-yl)acetic acid | B | 1.768 | 388 |
| X.14 | 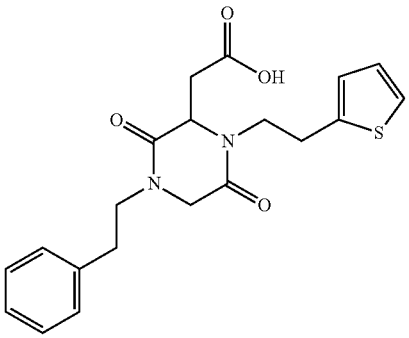 [SMILES: O=C(O)CC1C(=O)N(CCc2ccccc2)CC(=O)N1CCc1cccs1] | 2-(3,6-dioxo-4-phenethyl-1-(2-(thiophen-2-yl)ethyl)piperazin-2-yl)acetic acid | B | 3.028 | 387 |
| X.15 | 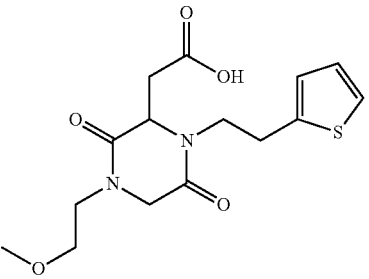 [SMILES: COCCN1CC(=O)N(CCc2cccs2)C(CC(=O)O)C1=O] | 2-(4-(2-methoxyethyl)-3,6-dioxo-1-(2-(thiophen-2-yl)ethyl)piperazin-2-yl)acetic acid | B | 2.221 | 341 |
| X.16 | 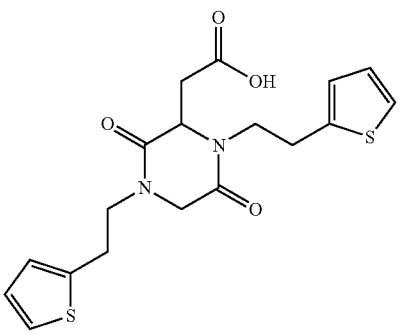 [SMILES: O=C(O)CC1C(=O)N(CCc2cccs2)CC(=O)N1CCc1cccs1] | 2-(3,6-dioxo-1,4-bis(2-(thiophen-2-yl)ethyl)piperazin-2-yl)acetic acid | B | 2.933 | 393 |

-continued
| Int. | structure | name | method | tr | m/z |
|---|---|---|---|---|---|
| X.17 | 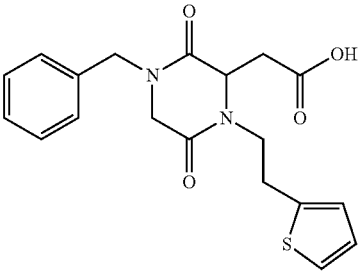 [SMILES: O=C(O)CC1C(=O)N(Cc2ccccc2)CC(=O)N1CCc1cccs1] | 2-(4-benzyl-3,6-dioxo-1-(2-(thiophen-2-yl)ethyl)piperazin-2-yl) acetic acid | C | 3.474 | 373 |
| X.19 | 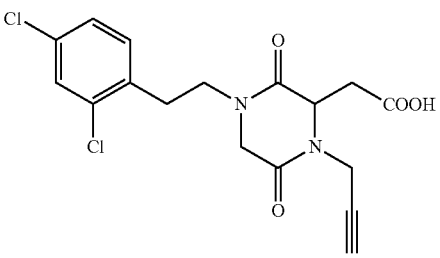 [SMILES: C#CCN1C(=O)CN(CCc2ccc(Cl)cc2Cl)C(=O)C1CC(=O)O] | 2-(4-(2,4-dichlorophenethyl)-3,6-dioxo-1-(prop-2-yn-1-yl)piperazin-2-yl) acetic acid | C | 3.615 | 383<br>385 |
| X.22 | 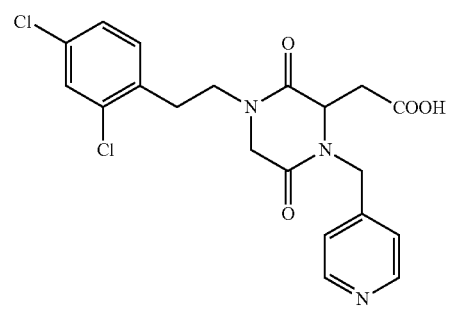 [SMILES: O=C(O)CC1C(=O)N(CCc2ccc(Cl)cc2Cl)CC(=O)N1Cc1ccncc1] | 2-(4-(2,4-dichlorophenethyl)-3,6-dioxo-1-(pyridin-4-ylmethyl)piperazin-2-yl) acetic acid | C | 2.995 | 436<br>438 |

Compounds of Formula Ia a) Ia.1.2: N-(2-amino-2-oxoethyl)-N-(2,4-dichlorophenethyl)-2-(4-(2,4-dichlorophenethyl)-1-(3,3-diphenylpropyl)-3,6-dioxopiperazin-2-yl)acetamide

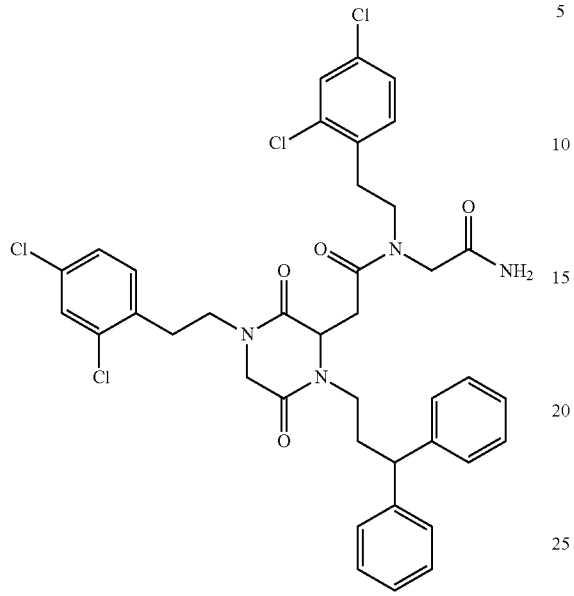

The acid X.1 (100 mg, 1.1 eq.), HOBt (40 mg, 1.5 eq.), HATU (105 mg, 1.5 eq.) and DIPEA (95 μL, 3 eq.) were added to a suspension of resin Va (0.61 mmol/g resin, 0.17 mmol) with the suitable amine and previously swelled with a 2:1 DCM:DMF solution (3 ml). The reaction mixture was stirred at room temperature for 16 h. The resin was dried and washed with DMF (3×3 ml), isopropyl alcohol (3×3 ml) and DCM (3×3 ml) and was subsequently treated with a mixture of 60:40:2 TFA/DCM/water (5 ml) for 30 min at room temperature. The resin was filtered and the filtrate was evaporated at reduced pressure to obtain 73 mg of the desired compound (Ia.1.2, 51% yield, 91% purity). HRMS (M+H)$^+$ calculated for $C_{39}H_{39}Cl_4N_4O_4$, 767.1725, experimental, 767.1741.

| Ex | Structure | Compound | HRMS (M + H)$^+$: Calculated | Experimental |
|---|---|---|---|---|
| Ia.1.1 | 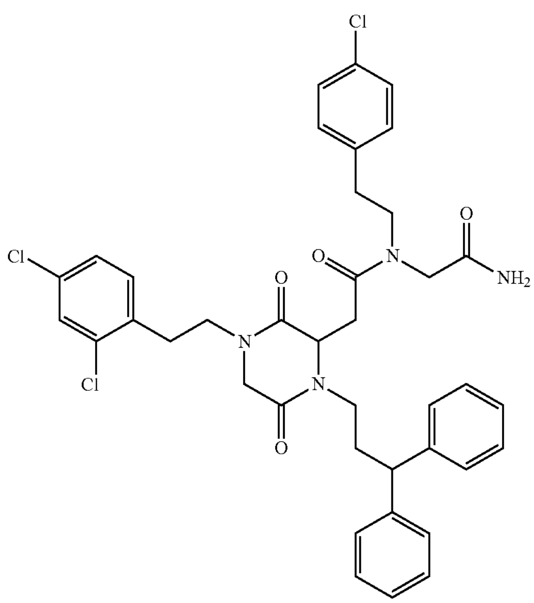 | N-(2-amino-2-oxoethyl)-N-(4-chlorophenethyl)-2-(4-(2,4-dichlorophenethyl)-1-(3,3-diphenylpropyl)-3,6-dioxopiperazin-2-yl)acetamide | $C_3H_{39}Cl_3N_4O_4$ 733.2115 | 733.2090 |

-continued

| Ex | Structure | Compound | HRMS (M + H)+: Calculated | Experimental |
|---|---|---|---|---|
| Ia.1.8 | 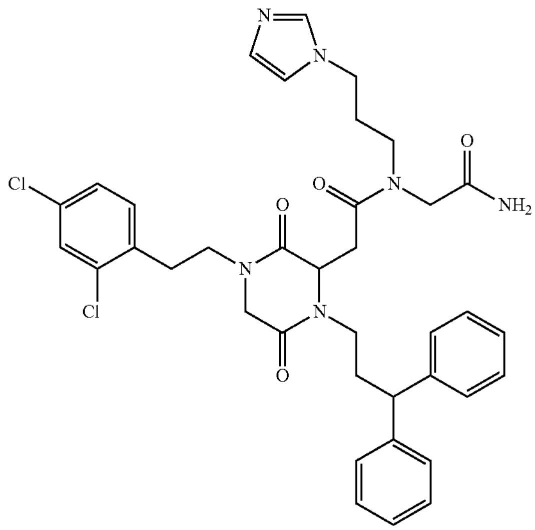 [SMILES: NC(=O)CN(CCCn1ccnc1)C(=O)CC1C(=O)N(CCc2ccc(Cl)cc2Cl)CC(=O)N1CCC(c1ccccc1)c1ccccc1] | N-(3-(1H-imidazol-1-yl)propyl)-N-(2-amino-2-oxoethyl)-2-(4-(2,4-dichlorophenethyl)-1-(3,3-diphenylpropyl)-3,6-dioxopiperaizn-2-yl)acetamide | $C_{37}H_{40}Cl_2N_6O_4$ 703.2566 | 703.2582 |
| Ia.1.16 | 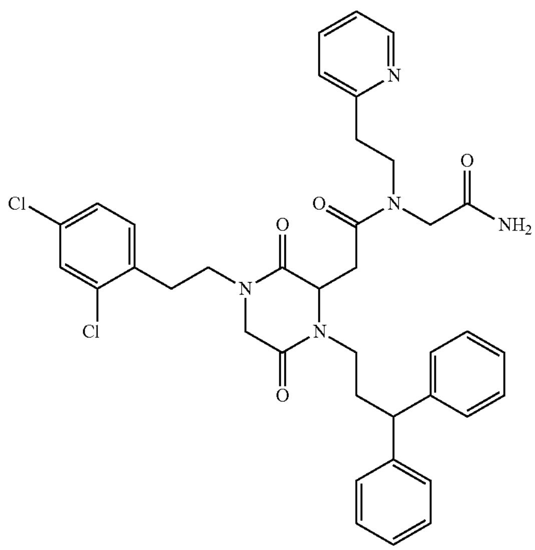 [SMILES: NC(=O)CN(CCc1ccccn1)C(=O)CC1C(=O)N(CCc2ccc(Cl)cc2Cl)CC(=O)N1CCC(c1ccccc1)c1ccccc1] | N-(2-amino-2-oxoethyl)-2-(4-(2,4-dichlorophenethyl)-1-(3,3-diphenylpropyl)-3,6-dioxopiperazin-2-yl)-N-(2-(pyridin-2-yl)ethyl)acetamide | $C_{38}H_{39}Cl_2N_5O_4$ 700.2457 | 700.2480 |
| Ia.1.20 | 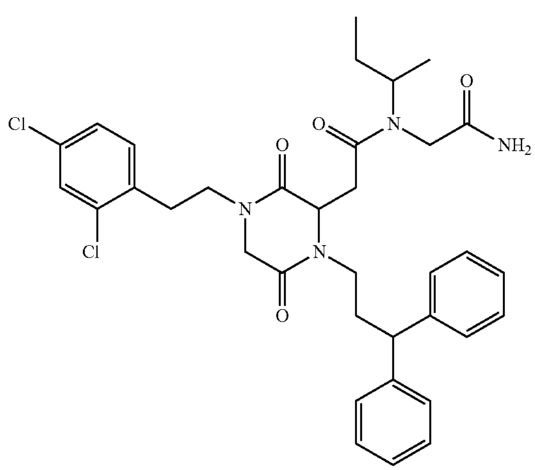 [SMILES: CCC(C)N(CC(N)=O)C(=O)CC1C(=O)N(CCc2ccc(Cl)cc2Cl)CC(=O)N1CCC(c1ccccc1)c1ccccc1] | N-(2-amino-2-oxoethyl)-N-(sec-butyl)-2-(4-(2,4-dichlorophenethyl)-1-(3,3-diphenylpropyl)-3,6-dioxopiperazin-2-yl)acetamide | $C_{35}H_{40}Cl_2N_4O_4$ 651.2505 | 651.2517 |

-continued

| Ex | Structure | Compound | HRMS (M + H)+: Calculated | Experimental |
|---|---|---|---|---|
| Ia.1.21 | 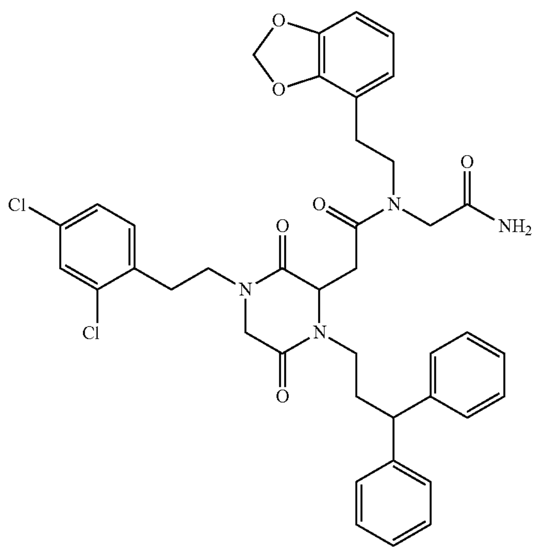 [SMILES: NC(=O)CN(CCc1cccc2c1OCO2)C(=O)CC1C(=O)N(CCc2ccc(Cl)cc2Cl)CC(=O)N1CCC(c1ccccc1)c1ccccc1] | N-(2-amino-2-oxoethyl)-2-(4-(2,4-dichlorophenethyl)-1-(3,3-diphenylpropyl)-3,6-dioxopiperazin-2-yl)-N-((tetrahydrofuran-2-yl)methyl)acetamide | $C_{40}H_{40}Cl_2N_4O_6$ 743.2403 | 743.2405 |
| Ia.1.22 | 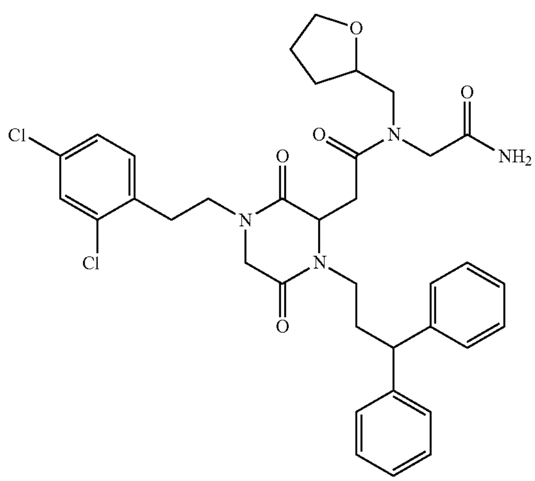 [SMILES: NC(=O)CN(CC1CCCO1)C(=O)CC1C(=O)N(CCc2ccc(Cl)cc2Cl)CC(=O)N1CCC(c1ccccc1)c1ccccc1] | N-(2-amino-2-oxoethyl)-2-(4-(2,4-dichlorophenethyl)-1-(3,3-diphenylpropyl)-3,6-dioxopiperazin-2-yl)-N-phenethylacetamide | $C_{36}H_{40}Cl_2N_4O_5$ 679.2454 | 679.2455 |
| Ia.1.23 | 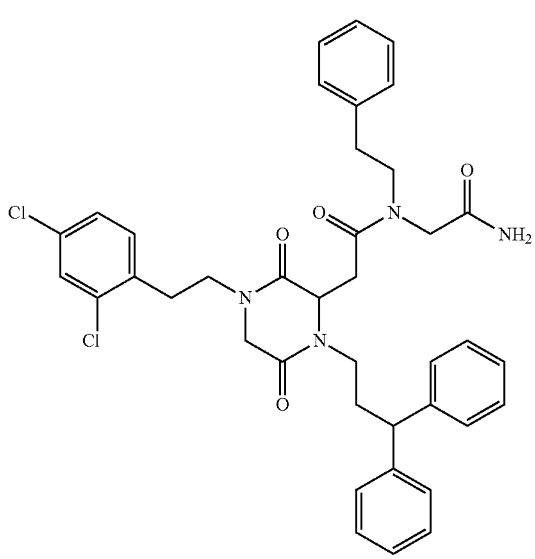 [SMILES: NC(=O)CN(CCc1ccccc1)C(=O)CC1C(=O)N(CCc2ccc(Cl)cc2Cl)CC(=O)N1CCC(c1ccccc1)c1ccccc1] | N-(2-amino-2-oxoethyl)-2-(4-(2,4-dichlorophenethyl)-1-(3,3-diphenylpropyl)-3,6-dioxopiperazin-2-yl)-N-(thiophen-2-ylmethyl)acetamide | $C_{39}H_{40}Cl_2N_4O_4$ 699.2505 | 699.2540 |

-continued
| Ex | Structure | Compound | HRMS (M + H)+: Calculated | Experimental |
|---|---|---|---|---|
| Ia.1.24 | 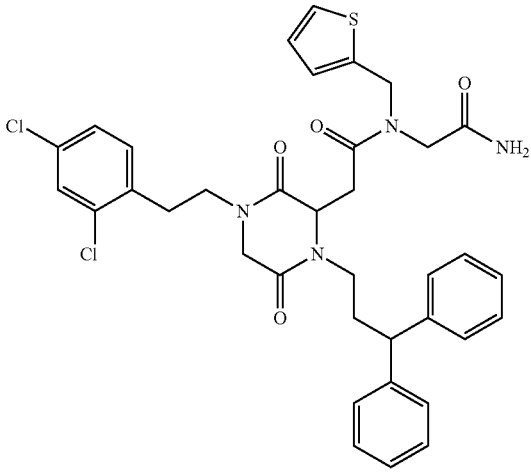 [SMILES: NC(=O)CN(Cc1cccs1)C(=O)CC1C(=O)N(CCc2ccc(Cl)cc2Cl)CC(=O)N1CCC(c1ccccc1)c1ccccc1] | N-(2-amino-2-oxoethyl)-N-(sec-butyl)-2-(4-(2,4-dichlorophenethyl)-1-(3,3-diphenylpropyl)-3,6-dioxopiperazin-2-yl)acetamide | $C_{36}H_{36}Cl_2N_4O_4S$ 691.1913 | 691.1913 |
| Ia.1.25 | 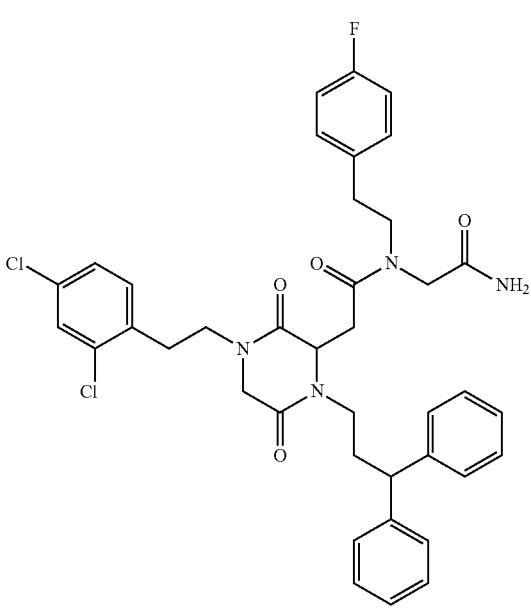 [SMILES: NC(=O)CN(CCc1ccc(F)cc1)C(=O)CC1C(=O)N(CCc2ccc(Cl)cc2Cl)CC(=O)N1CCC(c1ccccc1)c1ccccc1] | N-(2-amino-2-oxoethyl)-2-(4-(2,4-dichlorophenethyl)-1-(3,3-diphenylpropyl)-3,6-dioxopiperazin-2-yl)-N-((tetrahydrofuran-2-yl)methyl)acetamide | $C_{39}H_{39}Cl_2FN_4O_4$ 717.2411 | 717.2441 |

-continued

| Ex | Structure | Compound | HRMS (M + H)+: Calculated | Experimental |
|---|---|---|---|---|
| Ia.6.2 | 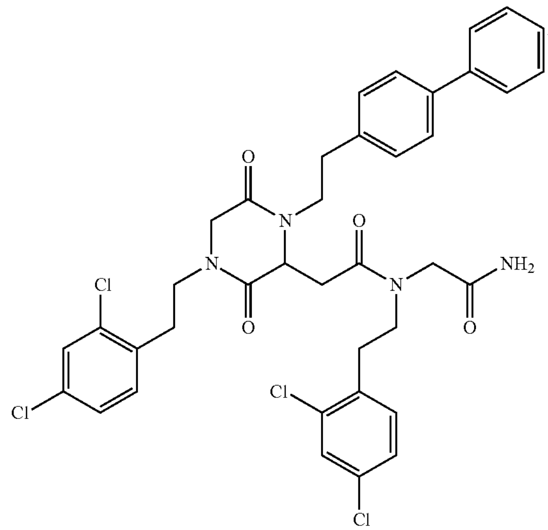 [SMILES: NC(=O)CN(CCc1ccc(Cl)cc1Cl)C(=O)CC1C(=O)N(CCc2ccc(Cl)cc2Cl)CC(=O)N1CCc1ccc(-c2ccccc2)cc1] | 2-(1-(2-([1,1'-biphenyl]-4-yl)ethyl)-4-(2,4-dichlorophenethyl)-3,6-dioxopiperazin-2-yl)-N-(2-amino-2-oxoethyl)-N-(2,4-dichlorophenethyl)acetamide | $C_{38}H_{36}Cl_4N_4O_4$ 753.1569 | 753.4000 |
| Ia.7.2 | 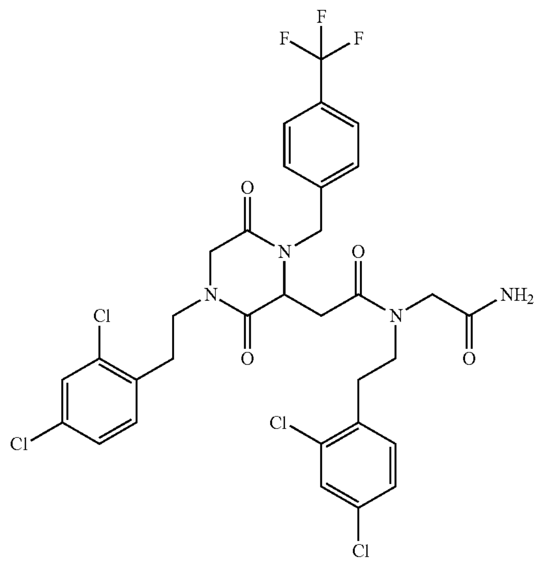 [SMILES: NC(=O)CN(CCc1ccc(Cl)cc1Cl)C(=O)CC1C(=O)N(CCc2ccc(Cl)cc2Cl)CC(=O)N1Cc1ccc(C(F)(F)F)cc1] | N-(2-amino-2-oxoethyl)-N-(2,4-dichlorophenethyl)-2-(4-(2,4-dichlorophenethyl)-3,6-dioxo-1-(4-(trifluoromethyl)benzyl)piperazin-2-yl)acetamide | $C_{32}H_{29}Cl_4F_3N_4O_4$ 731.0973 | 731.0995 |
| Ia.20.2 | 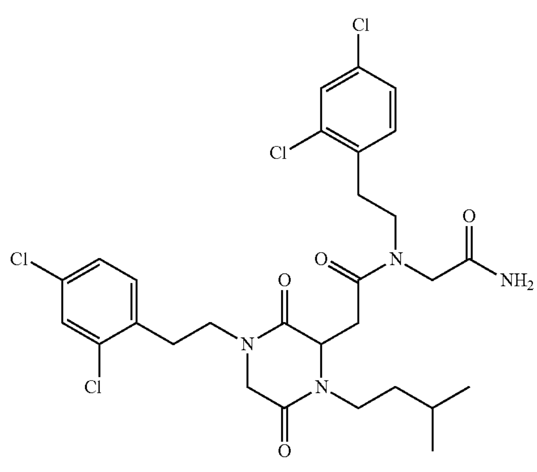 [SMILES: CC(C)CCN1C(=O)CN(CCc2ccc(Cl)cc2Cl)C(=O)C1CC(=O)N(CCc1ccc(Cl)cc1Cl)CC(N)=O] | N-(2-amino-2-oxoethyl)-N-(2,4-dichlorophenethyl)-2-(4-(2,4-dichlorophenethyl)-1-isopentyl-3,6-dioxopiperazin-2-yl)acetamide | $C_{29}H_{34}Cl_4N_4O_4$ 643.1412 | 643.1398 |

-continued

| Ex | Structure | Compound | HRMS (M + H)+: Calculated | Experimental |
|---|---|---|---|---|
| Ia.21.2 | 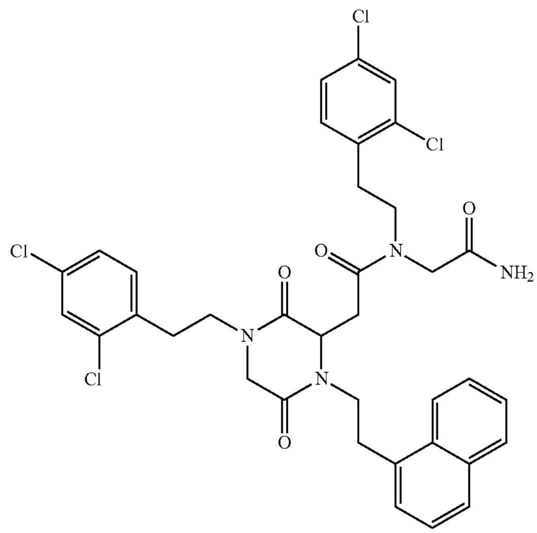 [SMILES: NC(=O)CN(CCc1ccc(Cl)cc1Cl)C(=O)CC1C(=O)N(CCc2ccc(Cl)cc2Cl)CC(=O)N1CCc1cccc2ccccc12] | N-(2-amino-2-oxoethyl)-N-(2,4-dichlorophenethyl)-2-(4-(2,4-dichlorophenethyl)-1-(2-(naphthalen-1-yl)ethyl)-3,6-dioxopiperazin-2-yl)acetamide | $C_{36}H_{34}Cl_4N_4O_4$ 727.1412 | 727.1428 |
| Ia.23.2 | 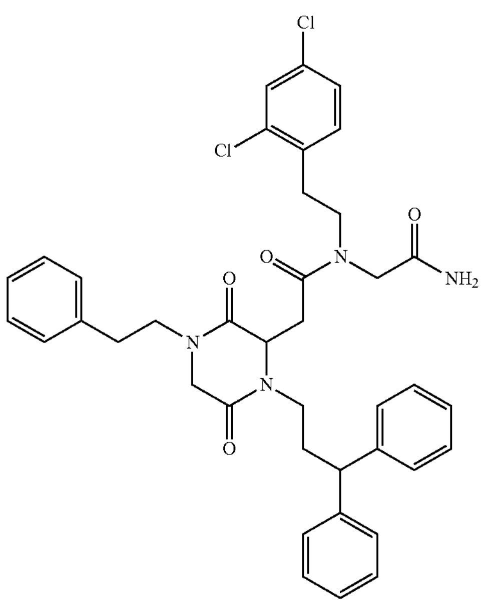 [SMILES: NC(=O)CN(CCc1ccc(Cl)cc1Cl)C(=O)CC1C(=O)N(CCc2ccccc2)CC(=O)N1CCC(c1ccccc1)c1ccccc1] | N-(2-amino-2-oxoethyl)-N-(2,4-dichlorophenethyl)-2-(1-(3,3-diphenylpropyl)-3,6-dioxo-4-phenethylpiperazin-2-yl)acetamide | $C_{39}H_{40}Cl_2N_4O_4$ 699.2505 | 699.2509 |

-continued
| Ex | Structure | Compound | HRMS (M + H)+: Calculated | Experimental |
|---|---|---|---|---|
| Ia.24.2 | 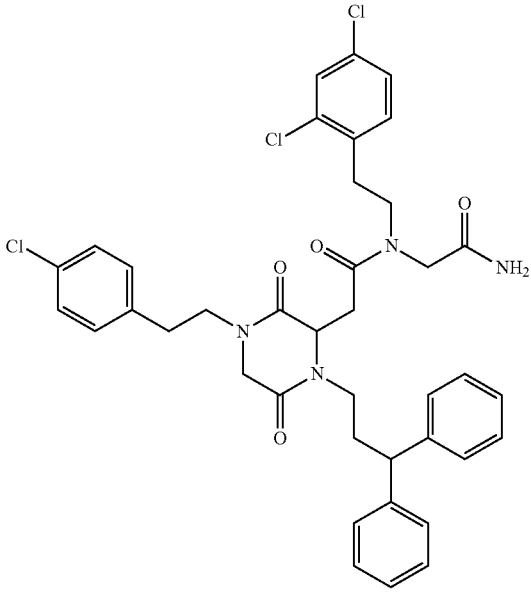 | N-(2-amino-2-oxoethyl)-2-(4-(4-chlorophenethyl)-1-(3,3-diphenylpropyl)-3,6-dioxopiperazin-2-yl)-N-(2,4-dichlorophenethyl)acetamide | $C_{39}H_{39}Cl_3N_4O_4$ 733.2115 | 755.1927 (Na+) |
| Ia.25.2 | 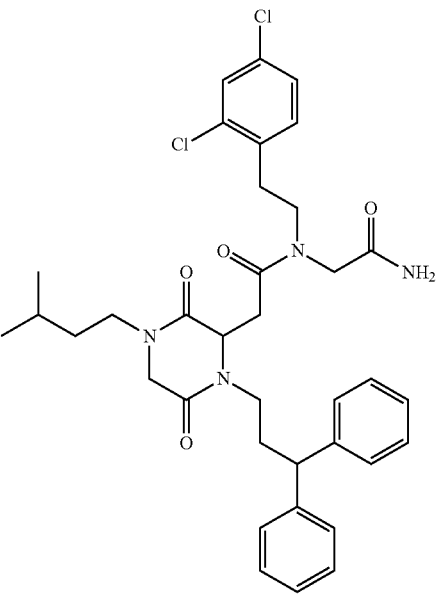 [SMILES: CC(C)CCN1CC(=O)N(CCC(c2ccccc2)c2ccccc2)C(CC(=O)N(CCc2ccc(Cl)cc2Cl)CC(N)=O)C1=O] | N-(2-amino-2-oxoethyl)-N-(2,4-dichlorophenethyl)-2-(1-(3,3-diphenylpropyl)-4-isopentyl-3,6-dioxopiperazin-2-yl)acetamide | $C_{36}H_{42}Cl_2N_4O_4$ 665.2661 | 665.2656 |

| Ex | Structure | Compound | HRMS (M + H)+: Calculated | Experimental |
|---|---|---|---|---|
| Ia.26.2 | | N-(2-amino-2-oxoethyl)-N-(2,4-dichlorophenethyl)-2-(4-(2,4-dichlorophenethyl)-1-(2,2-diphenylethyl)-3,6-dioxopiperazin-2-yl)acetamide | $C_{38}H_{36}Cl_4N_4O_4$ 753.1569 | 753.1569 | b) Ia.2.1: N-(2-amino-2-oxoethyl)-N-(2,4-dichlorophenethyl)-2-(4-(2,4-dichlorophenethyl)-1-(4-fluorobenzyl)-3,6-dioxopiperazin-2-yl)acetamide

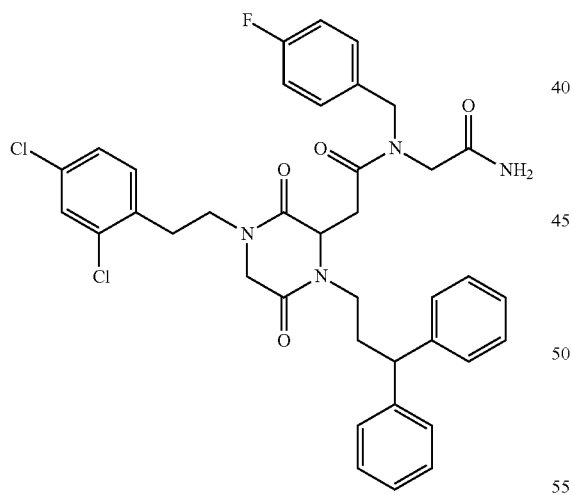

The acid X.2 (100 mg, 1 eq.) was added to a solution of 2-(4-fluorobenzylamino)acetamide (IVc, 28 μL, 1 eq.), DIC (85 μL, 3 eq.) and triethylamine (80 μL, 3 eq.) in 2 ml of DCM and the reaction mixture was stirred at room temperature for 3 h. The crude reaction product was neutralized with NaOH and was extracted with DCM. The organic extracts were washed with saturated sodium chloride, they were dried on anhydrous MgSO$_4$ and were evaporated at reduced pressure to obtain 96 mg of the desired compound Ia.2.1.
Method A: tr:13.239, m/z: 681

The following intermediates were prepared in the manner similar to compound 1a.2.1:

| Ex | Structure | Compound | method | tr | m/z |
|---|---|---|---|---|---|
| Ia.3.2 | 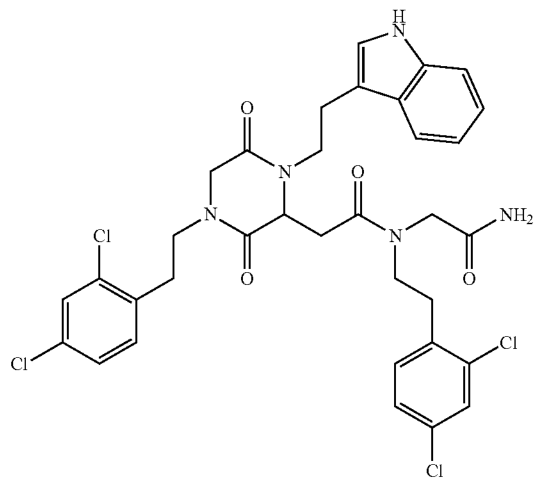 [SMILES: NC(=O)CN(CCc1ccc(Cl)cc1Cl)C(=O)CC1C(=O)N(CCc2ccc(Cl)cc2Cl)CC(=O)N1CCc1c[nH]c2ccccc12] | 2-(1-(2-(1H-indol-3-yl)ethyl)-4-(2,4-dichlorophenethyl)-3,6-dioxopiperazin-2-yl)-N-(2-amino-2-oxoethyl)-N-(2,4-dichlorophenthyl)acetamide | A | 13.961 | — |
| Ia.4.2 | 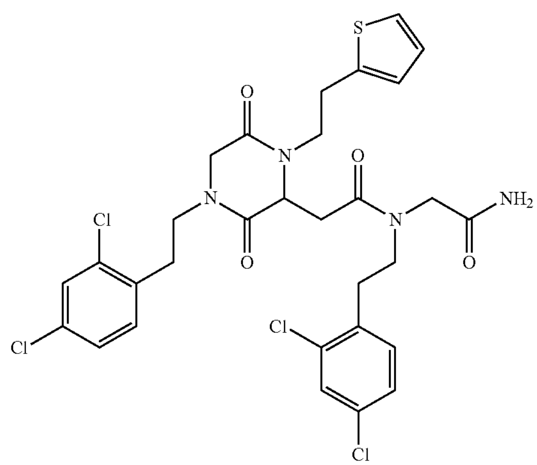 [SMILES: NC(=O)CN(CCc1ccc(Cl)cc1Cl)C(=O)CC1C(=O)N(CCc2ccc(Cl)cc2Cl)CC(=O)N1CCc1cccs1] | N-(2-amino-2-oxoethyl)-N-(2,4-dichlorophenethyl)-2-(4-(2,4-dichlorophenethyl)-3,6-dioxo-1-(2-(thiophen-2-yl)ethyl)piperazin-2-yl)acetamide | A | 13.228 | 683 |
| Ia.11.19 | 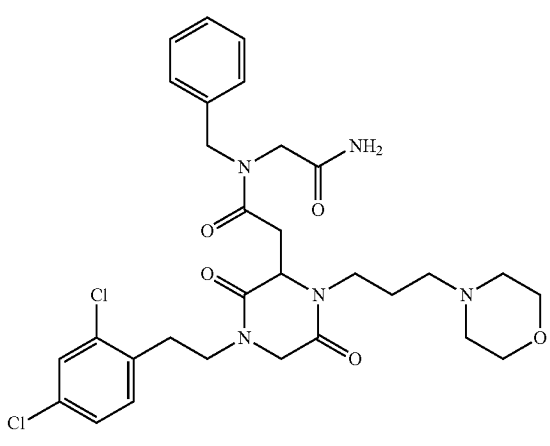 [SMILES: NC(=O)CN(Cc1ccccc1)C(=O)CC1C(=O)N(CCc2ccc(Cl)cc2Cl)CC(=O)N1CCCN1CCOCC1] | N-(2-amino-2-oxoethyl)-N-benzyl-2-(4-(2,4-dichlorophenethyl)-1-(3-morpholinopropyl)-3,6-dioxopiperazin-2-yl)acetamide | B | 2.786 | 618 620 |

Compounds of Formula Ib a) Ib.1.2 2-(N-(2,4-dichlorophenethyl)-2-(4-(2,4-dichlorophenethyl)-1-(3,3-diphenylpropyl)-3,6-dioxopiperazin-2-yl)acetamido) acetic acid

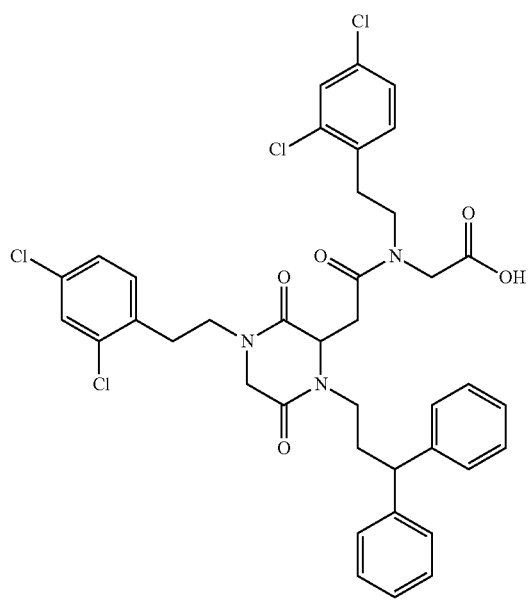 [SMILES: O=C(O)CN(CCc1ccc(Cl)cc1Cl)C(=O)CC1C(=O)N(CCc2ccc(Cl)cc2Cl)CC(=O)N1CCC(c1ccccc1)c1ccccc1]

A solution of bromoacetic acid (275 mg, 5 eq.) and DIPEA (345 μl, 5 eq.) in DMF (3 ml) was added to 200 mg of 2-chlorotrityl chloride resin (1.6 mmol/g Cl/g resin, 0.17 mmol) and the suspension was stirred at room temperature for 1 h. The resin was filtered and washed with DMF (3×3 ml), isopropyl alcohol (3×3 ml) and DCM (3×3 ml). The resin was then treated with methanol (3 ml) for 10 min to remove the unreacted Cl atoms. The supernatant was removed and the residue was washed with DCM (3×3 ml), isopropyl alcohol (3×3 ml) and DMF (3×3 ml). A solution of 2,4-dichlorophenethylamine (IVa, 340 5 eq.) and triethylamine (280 μL, 5 eq.) in 3 ml of DMF was then added to the resin and the suspension was stirred at room temperature for 3 h. After filtering and washing with DMF (3×3 ml), isopropyl alcohol (3×3 ml) and DCM (3×3 ml), acid X (100 mg, 1.1 eq.) was added to the resin in the presence of HOBT (40 mg, 1.5 eq.), HATU (105 mg, 1.5 eq.) and DIPEA (95 μL, 3 eq.) in 2:1 DCM:DMF (3 ml). The reaction mixture was stirred at room temperature for 16 h and was filtered. The resin was dried and washed with DMF (3×3 ml), isopropyl alcohol (3×3 ml) and DCM (3×3 ml). Finally, the resin was treated with a mixture of 5:95 TFA:DCM (5 ml) for 30 min at room temperature, obtaining a crude reaction product which was filtered. The solvent of the filtrate was removed at reduced pressure to obtain 60 mg of the desired compound (Ib.1.2, 42% yield, 91% purity). HRMS (M+H)$^+$ calculated for $C_{39}H_{38}Cl_4N_3O_5$, 768.1576, experimental, 768.1573.

| | | | HRMS (M + H)$^+$: | |
|---|---|---|---|---|
| Ex | Structure | Compound | Calculated | Experimental |
| Ib.2.2 | | 2-(N-(2,4-dichlorophenethyl)-2-(4-(2,4-dichlorophenethyl)-1-(4-fluorobenzyl)-3,6-dioxopiperazin-2-yl)acetamido) acetic acid | $C_{31}H_{28}Cl_4FN_3O_5$ 682.0845 | 682.0841 |

-continued

| Ex | Structure | Compound | HRMS (M + H)+: Calculated | Experimental |
|---|---|---|---|---|
| Ib.3.2 | 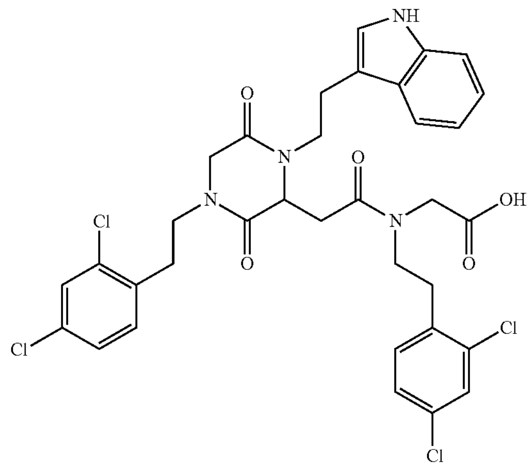 [SMILES: O=C(O)CN(CCc1ccc(Cl)cc1Cl)C(=O)CC1C(=O)N(CCc2ccc(Cl)cc2Cl)CC(=O)N1CCc1c[nH]c2ccccc12] | 2-(2-(1-(2-(1H-indol-3-yl)ethyl)-4-(2,4-dichlorophenethyl)-3,6-dioxopiperazin-2-yl)-N-(2,4-dichlorophenethyl)acetamido) acetic acid | $C_{34}H_{32}Cl_4N_4O_5$ 717.1205 | 717.1216 |
| Ib.7.2 | 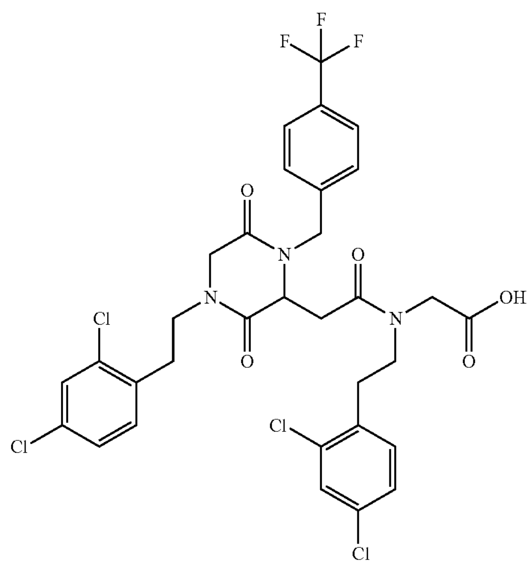 [SMILES: O=C(O)CN(CCc1ccc(Cl)cc1Cl)C(=O)CC1C(=O)N(CCc2ccc(Cl)cc2Cl)CC(=O)N1Cc1ccc(C(F)(F)F)cc1] | 2-(N-(2,4-dichlorophenethyl)-2-(4-(2,4-dichlorophenethyl)-3,6-dioxo-1-(4-(tri-fluoromethyl)benzyl)piperazin-2-yl)acetamido) acetic acid | $C_{32}H_{28}Cl_4F_3N_3O_5$ 732.0813 | 732.0827 |
| Ib.4.2 | 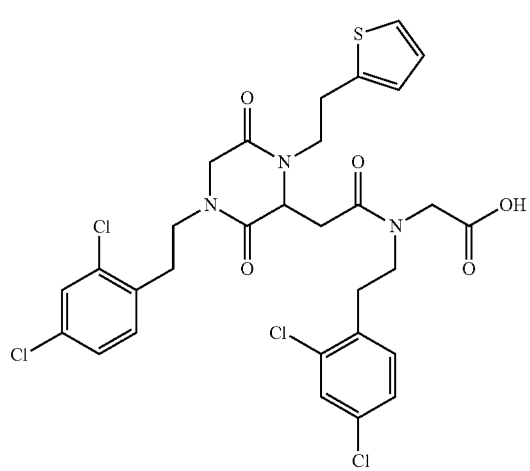 [SMILES: O=C(O)CN(CCc1ccc(Cl)cc1Cl)C(=O)CC1C(=O)N(CCc2ccc(Cl)cc2Cl)CC(=O)N1CCc1cccs1] | 2-(N-(2,4-dichlorophenethyl)-2-(4-(2,4-dichlorophenethyl)-3,6-dioxo-1-(2-(thiophen-2-yl)ethyl)piperazin-2-yl)acetamido) acetic acid | $C_{30}H_{29}Cl_4N_3O_5S$ 684.066 | 684.0661 |

-continued

| Ex | Structure | Compound | HRMS (M + H)+: Calculated | Experimental |
|---|---|---|---|---|
| Ib.5.2 | 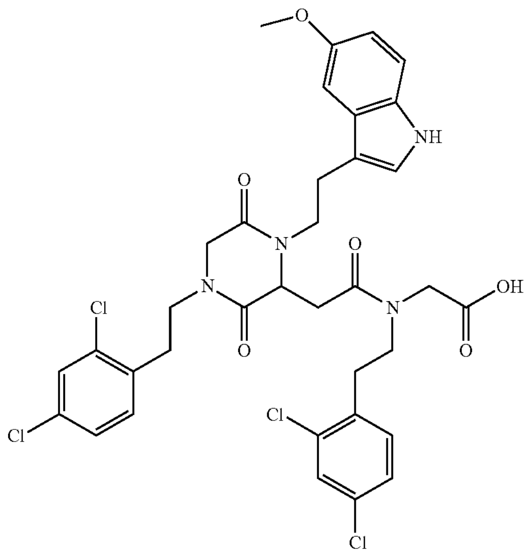 [SMILES: COc1ccc2[nH]cc(CCN3C(=O)CN(CCc4ccc(Cl)cc4Cl)C(=O)C3CC(=O)N(CCc3ccc(Cl)cc3Cl)CC(=O)O)c2c1] | 2-(N-(2,4-dichlorophenethyl)-2-(4-(2,4-dichlorophenethyl)-1-(2-(5-methoxy-1H-indol-3-yl)ethyl)-3,6-dioxopiperazin-2-yl)acetamido) acetic acid | $C_{35}H_{34}Cl_4N_4O_6$ 747.1311 | 747.1272 |
| Ib.6.2 | 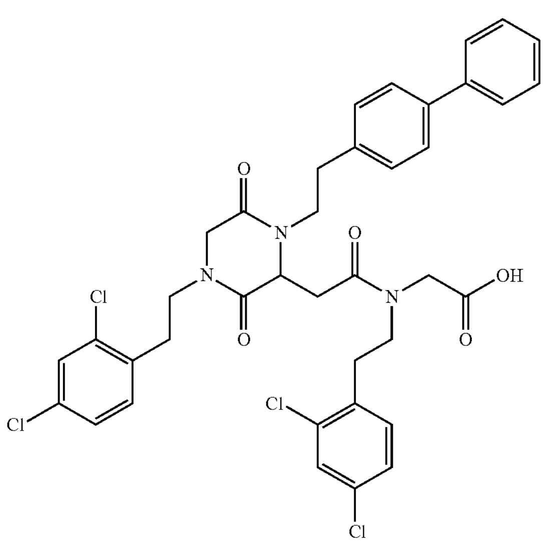 [SMILES: O=C(O)CN(CCc1ccc(Cl)cc1Cl)C(=O)CC1C(=O)N(CCc2ccc(Cl)cc2Cl)CC(=O)N1CCc1ccc(-c2ccccc2)cc1] | 2-(2-(1-(2-([1,1'-biphenyl]-4-yl)ethyl)-4-(2,4-dichlorophenethyl)-3,6-dioxopiperazin-2-yl)-N-(2,4-dichlorophenethyl)acetamido) acetic acid | $C_{38}H_{35}Cl_4N_3O_5$ 754.1409 | 754.1389 |

Compounds of formula Ic

Ic.1.2. Methyl 2-(N-(2,4-dichlorophenethyl)-2-(4-(2,4-dichlorophenethyl)-1-(3,3-diphenylpropyl)-3,6-dioxopiperazin-2-yl)acetamido)acetate

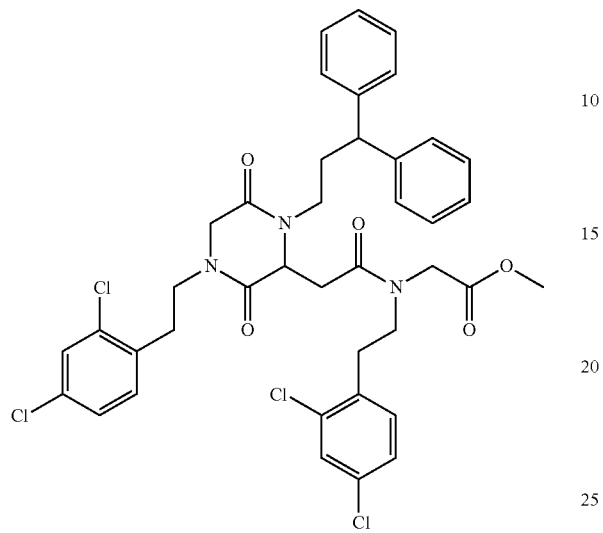

A mixture of acid Ib.1.2 (30 mg, 1 eq.), methanol (7.5 ml) and $H_2SO_4$ (20 μl, 1 eq.) was reacted for 15 h at room temperature. The crude reaction product was neutralized with NaOH and was extracted with DCM. The organic extracts were washed with saturated sodium chloride, dried on anhydrous $MgSO_4$ and evaporated at reduced pressure to obtain 22 mg of the desired compound Ic.1.2 (72% yield, 86% purity). HRMS (M+H)$^+$ calculated for $C_{40}H_{39}Cl_4N_3O_5$, 782.1722, experimental, 782.1216.

| Ex | Structure | Compound | HRMS (M + H)$^+$: Calculated | Experimental |
|---|---|---|---|---|
| Ic.2.2 | 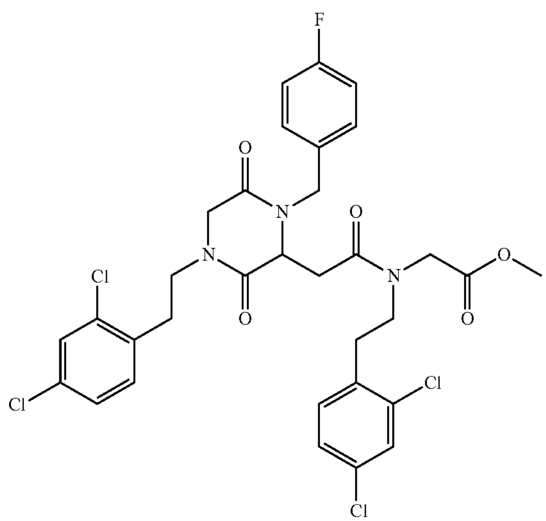 [SMILES: COC(=O)CN(CCc1ccc(Cl)cc1Cl)C(=O)CC1C(=O)N(CCc2ccc(Cl)cc2Cl)CC(=O)N1Cc1ccc(F)cc1] | Methyl 2-(N-(2,4-dichlorophenethyl)-2-(4-(2,4-dichlorophenethyl)-1-(4-fluorobenzyl)-3,6-dioxopiperazin-2-yl)acetamido)acetate | $C_{32}H_{30}Cl_4FN_3O_5$ 696.1002 | 696.1052 |

| | | | |
|---|---|---|---|
| Ic.3.2 | 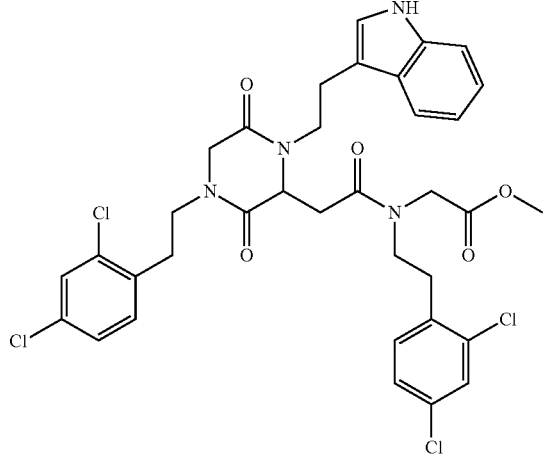 [SMILES: COC(=O)CN(CCc1ccc(Cl)cc1Cl)C(=O)CC1C(=O)N(CCc2ccc(Cl)cc2Cl)CC(=O)N1CCc1c[nH]c2ccccc12] | Methyl 2-(2-(1-(2-(1H-indol-3-yl)ethyl)-4-(2,4-dichlorophenethyl)-3,6-dioxopiperazin-2-yl)-N-(2,4-dichlorophenethyl)acetamido)acetate | $C_{35}H_{34}Cl_4N_4O_5$ 731.1362 731.1321 |
| Ic.4.2 | 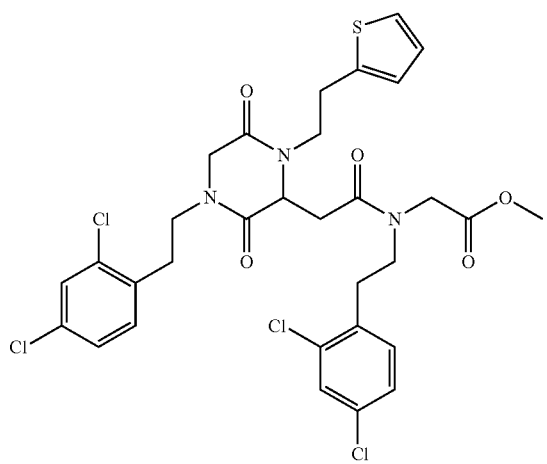 [SMILES: COC(=O)CN(CCc1ccc(Cl)cc1Cl)C(=O)CC1C(=O)N(CCc2ccc(Cl)cc2Cl)CC(=O)N1CCc1cccs1] | Methyl 2-(N-(2,4-dichlorophenethyl)-2-(4-(2,4-dichlorophenethyl)-3,6-dioxo-1-(2-(thiophen-2-yl)ethyl)piperazin-2-yl)acetamido)acetate | $C_{31}H_{31}Cl_4N_3O_5S$ 698.0817 698.0849 |
| Ic.5.2 | 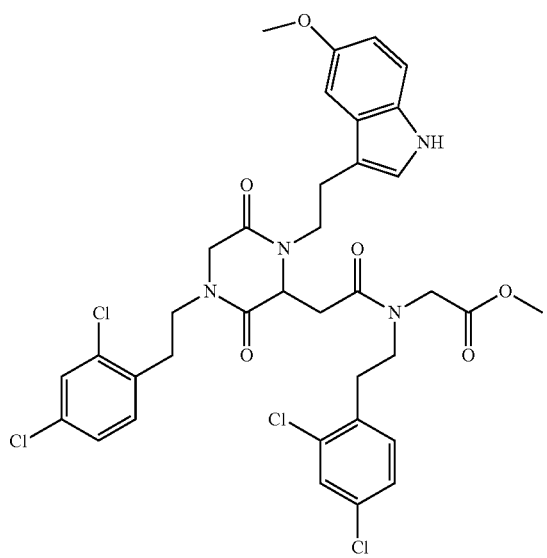 [SMILES: COC(=O)CN(CCc1ccc(Cl)cc1Cl)C(=O)CC1C(=O)N(CCc2ccc(Cl)cc2Cl)CC(=O)N1CCc1c[nH]c2ccc(OC)cc12] | Methyl 2-(N-(2,4-dichlorophenethyl)-2-(4-(2,4-dichlorophenethyl)-1-(2-(5-methoxy-1H-indol-3-yl)ethyl)-3,6-dioxopiperazin-2-yl)acetamido)acetate | $C_{36}H_{36}Cl_4N_4O_6$ 761.1467 761.1437 |

| Ex | Structure | Compound | | tr | m/z |
|---|---|---|---|---|---|
| Ic.6.2 | 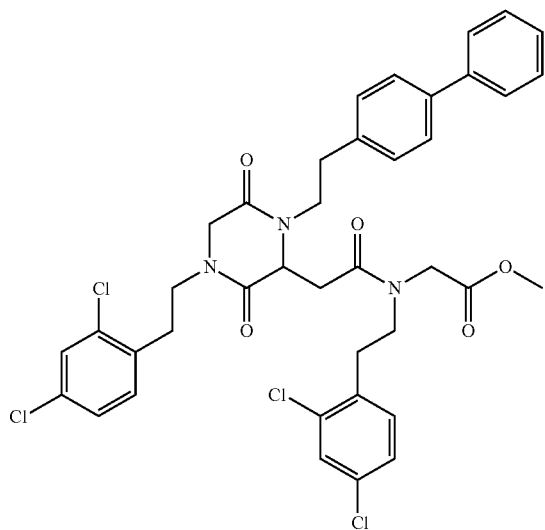 [SMILES: COC(=O)CN(CCc1ccc(Cl)cc1Cl)C(=O)CC1C(=O)N(CCc2ccc(Cl)cc2Cl)CC(=O)N1CCc1ccc(-c2ccccc2)cc1] | Methyl 2-(2-(1-(2-([1,1'-biphenyl]-4-yl)ethyl)-4-(2,4-dichlorophenethyl)-3,6-dioxo-piperazin-2-yl)-N-(2,4-dichlorophenethyl)acetamido)acetate | $C_{39}H_{37}Cl_4N_3O_5$ 768.1566 | | 768.1570 |
| Ic.7.2 | 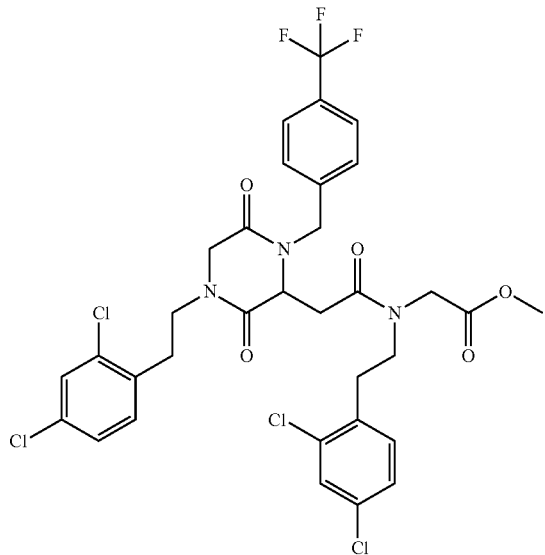 [SMILES: COC(=O)CN(CCc1ccc(Cl)cc1Cl)C(=O)CC1C(=O)N(CCc2ccc(Cl)cc2Cl)CC(=O)N1Cc1ccc(C(F)(F)F)cc1] | Methyl 2-(N-(2,4-dichlorophenethyl)-2-(4-(2,4-dichlorophenethyl)-3,6-dioxo-1-(4-(trifluoromethyl)benzyl)piperazin-2-yl)acetamido)acetate | $C_{33}H_{30}Cl_4F_3N_3O_5$ 746.097 | | 746.0955 |

| Ex | Structure | Compound | method | tr | m/z |
|---|---|---|---|---|---|
| Ic.4.3 | 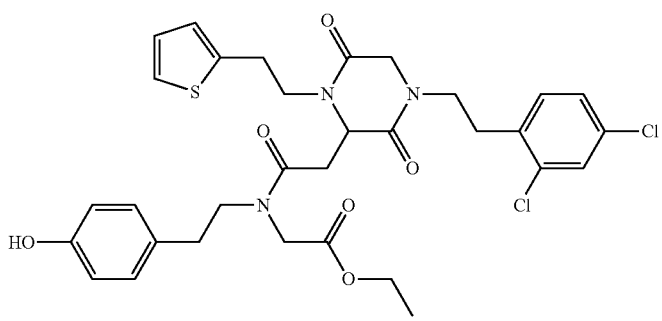 [SMILES: CCOC(=O)CN(CCc1ccc(O)cc1)C(=O)CC1C(=O)N(CCc2ccc(Cl)cc2Cl)CC(=O)N1CCc1cccs1] | Ethyl 2-(2-(4-(2,4-dichlorophenethyl)-3,6-dioxo-1-(2-(thiophen-2-yl)ethyl)piperazin-2-yl)-N-(4-hydroxyphenethyl)acetamido)acetate | B | 3.374 | 660 662 |

| | | | | | |
|---|---|---|---|---|---|
| Ic.4.5 | 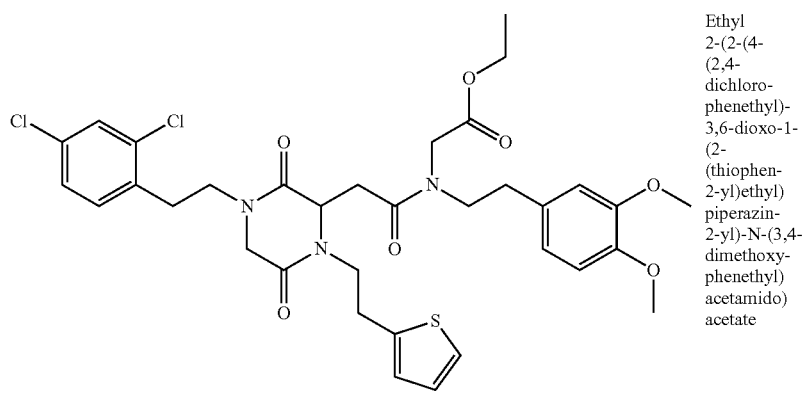 | Ethyl 2-(2-(4-(2,4-dichlorophenethyl)-3,6-dioxo-1-(2-(thiophen-2-yl)ethyl)piperazin-2-yl)-N-(3,4-dimethoxyphenethyl)acetamido)acetate | B | 4.349 | 704 706 |
| Ic.4.6 | 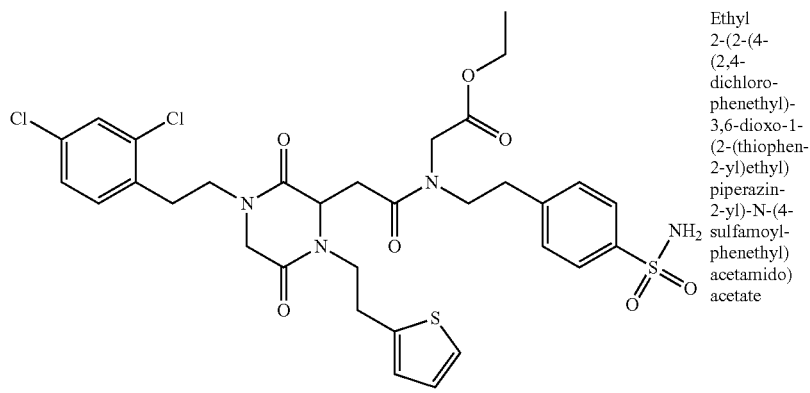 | Ethyl 2-(2-(4-(2,4-dichlorophenethyl)-3,6-dioxo-1-(2-(thiophen-2-yl)ethyl)piperazin-2-yl)-N-(4-sulfamoylphenethyl)acetamido)acetate | B | 3.950 | 723 725 |
| Ic.4.7 | 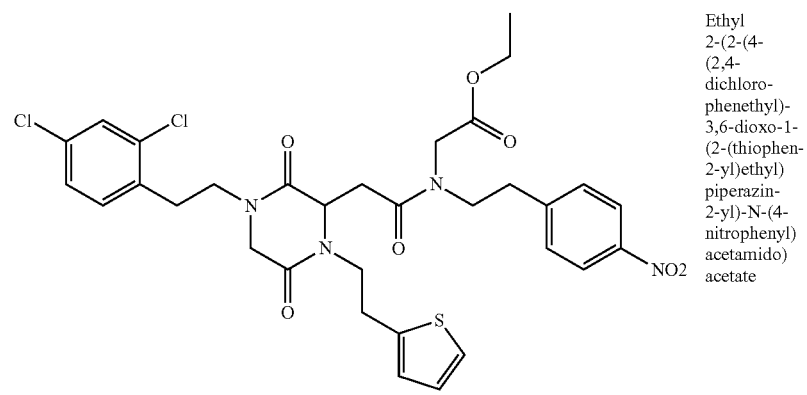 | Ethyl 2-(2-(4-(2,4-dichlorophenethyl)-3,6-dioxo-1-(2-(thiophen-2-yl)ethyl)piperazin-2-yl)-N-(4-nitrophenyl)acetamido)acetate | B | 4.476 | 689 691 |
| Ic.4.8 | 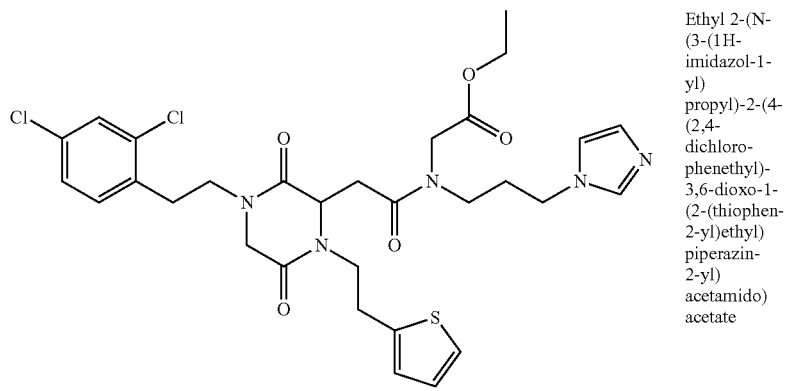 | Ethyl 2-(N-(3-(1H-imidazol-1-yl)propyl)-2-(4-(2,4-dichlorophenethyl)-3,6-dioxo-1-(2-(thiophen-2-yl)ethyl)piperazin-2-yl)acetamido)acetate | B | 3.174 | 648 650 |

| | | | | | |
|---|---|---|---|---|---|
| Ic.4.9 | 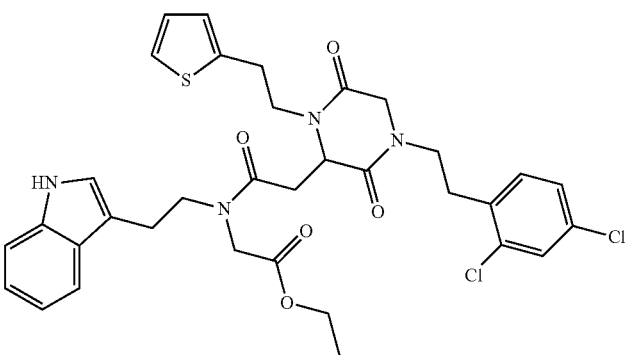 [SMILES: CCOC(=O)CN(CCc1c[nH]c2ccccc12)C(=O)CC1C(=O)N(CCc2ccc(Cl)cc2Cl)CC(=O)N1CCc1cccs1] | Ethyl 2-(N-(2-(1H-indol-3-yl)ethyl)-2-(4-(2,4-dichloro-phenethyl)-3,6-dioxo-1-(2-(thiophen-2-yl)ethyl) piperazin-2-yl) acetamido) acetate | B | 4.426 | 683 685 |
| Ic.4.11 | 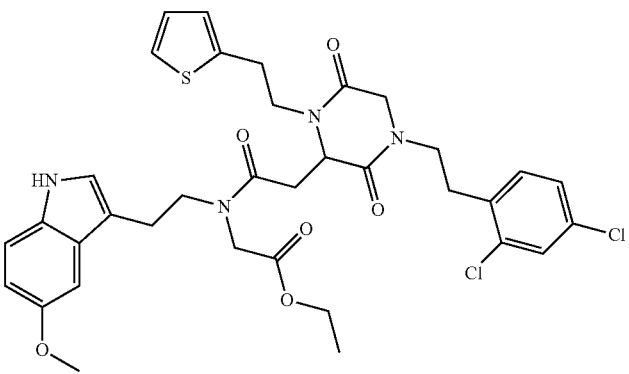 [SMILES: CCOC(=O)CN(CCc1c[nH]c2ccc(OC)cc12)C(=O)CC1C(=O)N(CCc2ccc(Cl)cc2Cl)CC(=O)N1CCc1cccs1] | Ethyl 2-(2-(4-(2,4-dichloro-phenethyl)-3,6-dioxo-1-(2-(thiophen-2-yl)ethyl) piperazin-2-yl)-N-(2-(5-methoxy-1H-indol-3-yl)ethyl) acetamido) acetate | B | 4.348 | 713 715 |
| Ic.4.12 | 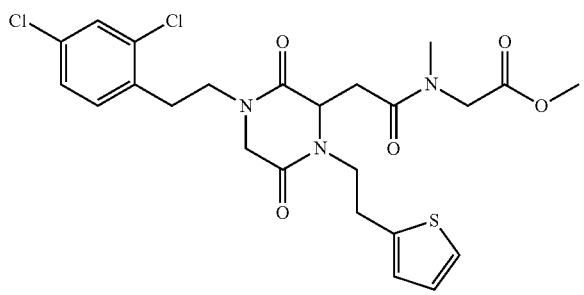 [SMILES: COC(=O)CN(C)C(=O)CC1C(=O)N(CCc2ccc(Cl)cc2Cl)CC(=O)N1CCc1cccs1] | Methyl 2-(2-(4-(2,4-dichloro-phenethyl)-3,6-dioxo-1-(2-(thiophen-2-yl)ethyl) piperazin-2-yl)-N-methyl-acetamido) acetate | B | 3.795 | 540 542 |
| Ic.4.13 | 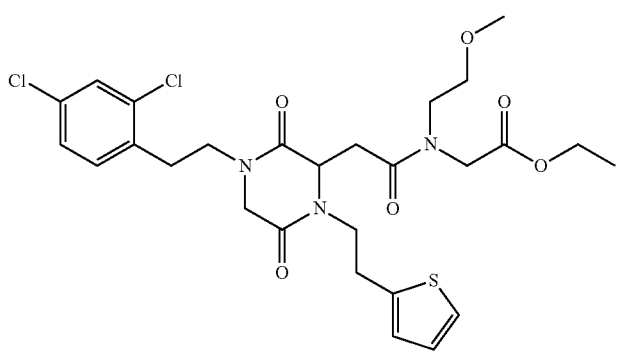 [SMILES: CCOC(=O)CN(CCOC)C(=O)CC1C(=O)N(CCc2ccc(Cl)cc2Cl)CC(=O)N1CCc1cccs1] | Ethyl 2-(2-(4-(2,4-dichloro-phenethyl)-3,6-dioxo-1-(2-(thiophen-2-yl)ethyl) piperazin-2-yl)-N-(2-methoxy-ethyl) acetamido) acetate | B | 4.104 | 598 600 |

| | | | | | |
|---|---|---|---|---|---|
| Ic.4.14 | 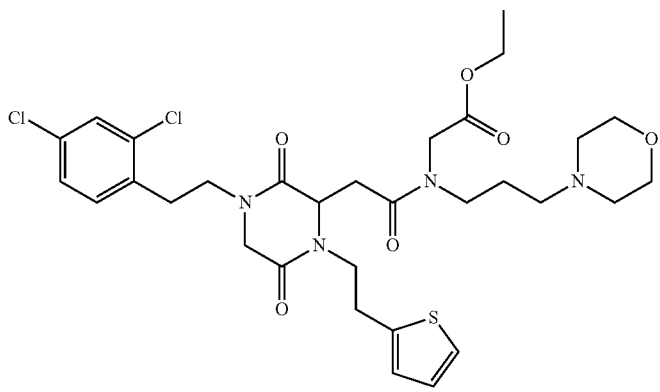 [SMILES: CCOC(=O)CN(CCCN1CCOCC1)C(=O)CC1C(=O)N(CCc2ccc(Cl)cc2Cl)CC(=O)N1CCc1cccs1] | Ethyl 2-(2-(4-(2,4-dichloro-phenethyl)-3,6-dioxo-1-(2-(thio-phen-2-yl)ethyl)piperazin-2-yl)-N-(3-morpholino-propyl)acetamido)acetate | B | 3.183 | 667 669 |
| Ic.4.15 | 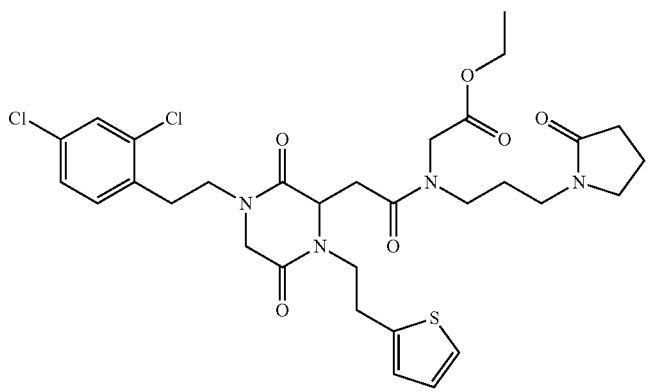 [SMILES: CCOC(=O)CN(CCCN1CCCC1=O)C(=O)CC1C(=O)N(CCc2ccc(Cl)cc2Cl)CC(=O)N1CCc1cccs1] | Ethyl 2-(2-(4-(2,4-dichloro-phenethyl)-3,6-dioxo-1-(2-(thiophen-2-yl)ethyl)piperazin-2-yl)-N-(3-(2-oxo-pyrrolidin-1-yl)propyl)acetamido)acetate | B | 3.813 | 665 667 |
| Ic.8.1 | 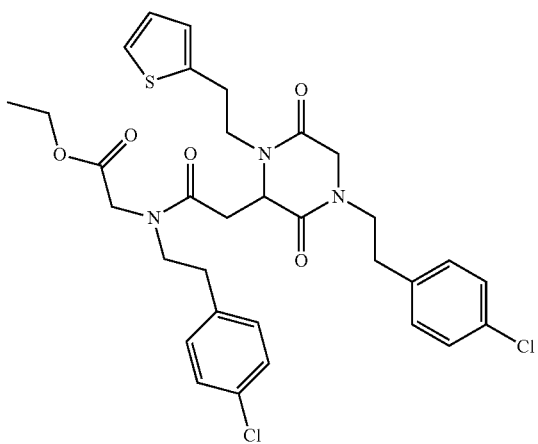 [SMILES: CCOC(=O)CN(CCc1ccc(Cl)cc1)C(=O)CC1C(=O)N(CCc2ccc(Cl)cc2)CC(=O)N1CCc1cccs1] | Ethyl 2-(N-(4-chloro-phenethyl)-2-(4-(4-chloro-phenethyl)-3,6-di-oxo-1-(2-(thiophen-2-yl)ethyl)piperazin-2-yl)acetamido)acetate | B | 4.520 | 644 646 |
| Ic.8.3 | 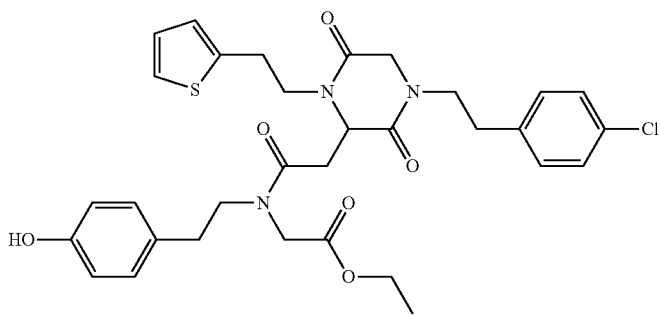 [SMILES: CCOC(=O)CN(CCc1ccc(O)cc1)C(=O)CC1C(=O)N(CCc2ccc(Cl)cc2)CC(=O)N1CCc1cccs1] | Ethyl 2-(2-(4-(4-chloro-phenethyl)-3,6-dioxo-1-(2-(thiophen-2-yl)ethyl)piperazin-2-yl)-N-(4-hydroxy-phenethyl)acetamido)acetate | B | 3.844 | 626 628 |

| | | | | | |
|---|---|---|---|---|---|
| Ic.8.4 | 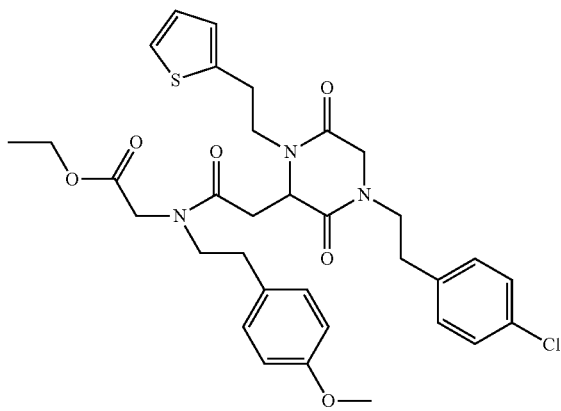 [SMILES: CCOC(=O)CN(CCc1ccc(OC)cc1)C(=O)CC1C(=O)N(CCc2ccc(Cl)cc2)CC(=O)N1CCc1cccs1] | Ethyl 2-(2-(4-(4-chloro-phenethyl)-3,6-dioxo-1-(2-(thiophen-2-yl)ethyl)piperazin-2-yl)-N-(4-methoxy-phenethyl)acetamido)acetate | B | 4.299 | 391 |
| Ic.8.5 | 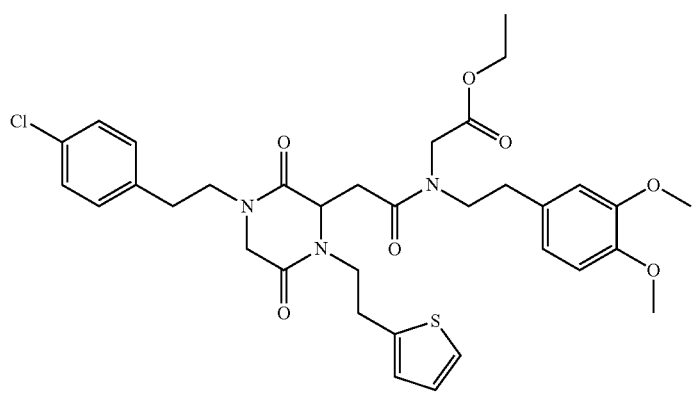 [SMILES: CCOC(=O)CN(CCc1ccc(OC)c(OC)c1)C(=O)CC1C(=O)N(CCc2ccc(Cl)cc2)CC(=O)N1CCc1cccs1] | Ethyl 2-(2-(4-(4-chloro-phenethyl)-3,6-dioxo-1-(2-(thiophen-2-yl)ethyl)piperazin-2-yl)-N-(3,4-di-methoxy-phenethyl)acetamido)acetate | B | 4.126 | 670 672 |
| Ic.8.6 | 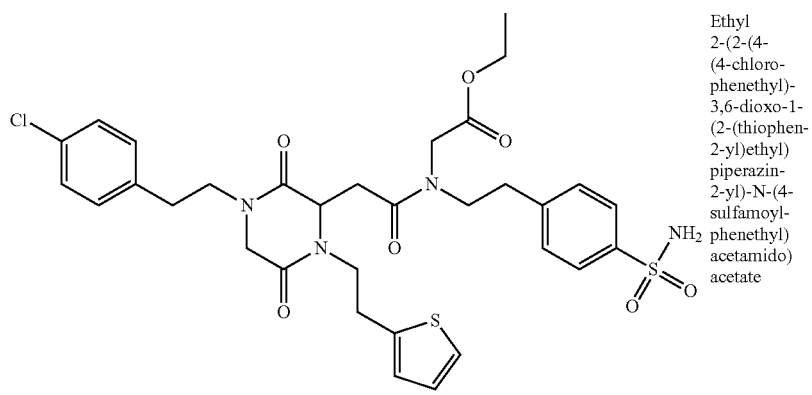 | Ethyl 2-(2-(4-(4-chloro-phenethyl)-3,6-dioxo-1-(2-(thiophen-2-yl)ethyl)piperazin-2-yl)-N-(4-sulfamoyl-phenethyl)acetamido)acetate | B | 3.736 | 689 691 |
| Ic.8.8 | 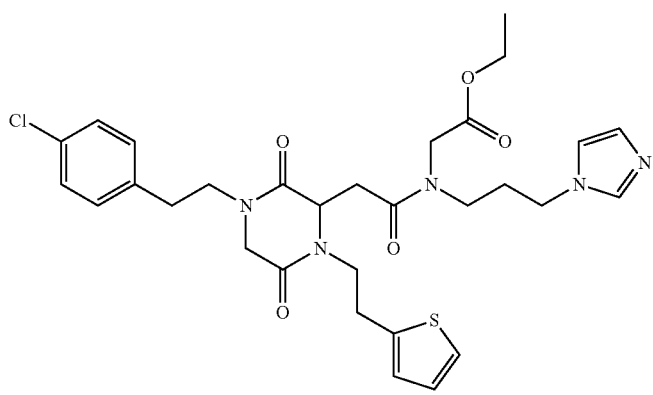 [SMILES: CCOC(=O)CN(CCCn1ccnc1)C(=O)CC1C(=O)N(CCc2ccc(Cl)cc2)CC(=O)N1CCc1cccs1] | Ethyl 2-(N-(3-(1H-imidazol-1-yl)propyl)-2-(4-(4-chloro-phenethyl)-3,6-dioxo-1-(2-(thio-phen-2-yl)ethyl)piperazin-2-yl)acetamido)acetate | B | 2.993 | 614 616 |

| | | | | | |
|---|---|---|---|---|---|
| Ic.8.9 | 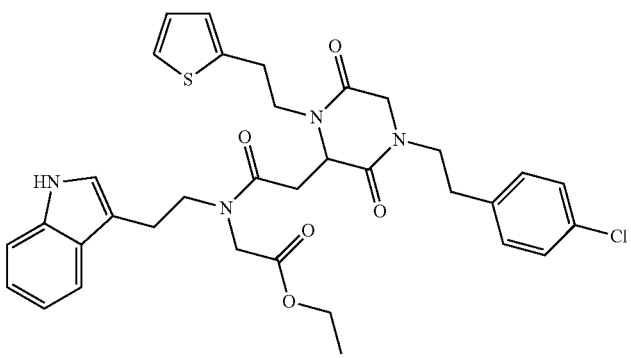 [SMILES: CCOC(=O)CN(CCc1c[nH]c2ccccc12)C(=O)CC1C(=O)N(CCc2ccc(Cl)cc2)CC(=O)N1CCc1cccs1] | Ethyl 2-(N-(2-(1H-indol-3-yl)ethyl)-2-(4-(4-chloro-phenethyl)-3,6-dioxo-1-(2-(thiophen-2-yl)ethyl) piperazin-2-yl)acetamido) acetate | B | 4.210 | 649 651 |
| Ic.8.11 | 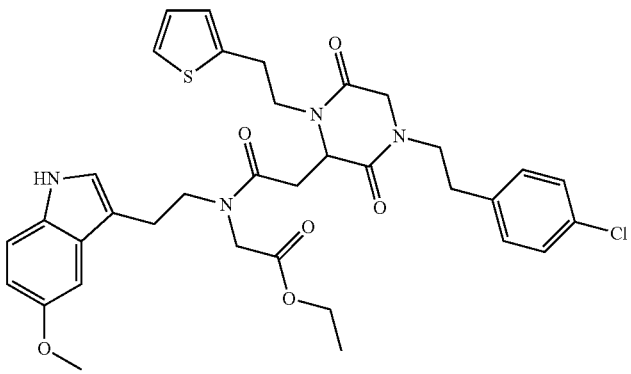 [SMILES: CCOC(=O)CN(CCc1c[nH]c2ccc(OC)cc12)C(=O)CC1C(=O)N(CCc2ccc(Cl)cc2)CC(=O)N1CCc1cccs1] | Ethyl 2-(2-(4-(4-chloro-phenethyl)-3,6-dioxo-1-(2-(thiophen-2-yl)ethyl) piperazin-2-yl)-N-(2-(5-methoxy-1H-indol-3-yl)ethyl) acetamido) acetate | B | 4.131 | 679 681 |
| Ic.8.12 | 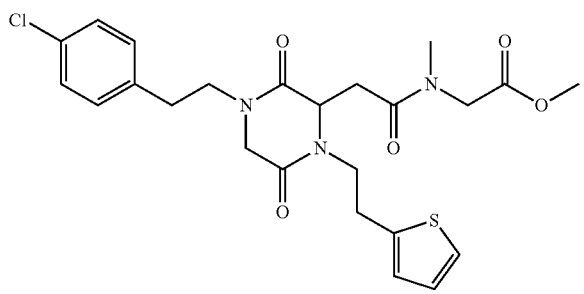 [SMILES: COC(=O)CN(C)C(=O)CC1C(=O)N(CCc2ccc(Cl)cc2)CC(=O)N1CCc1cccs1] | Methyl 2-(2-(4-(4-chloro-phenethyl)-3,6-dioxo-1-(2-(thiophen-2-yl)ethyl) piperazin-2-yl)-N-methyl-acetamido) acetate | B | 3.540 | 506 508 |
| Ic.8.13 | 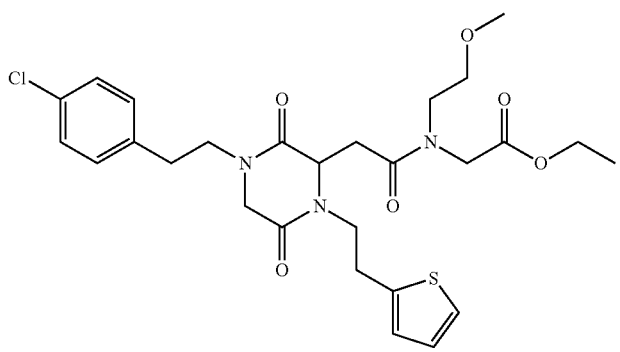 [SMILES: CCOC(=O)CN(CCOC)C(=O)CC1C(=O)N(CCc2ccc(Cl)cc2)CC(=O)N1CCc1cccs1] | Ethyl 2-(2-(4-(4-chloro-phenethyl)-3,6-dioxo-1-(2-(thiophen-2-yl)ethyl) piperazin-2-yl)-N-(2-methoxy-ethyl) acetamido) acetate | B | 3.855 | 564 566 |

| | | | | | |
|---|---|---|---|---|---|
| Ic.8.14 | 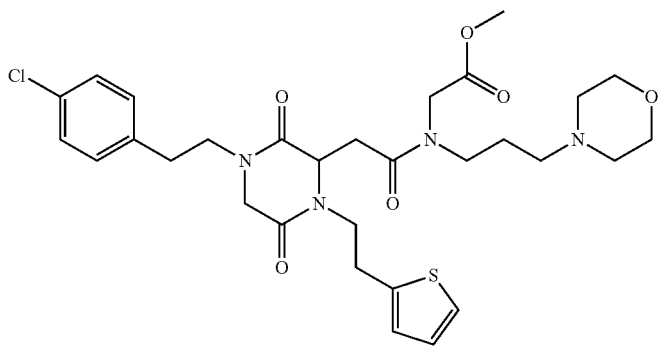 [SMILES: COC(=O)CN(CCCN1CCOCC1)C(=O)CC1C(=O)N(CCc2ccc(Cl)cc2)CC(=O)N1CCc1cccs1] | Ethyl 2-(2-(4-(4-chloro-phenethyl)-3,6-dioxo-1-(2-(thiophen-2-yl)ethyl)piperazin-2-yl)-N-(3-morpholino-propyl)acetamido)acetate | B | 2.992 | 633 635 |
| Ic.8.15 | 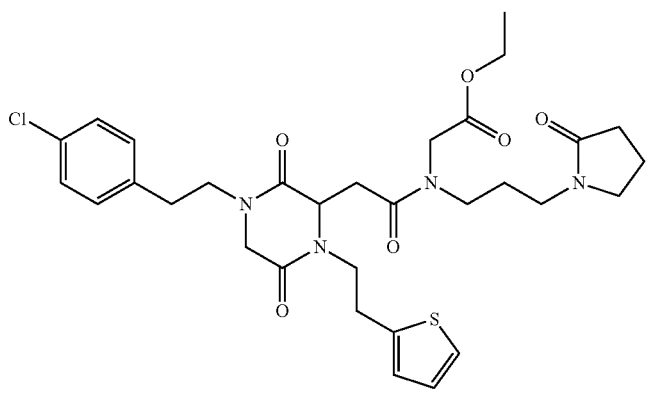 [SMILES: CCOC(=O)CN(CCCN1CCCC1=O)C(=O)CC1C(=O)N(CCc2ccc(Cl)cc2)CC(=O)N1CCc1cccs1] | Ethyl 2-(2-(4-(4-chloro-phenethyl)-3,6-dioxo-1-(2-(thiophen-2-yl)ethyl)piperazin-2-yl)-N-(3-(2-oxo-pyrrolidin-1-yl)propyl)acetamido)acetate | B | 3.585 | 631 633 |
| Ic.9.1 | 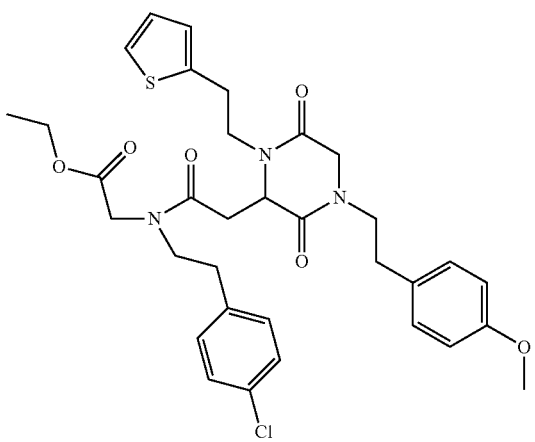 [SMILES: CCOC(=O)CN(CCc1ccc(Cl)cc1)C(=O)CC1C(=O)N(CCc2ccc(OC)cc2)CC(=O)N1CCc1cccs1] | Ethyl 2-(N-(4-chloro-phenethyl)-2-(4-(4-methoxy-phenethyl)-3,6-dioxo-1-(2-(thio-phen-2-yl)ethyl)piperazin-2-yl)acetamido)acetate | B | 4.297 | 640 642 |
| Ic.9.2 | 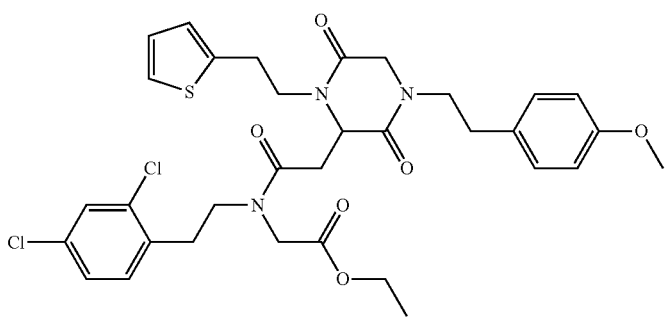 [SMILES: CCOC(=O)CN(CCc1ccc(Cl)cc1Cl)C(=O)CC1C(=O)N(CCc2ccc(OC)cc2)CC(=O)N1CCc1cccs1] | Ethyl 2-(N-(2,4-dichloro-phenethyl)-2-(4-(4-methoxy-phenethyl)-3,6-dioxo-1-(2-(thiophen-2-yl)ethyl)piperazin-2-yl)acetamido)acetate | B | 4.504 | 674 676 |

| | | | | | |
|---|---|---|---|---|---|
| Ic.9.3 | 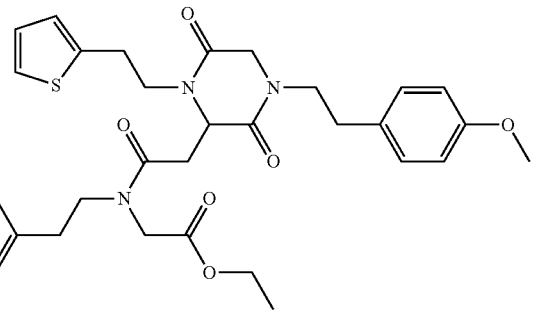 | Ethyl 2-(N-(4-hydroxy-phenethyl)-2-(4-(4-methoxy-phenethyl)-3,6-dioxo-1-(2-(thiophen-2-yl)ethyl)piperazin-2-yl)acetamido)acetate | B | 3.590 | 622 |
| Ic.9.4 | 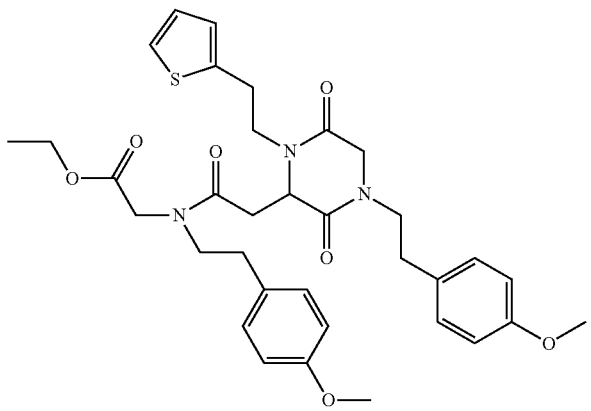 [SMILES: CCOC(=O)CN(CCc1ccc(OC)cc1)C(=O)CC1C(=O)N(CCc2ccc(OC)cc2)CC(=O)N1CCc1cccs1] | Ethyl 2-(N-(4-methoxy-phenethyl)-2-(4-(4-methoxy-phenethyl)-3,6-dioxo-1-(2-(thiophen-2-yl)ethyl)piperazin-2-yl)acetamido)acetate | B | 4.052 | 636 |
| Ic.9.5 | 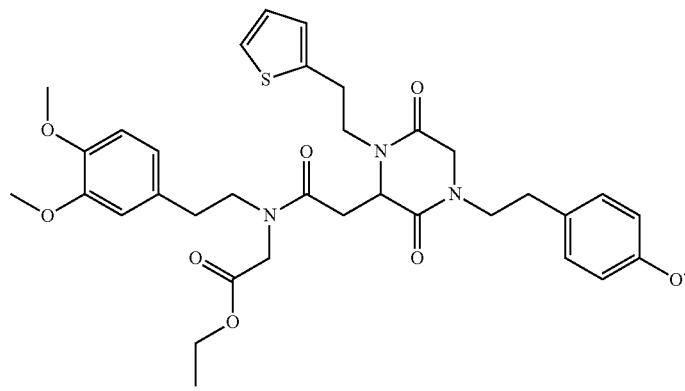 | Ethyl 2-(N-(3,4-dimethoxy-phenethyl)-2-(4-(4-methoxy-phenethyl)-3,6-dioxo-1-(2-(thiophen-2-yl)ethyl)piperazin-2-yl)acetamido)acetate | B | 3.870 | 666 |
| Ic.9.6 | 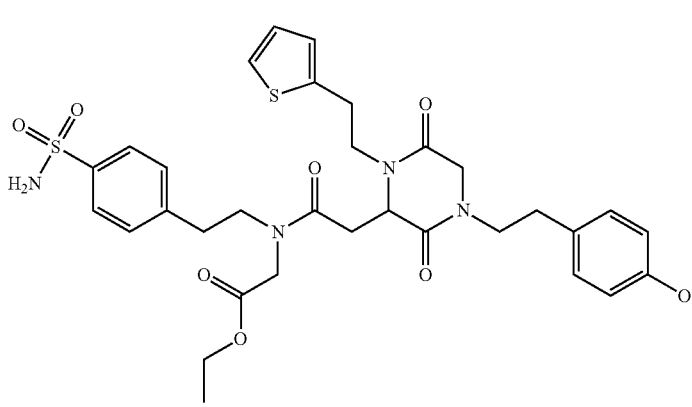 | Ethyl 2-(2-(4-(4-methoxy-phenethyl)-3,6-dioxo-1-(2-(thiophen-2-yl)ethyl)piperazin-2-yl)-N-(4-sulfamoyl-phenethyl)acetamido)acetate | B | 3.486 | 685 |

-continued

| | | | | | |
|---|---|---|---|---|---|
| Ic.9.7 | 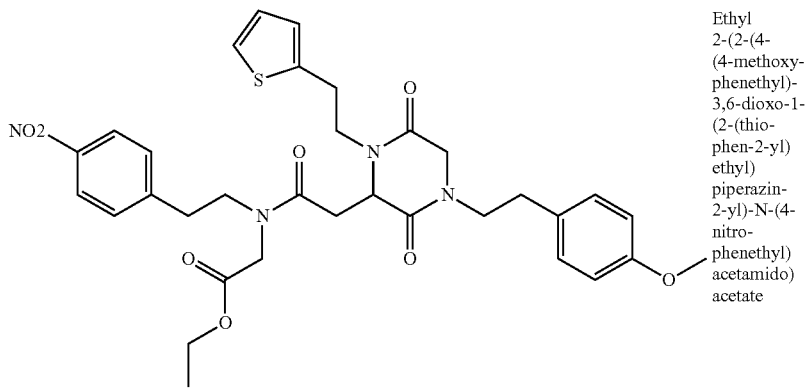 | Ethyl 2-(2-(4-(4-methoxyphenethyl)-3,6-dioxo-1-(2-(thiophen-2-yl)ethyl)piperazin-2-yl)-N-(4-nitrophenethyl)acetamido)acetate | B | 4.026 | 651 |
| Ic.9.8 | 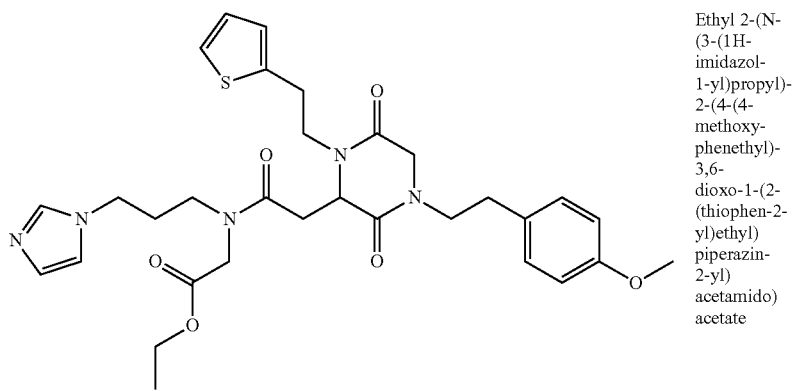 | Ethyl 2-(N-(3-(1H-imidazol-1-yl)propyl)-2-(4-(4-methoxyphenethyl)-3,6-dioxo-1-(2-(thiophen-2-yl)ethyl)piperazin-2-yl)acetamido)acetate | B | 2.757 | 610 |
| Ic.9.9 | 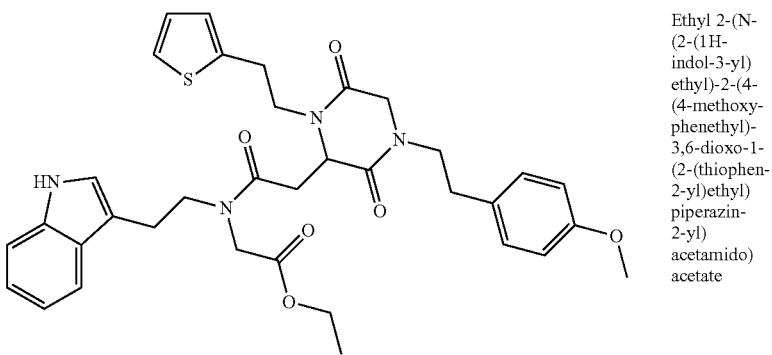 | Ethyl 2-(N-(2-(1H-indol-3-yl)ethyl)-2-(4-(4-methoxyphenethyl)-3,6-dioxo-1-(2-(thiophen-2-yl)ethyl)piperazin-2-yl)acetamido)acetate | B | 3.964 | 645 |
| Ic.9.10 | 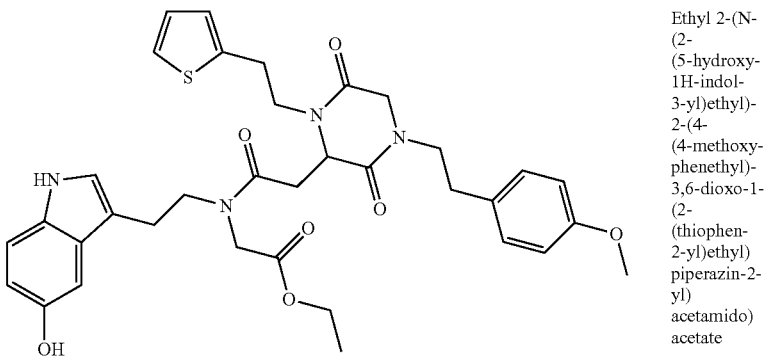 | Ethyl 2-(N-(2-(5-hydroxy-1H-indol-3-yl)ethyl)-2-(4-(4-methoxyphenethyl)-3,6-dioxo-1-(2-(thiophen-2-yl)ethyl)piperazin-2-yl)acetamido)acetate | B | 3.488 | 661 |

-continued

| Ic.9.11 | 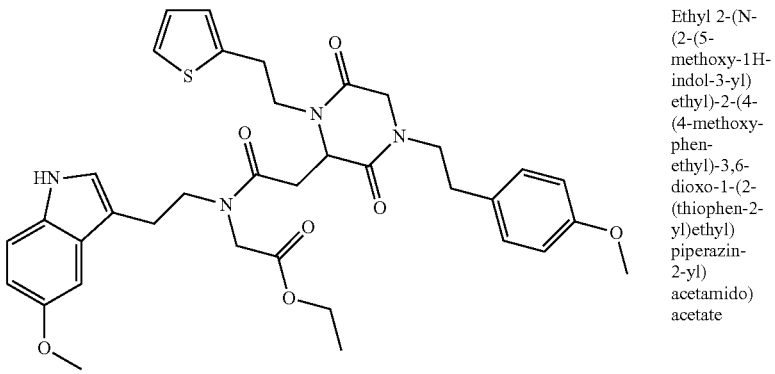 | Ethyl 2-(N-(2-(5-methoxy-1H-indol-3-yl)ethyl)-2-(4-(4-methoxy-phen-ethyl)-3,6-dioxo-1-(2-(thiophen-2-yl)ethyl)piperazin-2-yl)acetamido)acetate | B | 3.888 | 675 |
|---|---|---|---|---|---|
| Ic.9.12 | 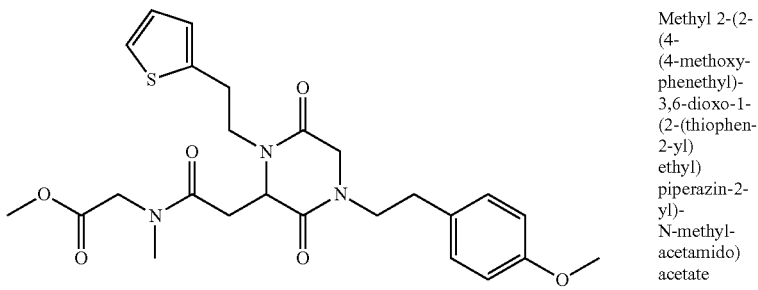 | Methyl 2-(2-(4-(4-methoxy-phenethyl)-3,6-dioxo-1-(2-(thiophen-2-yl)ethyl)piperazin-2-yl)-N-methyl-acetamido)acetate | B | 3.233 | 502 |
| Ic.9.13 | 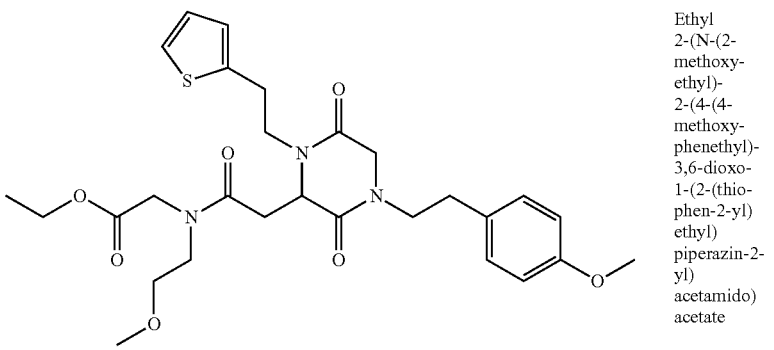 | Ethyl 2-(N-(2-methoxy-ethyl)-2-(4-(4-methoxy-phenethyl)-3,6-dioxo-1-(2-(thio-phen-2-yl)ethyl)piperazin-2-yl)acetamido)acetate | B | 3.568 | 560 |
| Ic.9.14 | 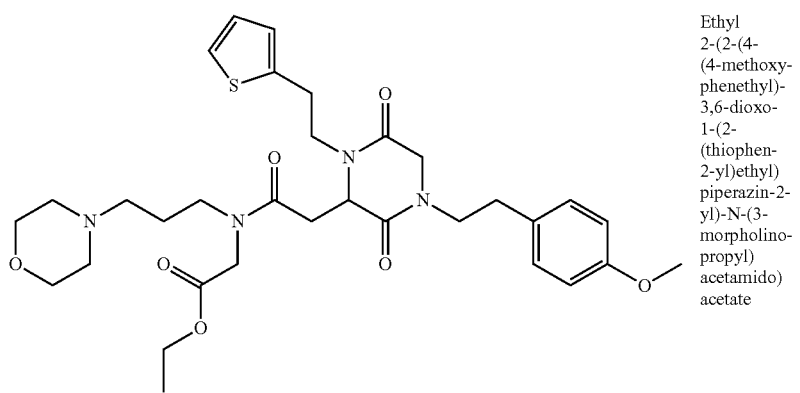 | Ethyl 2-(2-(4-(4-methoxy-phenethyl)-3,6-dioxo-1-(2-(thiophen-2-yl)ethyl)piperazin-2-yl)-N-(3-morpholino-propyl)acetamido)acetate | B | 2.772 | 629 |

-continued

| | | | | | |
|---|---|---|---|---|---|
| Ic.9.15 | 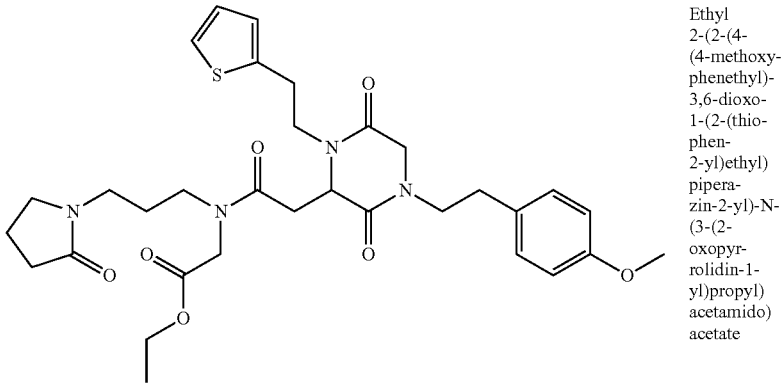 | Ethyl 2-(2-(4-(4-methoxyphenethyl)-3,6-dioxo-1-(2-(thiophen-2-yl)ethyl)piperazin-2-yl)-N-(3-(2-oxopyrrolidin-1-yl)propyl)acetamido)acetate | | 3.316 | 627 |
| Ic.10.1 | 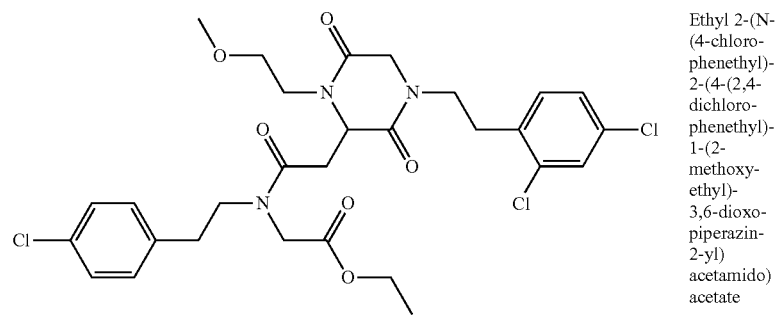 | Ethyl 2-(N-(4-chlorophenethyl)-2-(4-(2,4-dichlorophenethyl)-1-(2-methoxyethyl)-3,6-dioxopiperazin-2-yl)acetamido)acetate | B | 4.376 | 626 628 |
| Ic.10.2 | 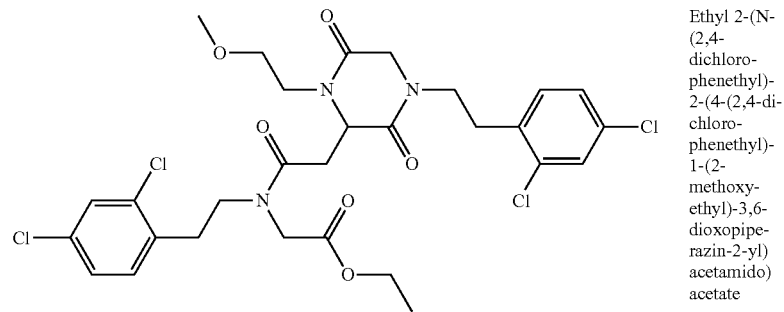 | Ethyl 2-(N-(2,4-dichlorophenethyl)-2-(4-(2,4-dichlorophenethyl)-1-(2-methoxyethyl)-3,6-dioxopiperazin-2-yl)acetamido)acetate | B | 4.621 | 660 662 |
| Ic.10.3 | 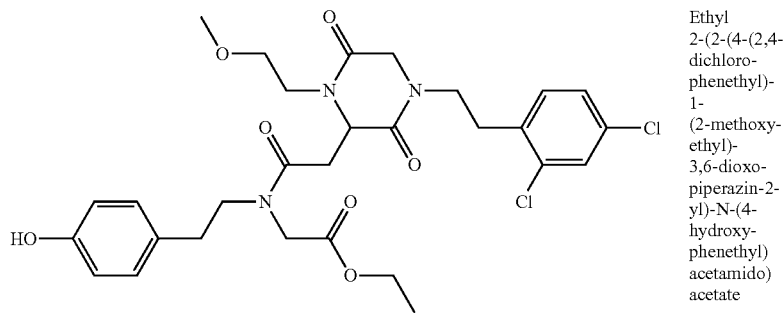 | Ethyl 2-(2-(4-(2,4-dichlorophenethyl)-1-(2-methoxyethyl)-3,6-dioxopiperazin-2-yl)-N-(4-hydroxyphenethyl)acetamido)acetate | B | 3.637 | 608 610 |

-continued

| | | | | | |
|---|---|---|---|---|---|
| Ic.10.4 | 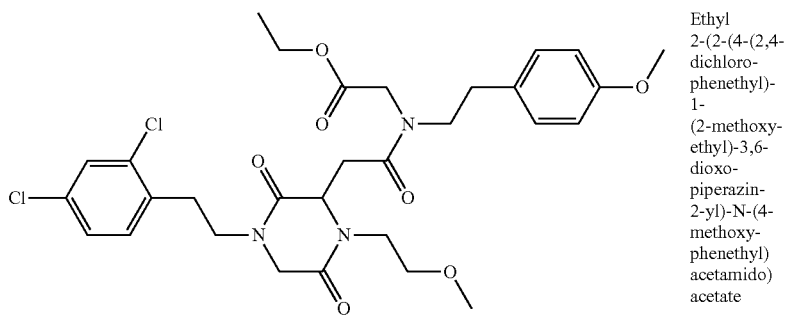 | Ethyl 2-(2-(4-(2,4-dichlorophenethyl)-1-(2-methoxyethyl)-3,6-dioxopiperazin-2-yl)-N-(4-methoxyphenethyl)acetamido)acetate | B | 4.110 | 622 624 |
| Ic.10.5 | 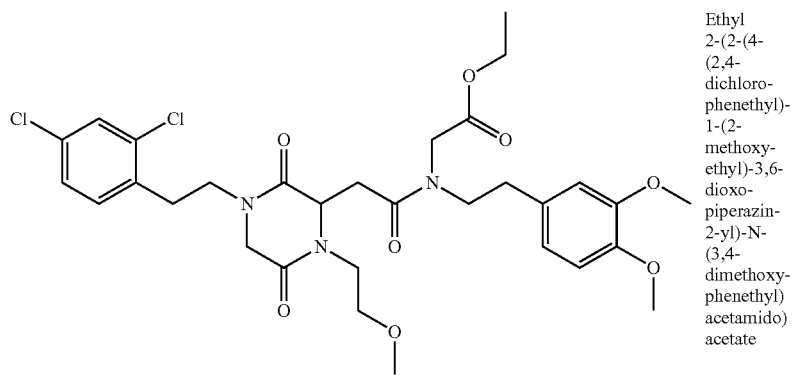 | Ethyl 2-(2-(4-(2,4-dichlorophenethyl)-1-(2-methoxyethyl)-3,6-dioxopiperazin-2-yl)-N-(3,4-dimethoxyphenethyl)acetamido)acetate | B | 3.917 | 652 654 |
| Ic.10.6 | 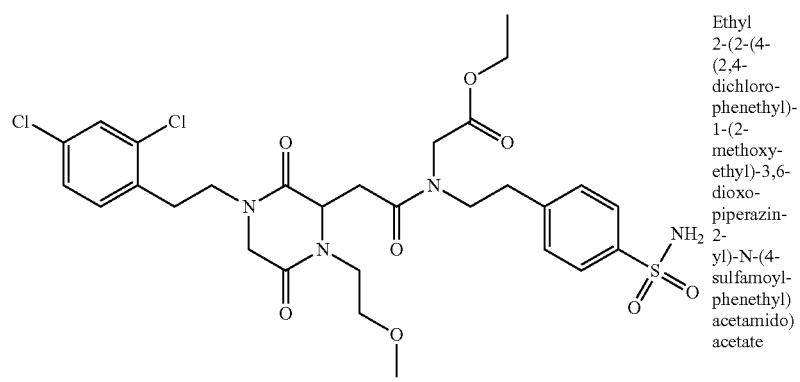 | Ethyl 2-(2-(4-(2,4-dichlorophenethyl)-1-(2-methoxyethyl)-3,6-dioxopiperazin-2-yl)-N-(4-sulfamoylphenethyl)acetamido)acetate | B | 3.511 | 671 673 |
| Ic.10.7 | 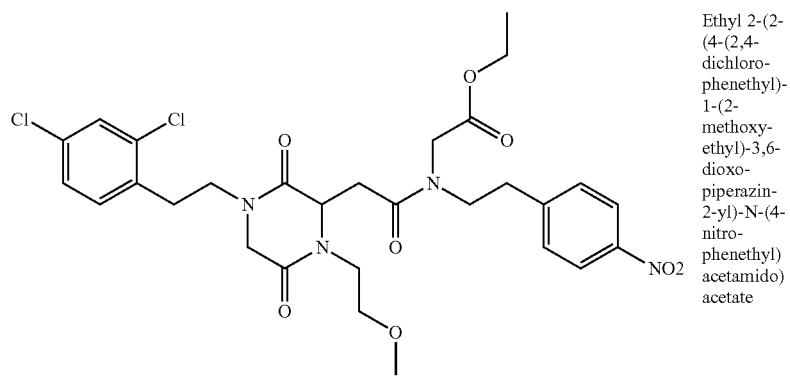 | Ethyl 2-(2-(4-(2,4-dichlorophenethyl)-1-(2-methoxyethyl)-3,6-dioxopiperazin-2-yl)-N-(4-nitrophenethyl)acetamido)acetate | B | 4.084 | 637 639 |

| | | | | |
|---|---|---|---|---|
| Ic.10.8 | 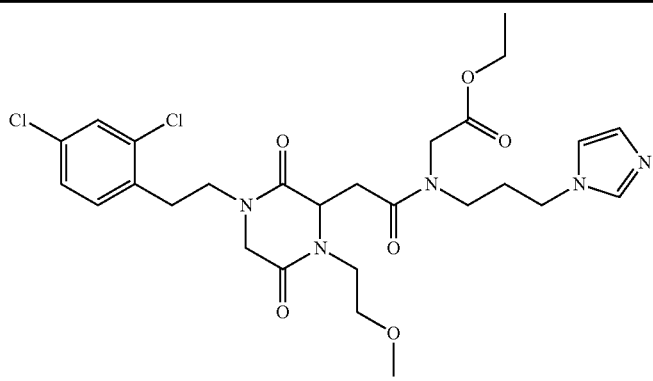 | Ethyl 2-(N-(3-(1H-imidazol-1-yl)propyl)-2-(4-(2,4-dichlorophenethyl)-1-(2-methoxyethyl)-3,6-dioxopiperazin-2-yl)acetamido)acetate | B | 2.759 596 598 |
| Ic.10.9 | 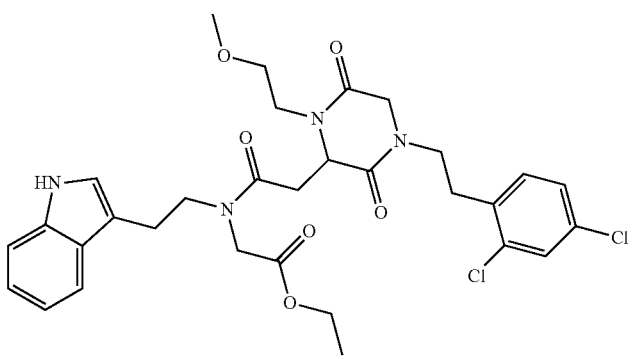 [SMILES: CCOC(=O)CN(CCc1c[nH]c2ccccc12)C(=O)CC1C(=O)N(CCc2ccc(Cl)cc2Cl)CC(=O)N1CCOC] | Ethyl 2-(N-(2-(1H-indol-3-yl)ethyl)-2-(4-(2,4-dichlorophenethyl)-1-(2-methoxyethyl)-3,6-dioxopiperazin-2-yl)acetamido)acetate | B | 4.021 631 633 |
| Ic.10.11 | 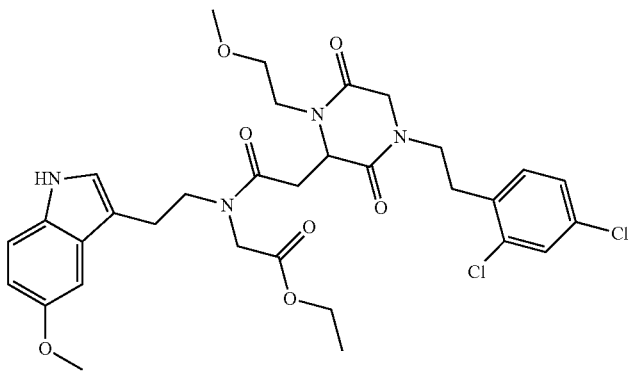 [SMILES: CCOC(=O)CN(CCc1c[nH]c2ccc(OC)cc12)C(=O)CC1C(=O)N(CCc2ccc(Cl)cc2Cl)CC(=O)N1CCOC] | Ethyl 2-(2-(4-(2,4-dichlorophenethyl)-1-(2-methoxyethyl)-3,6-dioxopiperazin-2-yl)-N-(2-(5-methoxy-1H-indol-3-yl)ethyl)acetamido)acetate | B | 3.941 661 663 |
| Ic.10.14 | 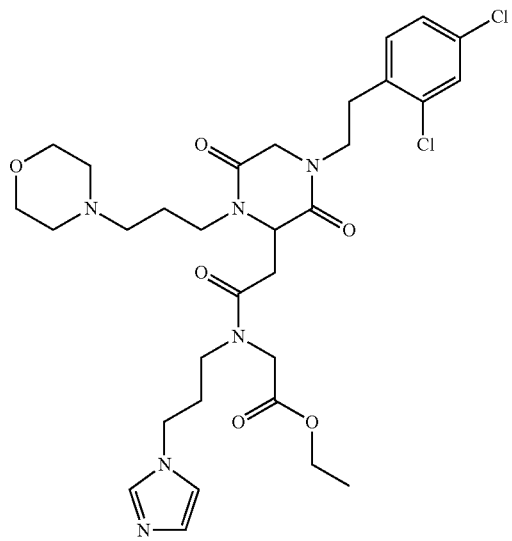 [SMILES: CCOC(=O)CN(CCCn1ccnc1)C(=O)CC1C(=O)N(CCc2ccc(Cl)cc2Cl)CC(=O)N1CCCN1CCOCC1] | Ethyl 2-(N-(3-(1H-imidazol-1-yl)propyl)-2-(4-(2,4-dichlorophenethyl)-1-(3-morpholinopropyl)-3,6-dioxopiperazin-2-yl)acetamido)acetate | B | 2.188 665 667 |

| | | | | | |
|---|---|---|---|---|---|
| Ic.11.1 | 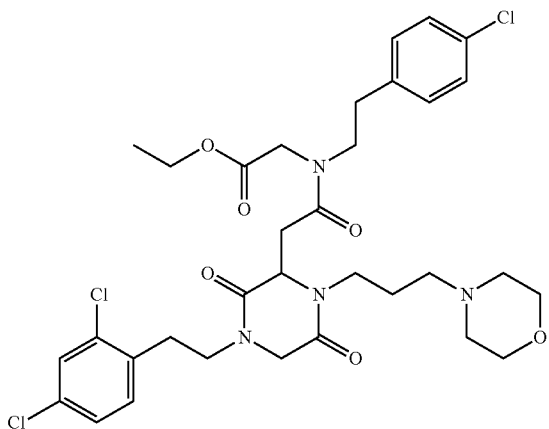 [SMILES: CCOC(=O)CN(CCc1ccc(Cl)cc1)C(=O)CC1C(=O)N(CCc2ccc(Cl)cc2Cl)CC(=O)N1CCCN1CCOCC1] | Ethyl 2-(N-(4-chlorophen-ethyl)-2-(4-(2,4-dichloro-phenethyl)-1-(3-morpholino-propyl)-3,6-dioxo-piperazin-2-yl)acetamido)acetate | B | 3.461 | 695 697 |
| Ic.11.2 | 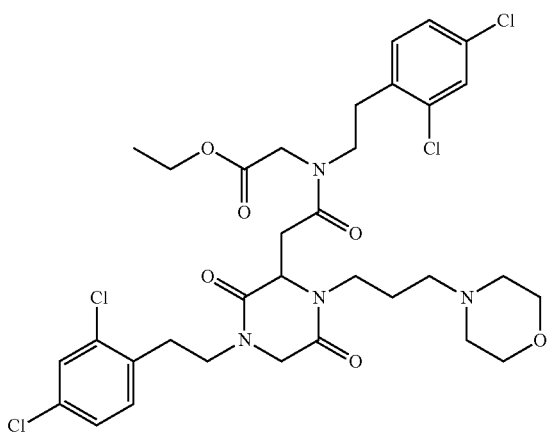 [SMILES: CCOC(=O)CN(CCc1ccc(Cl)cc1Cl)C(=O)CC1C(=O)N(CCc2ccc(Cl)cc2Cl)CC(=O)N1CCCN1CCOCC1] | Ethyl 2-(N-(2,4-dichloro-phenethyl)-2-(4-(2,4-dichloro-phenethyl)-1-(3-morpholino-propyl)-3,6-dioxo-piperazin-2-yl)acetamido)acetate | B | 3.590 | 729 731 |
| Ic.11.3 | 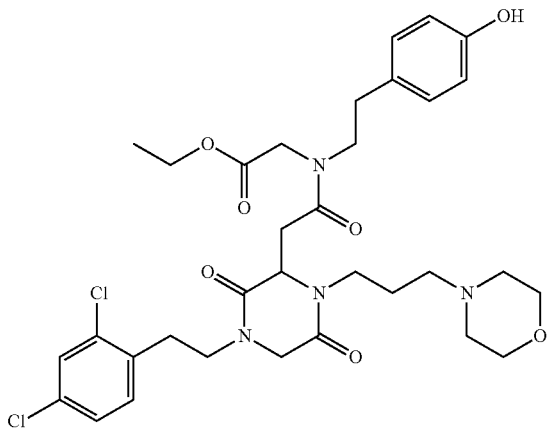 [SMILES: CCOC(=O)CN(CCc1ccc(O)cc1)C(=O)CC1C(=O)N(CCc2ccc(Cl)cc2Cl)CC(=O)N1CCCN1CCOCC1] | Ethyl 2-(2-(4-(2,4-dichloro-phenethyl)-1-(3-morpholino-propyl)-3,6-dioxo-piperazin-2-yl)-N-(4-hydroxy-phenethyl)acetamido)acetate | B | 2.970 | 677 679 |

| | | | | | |
|---|---|---|---|---|---|
| Ic.11.4 | 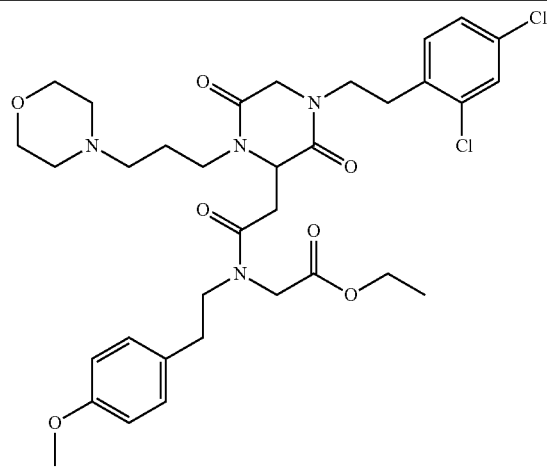 | Ethyl 2-(2-(4-(2,4-dichloro-phenethyl)-1-(3-morpholino-propyl)-3,6-dioxo-piperazin-2-yl)-N-(4-meth-oxy-phenethyl) acetamido) acetate | B | 3.295 | 691 693 |
| Ic.11.5 | 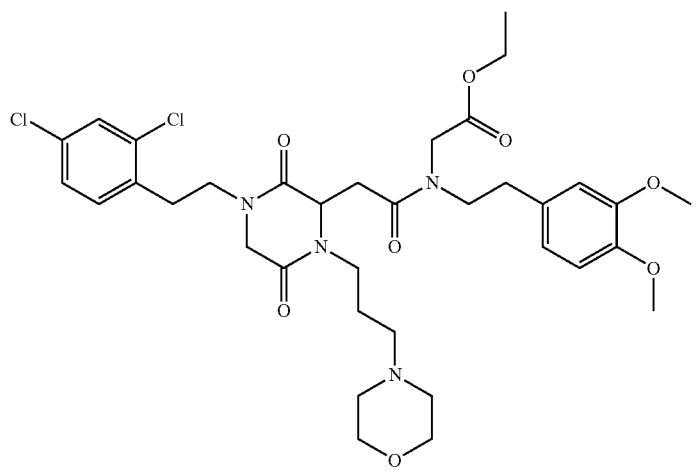 [SMILES: CCOC(=O)CN(CCc1ccc(OC)c(OC)c1)C(=O)CC1C(=O)N(CCc2ccc(Cl)cc2Cl)CC(=O)N1CCCN1CCOCC1] | Ethyl 2-(2-(4-(2,4-dichloro-phenethyl)-1-(3-morpholino-propyl)-3,6-dioxo-piperazin-2-yl)-N-(3,4-dimethoxy-phenethyl) acetamido) acetate | B | 3.150 | 721 723 |
| Ic.11.6 | 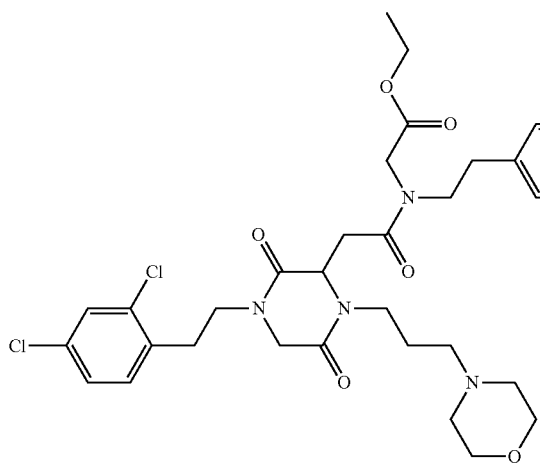 | Ethyl 2-(2-(4-(2,4-dichloro-phenethyl)-1-(3-morpholino-propyl)-3,6-dioxo-piperazin-2-yl)-N-(4-sulfamoyl-phenethyl) acetamido) acetate | B | 2.867 | 527 529 |

| | | | | |
|---|---|---|---|---|
| Ic.11.7 | 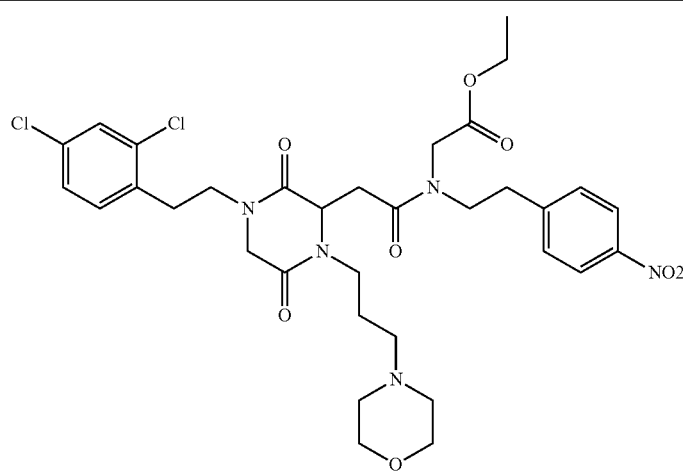 | Ethyl 2-(2-(4-(2,4-dichloro-phenethyl)-1-(3-morpholino-propyl)-3,6-dioxo-piperazin-2-yl)-N-(4-nitro-phenethyl)acetamido)acetate | B | 3.291 706 708 |
| Ic.11.9 | 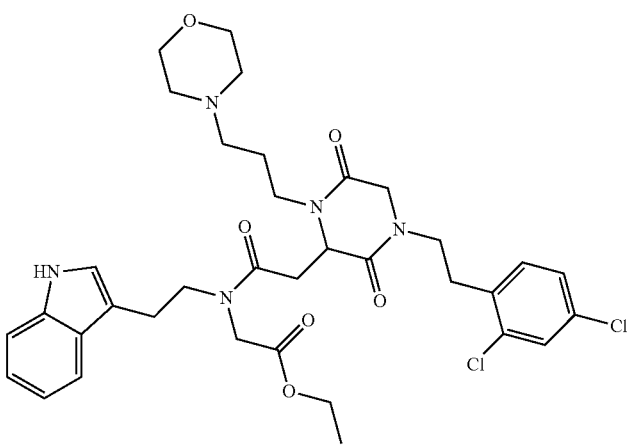 [SMILES: CCOC(=O)CN(CCc1c[nH]c2ccccc12)C(=O)CC1C(=O)N(CCc2ccc(Cl)cc2Cl)CC(=O)N1CCCN1CCOCC1] | Ethyl 2-(N-(2-(1H-indol-3-yl)ethyl)-2-(4-(2,4-dichloro-phenethyl)-1-(3-morpholino-propyl)-3,6-dioxo-piperazin-2-yl)acetamido)acetate | B | 3.234 700 702 |
| Ic.11.11 | 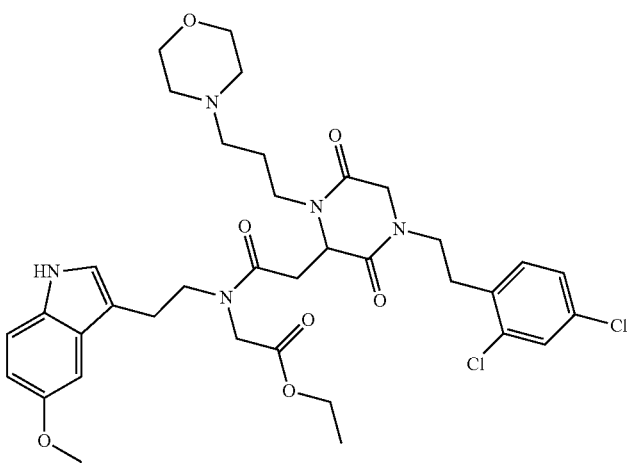 [SMILES: CCOC(=O)CN(CCc1c[nH]c2ccc(OC)cc12)C(=O)CC1C(=O)N(CCc2ccc(Cl)cc2Cl)CC(=O)N1CCCN1CCOCC1] | Ethyl 2-(2-(4-(2,4-dichloro-phenethyl)-1-(3-morpholino-propyl)-3,6-dioxo-piperazin-2-yl)-N-(2-(5-methoxy-1H-indol-3-yl)ethyl)acetamido)acetate | B | 3.164 730 732 |

| | | | | | |
|---|---|---|---|---|---|
| Ic.11.16 | 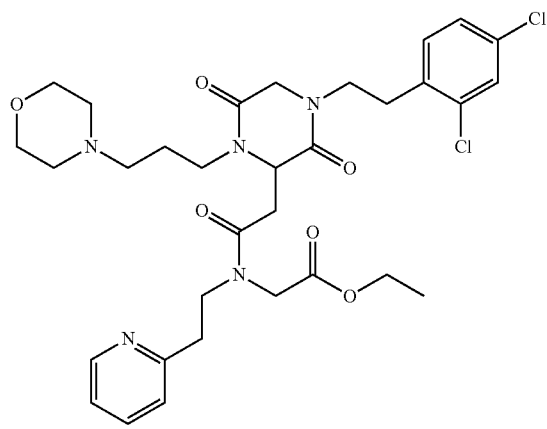 [SMILES: CCOC(=O)CN(CCc1ccccn1)C(=O)CC1C(=O)N(CCc2ccc(Cl)cc2Cl)CC(=O)N1CCCN1CCOCC1] | Ethyl 2-(2-(4-(2,4-dichloro-phenethyl)-1-(3-morpholino-propyl)-3,6-dioxo-piperazin-2-yl)-N-(2-(pyridin-2-yl)ethyl)acetamido)acetate | B | 2.500 | 662 664 |
| Ic.11.17 | 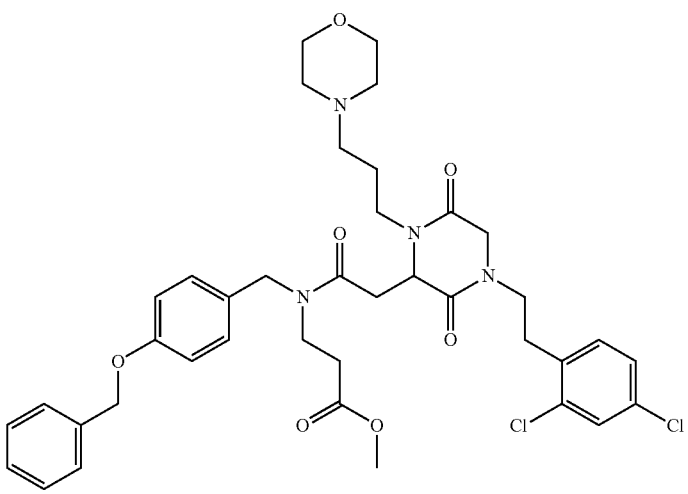 [SMILES: COC(=O)CCN(Cc1ccc(OCc2ccccc2)cc1)C(=O)CC1C(=O)N(CCc2ccc(Cl)cc2Cl)CC(=O)N1CCCN1CCOCC1] | Methyl 3-(N-(4-(benzyloxy)benzyl)-2-(4-(2,4-dichloro-phenethyl)-1-(3-morpholino-propyl)-3,6-dioxo-piperazin-2-yl)acetamido)propanoate | B | 3.551 | 735 737 |
| Ic.11.18 | 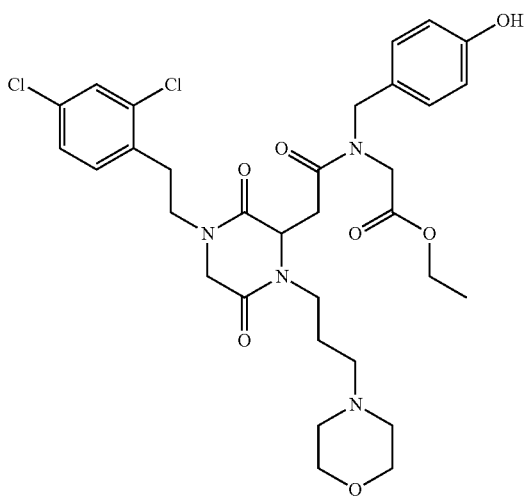 [SMILES: CCOC(=O)CN(Cc1ccc(O)cc1)C(=O)CC1C(=O)N(CCc2ccc(Cl)cc2Cl)CC(=O)N1CCCN1CCOCC1] | Ethyl 2-(2-(4-(2,4-dichloro-phenethyl)-1-(3-morpholino-propyl)-3,6-dioxo-piperazin-2-yl)-N-(4-hydroxy-benzyl)acetamido)acetate | B | 2.787 | 663 665 |

| | | | | | |
|---|---|---|---|---|---|
| Ic.13.1 | 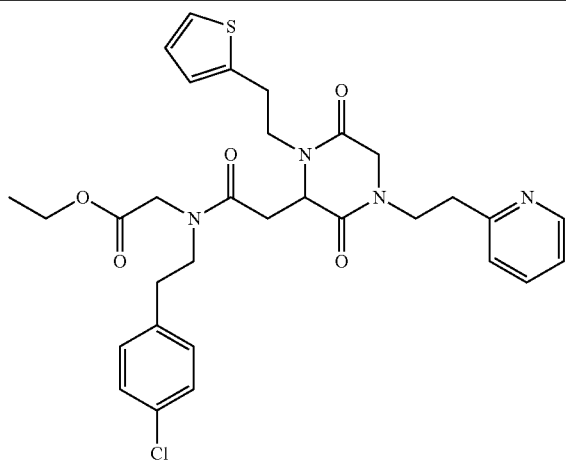 | Ethyl 2-(N-(4-chloro-phenethyl)-2-(3,6-dioxo-4-(2-(pyridin-2-yl)ethyl)-1-(2-(thiophen-2-yl)ethyl)piperazin-2-yl)acetamido)acetate | C | 3.763 | 611 613 |
| Ic.13.2 | 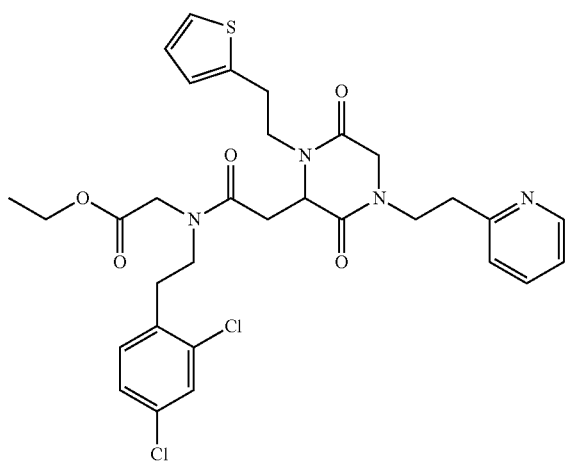 [SMILES: CCOC(=O)CN(CCc1ccc(Cl)cc1Cl)C(=O)CC1C(=O)N(CCc2ccccn2)CC(=O)N1CCc1cccs1] | Ethyl 2-(N-(2,4-dichlorophen-ethyl)-2-(3,6-dioxo-4-(2-(pyridin-2-yl)ethyl)-1-(2-(thiophen-2-yl)ethyl)piperazin-2-yl)acetamido)acetate | C | 3.957 | 645 647 |
| Ic.13.5 | 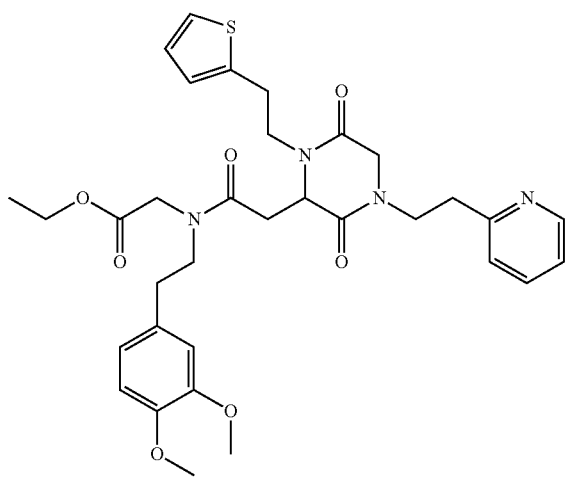 [SMILES: CCOC(=O)CN(CCc1ccc(OC)c(OC)c1)C(=O)CC1C(=O)N(CCc2ccccn2)CC(=O)N1CCc1cccs1] | Ethyl 2-(N-(3,4-dimethoxy-phenethyl)-2-(3,6-dioxo-4-(2-(pyridin-2-yl)ethyl)-1-(2-(thiophen-2-yl)ethyl)piperazin-2-yl)acetamido)acetate | C | 3.378 | 637 |

-continued
| | | | | | |
|---|---|---|---|---|---|
| Ic.13.7 | 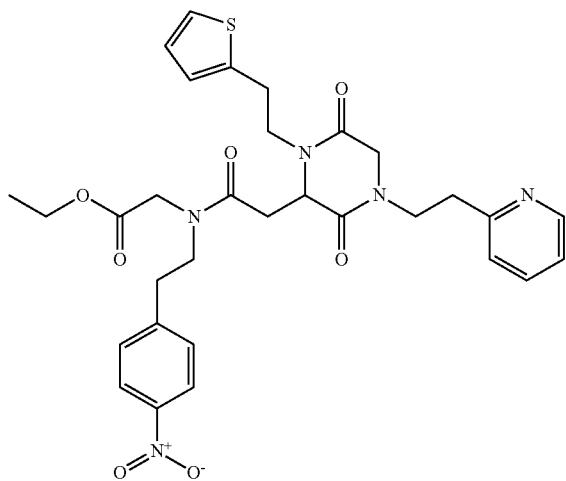 [SMILES: CCOC(=O)CN(CCc1ccc([N+](=O)[O-])cc1)C(=O)CC1C(=O)N(CCc2ccccn2)CC(=O)N1CCc1cccs1] | Ethyl 2-(2-(3,6-dioxo-4-(2-(pyridin-2-yl)ethyl)-1-(2-(thiophen-2-yl)ethyl)piperazin-2-yl)-N-(4-nitrophenethyl)acetamido)acetate | C | 3.528 | 622 |
| Ic.13.9 | 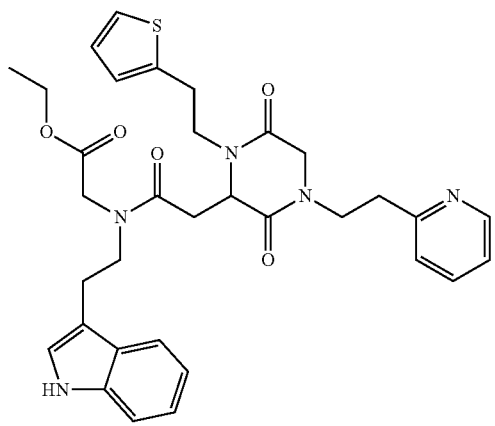 [SMILES: CCOC(=O)CN(CCc1c[nH]c2ccccc12)C(=O)CC1C(=O)N(CCc2ccccn2)CC(=O)N1CCc1cccs1] | Ethyl-2-(N-(2-(1H-indol-3-yl)ethyl)-2-(3,6-dioxo-4-(2-(pyridin-2-yl)ethyl)-1-(2-(thiophen-2-yl)ethyl)piperazin-2-yl)acetamido)acetate | C | 3.480 | 616 |
| Ic.13.11 | 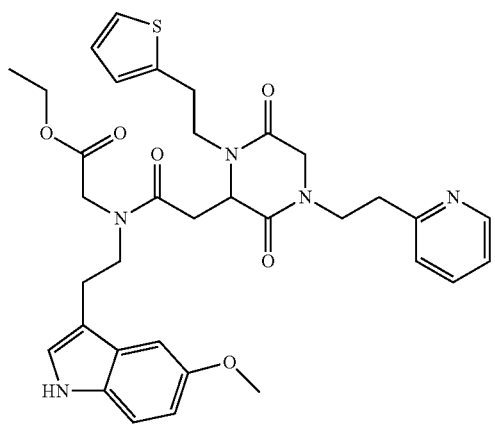 | Ethyl 2-(2-(3,6-dioxo-4-(2-(pyridin-2-yl)ethyl)-1-(2-(thiophen-2-yl)ethyl)piperazin-2-yl)-N-(2-(5-methoxy-1H-indol-3-yl)ethyl)acetamido)acetate | B | 2.914 | 646 |

| | | | | | |
|---|---|---|---|---|---|
| Ic.14.1 | 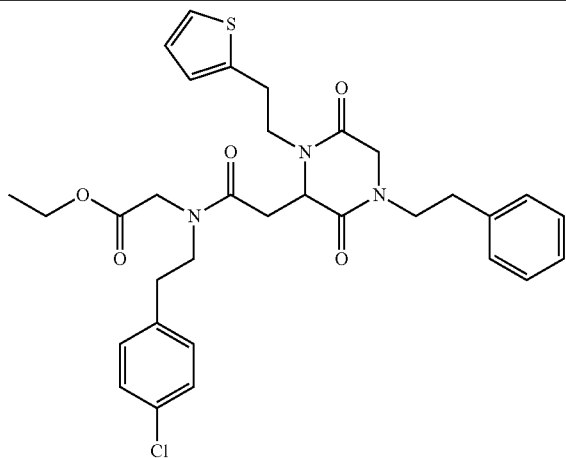 | Ethyl 2-(N-(4-chloro-phenethyl)-2-(3,6-dioxo-4-phenethyl-1-(2-(thiophen-2-yl)ethyl)piperazin-2-yl)acetamido)acetate | B | 4.331 | 610 612 |
| Ic.14.2 | 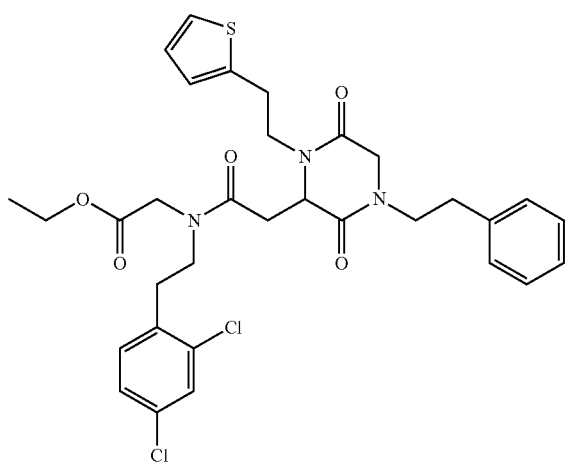 [SMILES: CCOC(=O)CN(CCc1ccc(Cl)cc1Cl)C(=O)CC1C(=O)N(CCc2ccccc2)CC(=O)N1CCc1cccs1] | Ethyl 2-(N-(2,4-dichloro-phenethyl)-2-(3,6-dioxo-4-phenethyl-1-(2-(thiophen-2-yl)ethyl)piperazin-2-yl)acetamido)acetate | C | 5.072 | 644 646 |
| Ic.14.4 | 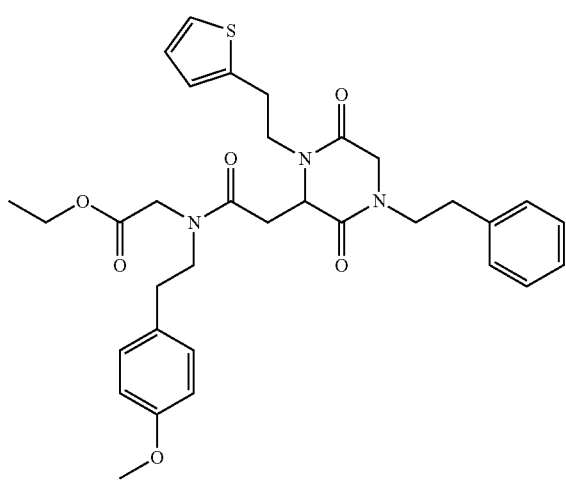 [SMILES: CCOC(=O)CN(CCc1ccc(OC)cc1)C(=O)CC1C(=O)N(CCc2ccccc2)CC(=O)N1CCc1cccs1] | Ethyl 2-(2-(3,6-dioxo-4-phenthyl-1-(2-(thiophen-2-yl)ethyl)piperazin-2-yl)-N-(4-methoxy-phenethyl)acetamido)acetate | B | 4.101 | 606 |

-continued
| | | | | | |
|---|---|---|---|---|---|
| Ic.14.5 | 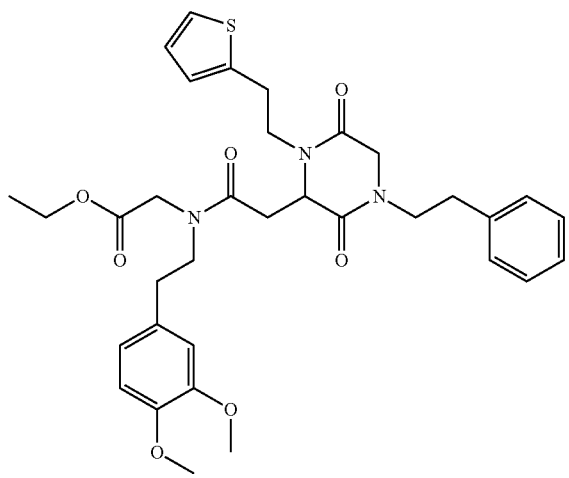 [SMILES: CCOC(=O)CN(CCc1ccc(OC)c(OC)c1)C(=O)CC1C(=O)N(CCc2ccccc2)CC(=O)N1CCc1cccs1] | Ethyl 2-(N-(3,4-dimethoxyphenethyl)-2-(3,6-dioxo-4-phenethyl-1-(2-(thiophen-2-yl)ethyl)piperazin-2-yl)acetamido)acetate | C | 4.432 | 636 |
| Ic.14.6 | 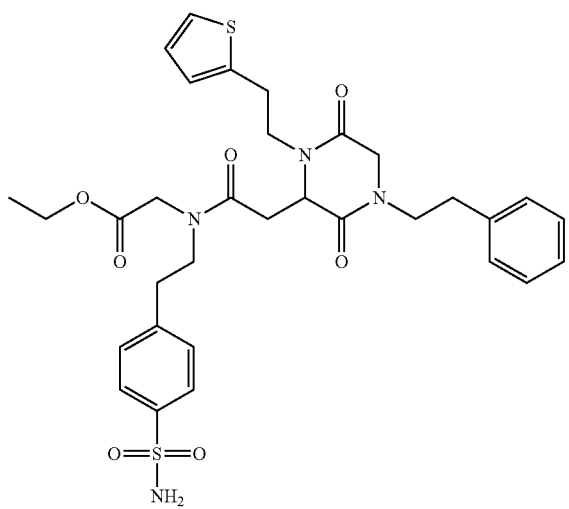 [SMILES: CCOC(=O)CN(CCc1ccc(S(N)(=O)=O)cc1)C(=O)CC1C(=O)N(CCc2ccccc2)CC(=O)N1CCc1cccs1] | Ethyl 2-(2-(3,6-dioxo-4-phenethyl-1-(2-(thiophen-2-yl)ethyl)piperazin-2-yl)-N-(4-sulfamoylphenethyl)acetamido)acetate | B | 3.522 | 655 |
| Ic.14.7 | 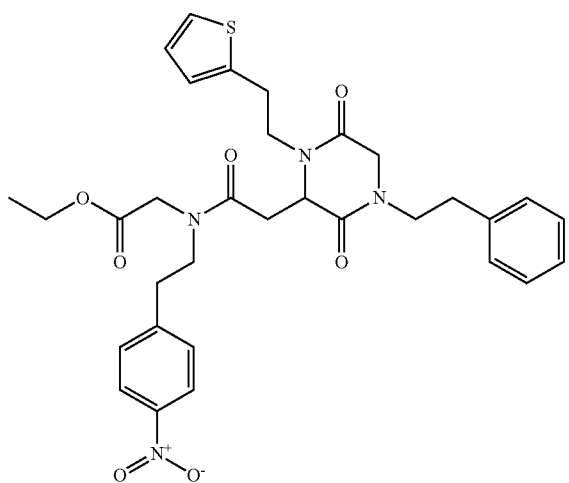 [SMILES: CCOC(=O)CN(CCc1ccc([N+](=O)[O-])cc1)C(=O)CC1C(=O)N(CCc2ccccc2)CC(=O)N1CCc1cccs1] | Ethyl 2-(2-(3,6-dioxo-4-phenethyl-1-(2-(thiophen-2-yl)ethyl)piperazin-2-yl)-N-(4-nitrophenethyl)acetamido)acetate | C | 4.578 | 621 |

| | | | | | |
|---|---|---|---|---|---|
| Ic.14.9 | 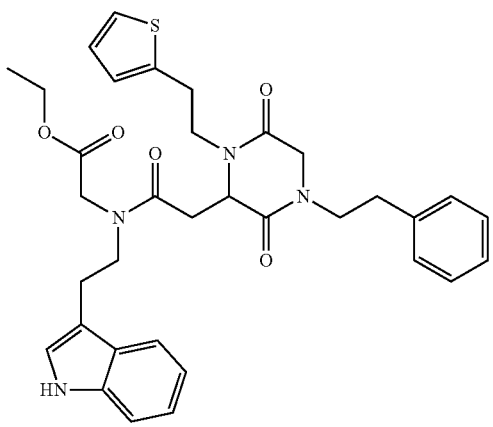 [SMILES: CCOC(=O)CN(CCc1c[nH]c2ccccc12)C(=O)CC1C(=O)N(CCc2ccccc2)CC(=O)N1CCc1cccs1] | Ethyl 2-(N-(2-(1H-indol-3-yl)ethyl)-2-(3,6-dioxo-4-phenethyl-1-(2-(thiophen-2-yl)ethyl)piperazin-2-yl)acetamido)acetate | B | 3.996 | 616 |
| Ic.14.11 | 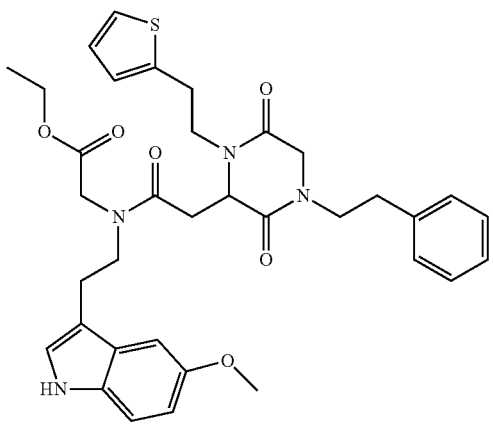 [SMILES: CCOC(=O)CN(CCc1c[nH]c2ccc(OC)cc12)C(=O)CC1C(=O)N(CCc2ccccc2)CC(=O)N1CCc1cccs1] | Ethyl 2-(2-(3,6-dioxo-4-phenethyl-1-(2-(thiophen-2-yl)ethyl)piperazin-2-yl)-N-(2-(5-methoxy-1H-indol-3-yl)ethyl)acetamido)acetate | C | 4.447 | 645 |
| Ic.14.13 | 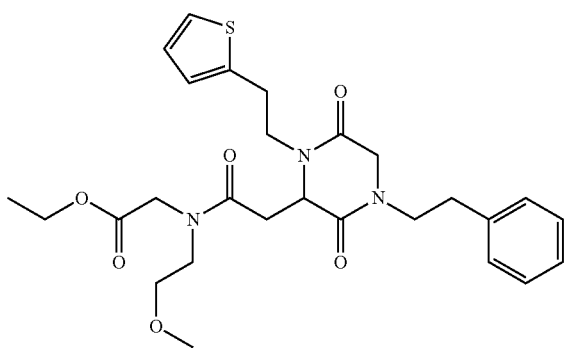 [SMILES: CCOC(=O)CN(CCOC)C(=O)CC1C(=O)N(CCc2ccccc2)CC(=O)N1CCc1cccs1] | Ethyl 2-(2-(3,6-dioxo-4-phenethyl-1-(2-(thiophen-2-yl)ethyl)piperazin-2-yl)-N-(2-methoxyethyl)acetamido)acetate | B | 3.610 | 530 |
| Ic.14.19.2 | 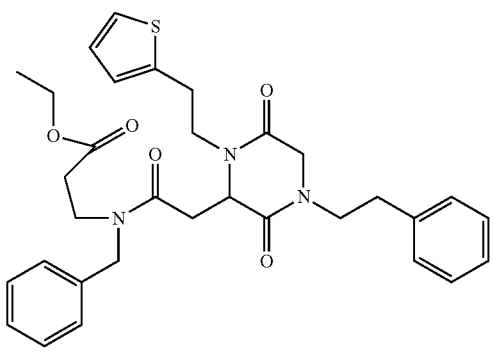 [SMILES: CCOC(=O)CCN(Cc1ccccc1)C(=O)CC1C(=O)N(CCc2ccccc2)CC(=O)N1CCc1cccs1] | Ethyl 3-(N-benzyl-2-(3,6-dioxo-4-phenethyl-1-(2-(thiophen-2-yl)ethyl)piperazin-2-yl)acetamido)propanoate | B | 4.108 | 576 |

| | | | | |
|---|---|---|---|---|
| Ic.15.1 | 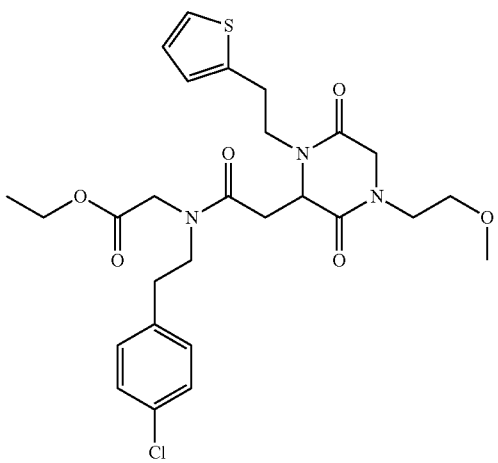 [SMILES: CCOC(=O)CN(CCc1ccc(Cl)cc1)C(=O)CC1C(=O)N(CCOC)CC(=O)N1CCc1cccs1] | Ethyl 2-(N-(4-chloro-phenethyl)-2-(4-(2-methoxy-ethyl)-3,6-dioxo-1-(2-(thiophen-2-yl)ethyl)piperazin-2-yl)acetamido)acetate | C | 4.337 564 566 |
| Ic.15.2 | 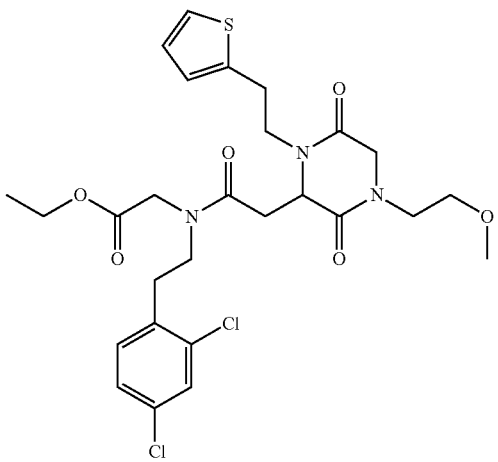 [SMILES: CCOC(=O)CN(CCc1ccc(Cl)cc1Cl)C(=O)CC1C(=O)N(CCOC)CC(=O)N1CCc1cccs1] | Ethyl 2-(N-(2,4-dichloro-phenethyl)-2-(4-(2-methoxy-ethyl)-3,6-dioxo-1-(2-(thiophen-2-yl)ethyl)piperazin-2-yl)acetamido)acetate | C | 4.580 598 600 |
| Ic.15.4 | 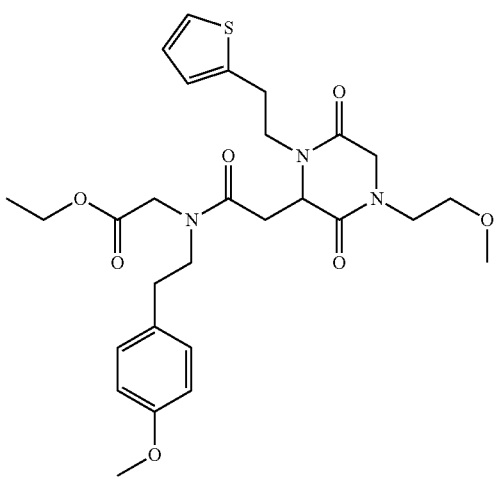 [SMILES: CCOC(=O)CN(CCc1ccc(OC)cc1)C(=O)CC1C(=O)N(CCOC)CC(=O)N1CCc1cccs1] | Ethyl 2-(2-(4-(2-methoxy-ethyl)-3,6-dioxo-1-(2-(thiophen-2-yl)ethyl)piperazin-2-yl)-N-(4-methoxy-phenethyl)acetamido)acetate | B | 3.548 560 |

| | | | | | |
|---|---|---|---|---|---|
| Ic.15.5 | 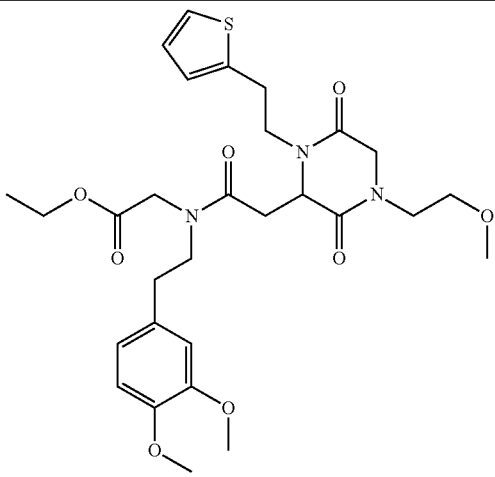 | Ethyl 2-(N-(3,4-dimethoxyphenethyl)-2-(4-(2-methoxyethyl)-3,6-dioxo-1-(2-(thiophen-2-yl)ethyl)piperazin-2-yl)acetamido)acetate | B | 3.885 | 590 |
| Ic.15.6 | 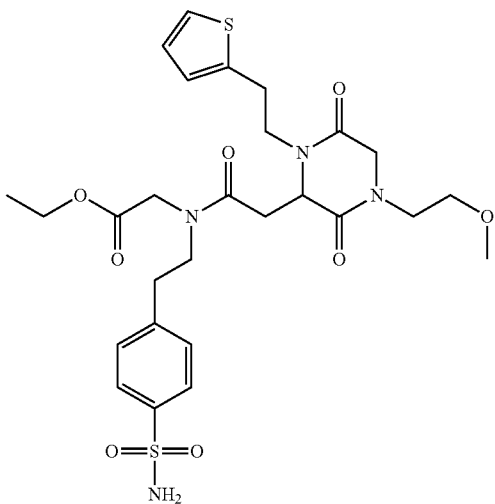 [SMILES: CCOC(=O)CN(CCc1ccc(S(N)(=O)=O)cc1)C(=O)CC1C(=O)N(CCOC)CC(=O)N1CCc1cccs1] | Ethyl 2-(2-(4-(2-methoxyethyl)-3,6-dioxo-1-(2-(thiophen-2-yl)ethyl)piperazin-2-yl)-N-(4-sulfamoylphenethyl)acetamido)acetate | B | 2.923 | 609 |
| Ic.15.7 | 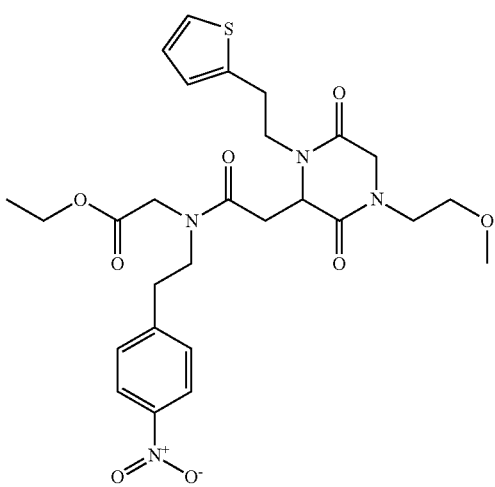 [SMILES: CCOC(=O)CN(CCc1ccc([N+](=O)[O-])cc1)C(=O)CC1C(=O)N(CCOC)CC(=O)N1CCc1cccs1] | Ethyl 2-(2-(4-(2-methoxyethyl)-3,6-dioxo-1-(2-(thiophen-2-yl)ethyl)piperazin-2-yl)-N-(4-nitrophenethyl)acetamido)acetate | C | 4.057 | 575 |

| | | | | |
|---|---|---|---|---|
| Ic.15.9 | 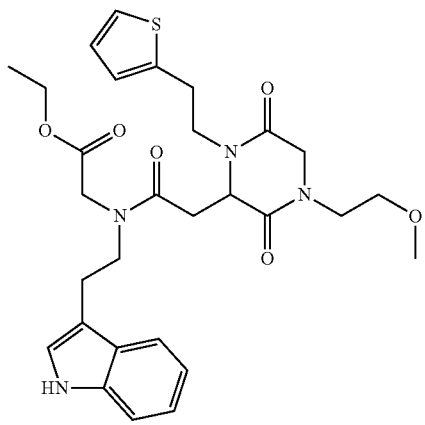 [SMILES: CCOC(=O)CN(CCc1c[nH]c2ccccc12)C(=O)CC1C(=O)N(CCOC)CC(=O)N1CCc1cccs1] | Ethyl 2-(N-(2-(1H-indol-3-yl)ethyl)-2-(4-(2-methoxy-ethyl)-3,6-dioxo-1-(2-(thiophen-2-yl)ethyl)piperazin-2-yl)acetamido)acetate | B | 3.462 569 |
| Ic.15.11 | 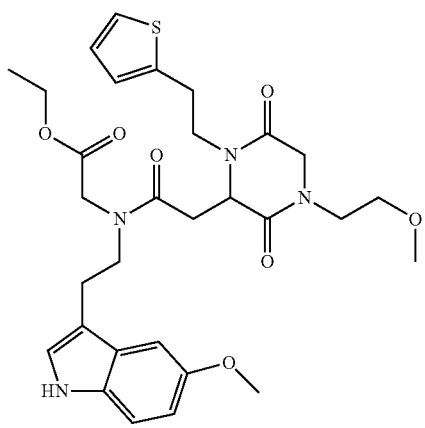 [SMILES: CCOC(=O)CN(CCc1c[nH]c2ccc(OC)cc12)C(=O)CC1C(=O)N(CCOC)CC(=O)N1CCc1cccs1] | Ethyl 2-(N-(2-(5-methoxy-1H-indol-3-yl)ethyl)-2-(4-(2-methoxy-ethyl)-3,6-dioxo-1-(2-(thiophen-2-yl)ethyl)piperazin-2-yl)acetamido)acetate | B | 3.383 599 |
| Ic.15.13 | 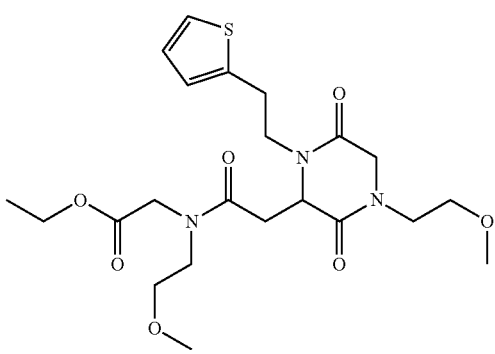 [SMILES: CCOC(=O)CN(CCOC)C(=O)CC1C(=O)N(CCOC)CC(=O)N1CCc1cccs1] | Ethyl 2-(N-(2-methoxy-ethyl)-2-(4-(2-methoxy-ethyl)-3,6-dioxo-1-(2-(thiophen-2-yl)ethyl)piperazin-2-yl)acetamido)acetate | B | 2.916 484 |
| Ic.15.19.2 | 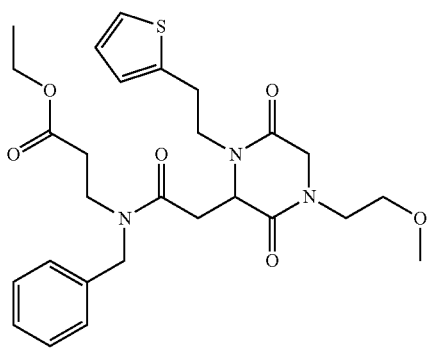 [SMILES: CCOC(=O)CCN(Cc1ccccc1)C(=O)CC1C(=O)N(CCOC)CC(=O)N1CCc1cccs1] | Ethyl 3-(N-benzyl-2-(4-(2-methoxy-ethyl)-3,6-dioxo-1-(2-(thiophen-2-yl)ethyl)piperazin-2-yl)acetamido)propanoate | B | 3.526 530 |

-continued
| | | | | | |
|---|---|---|---|---|---|
| Ic.16.1 | 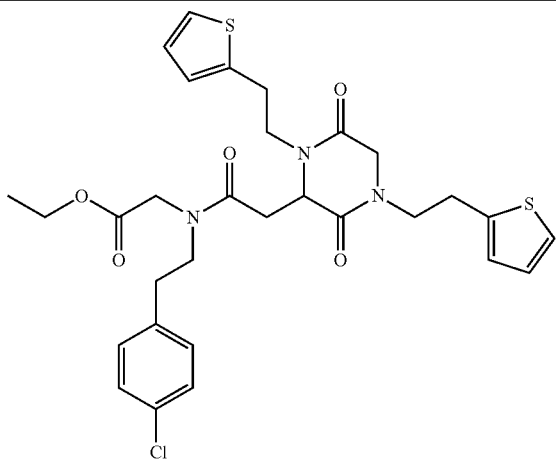 | Ethyl 2-(N-(4-chlorophen-ethyl)-2-(3,6-dioxo-1,4-bis(2-(thiophen-2-yl)ethyl)piperazin-2-yl)acetamido)acetate | C | 4.793 | 616 618 |
| Ic.16.2 | 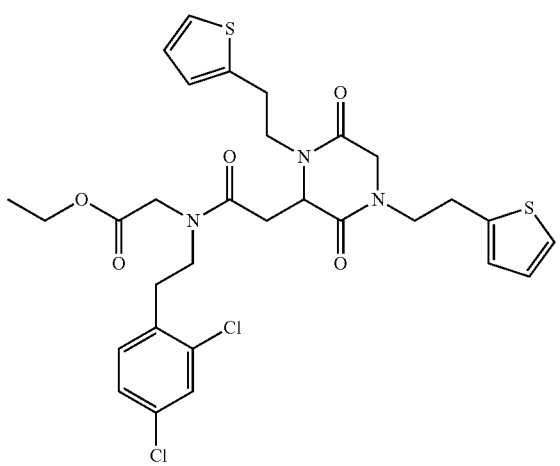 [SMILES: CCOC(=O)CN(CCc1ccc(Cl)cc1Cl)C(=O)CC1C(=O)N(CCc2cccs2)CC(=O)N1CCc1cccs1] | Ethyl 2-(N-(2,4-dichloro-phenethyl)-2-(3,6-dioxo-1,4-bis(2-(thiophen-2-yl)ethyl)piperazin-2-yl)acetamido)acetate | C | 5.008 | 650 652 |
| Ic.16.3 | 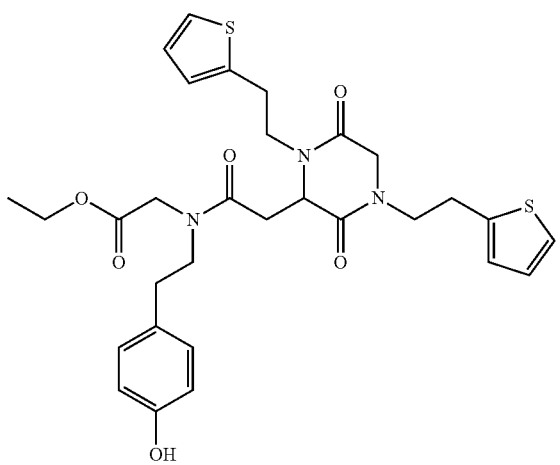 [SMILES: CCOC(=O)CN(CCc1ccc(O)cc1)C(=O)CC1C(=O)N(CCc2cccs2)CC(=O)N1CCc1cccs1] | Ethyl 2-(2-(3,6-dioxo-1,4-bis(2-(thiophen-2-yl)ethyl)piperazin-2-yl)-N-(4-hydroxy-phenethyl)acetamido)acetate | B | 3.569 | 598 |

-continued
| | | | | | |
|---|---|---|---|---|---|
| Ic.16.5 | 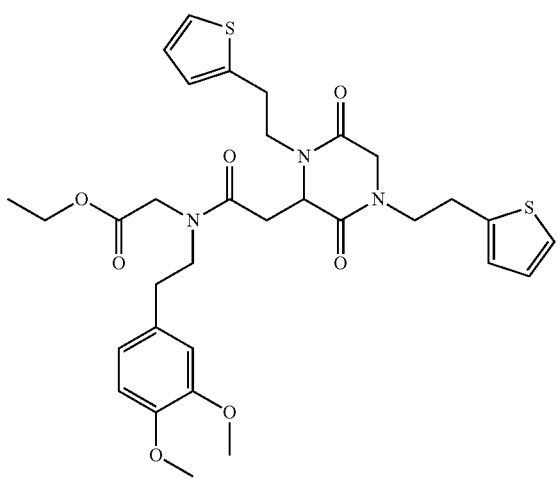 [SMILES: CCOC(=O)CN(CCc1ccc(OC)c(OC)c1)C(=O)CC1C(=O)N(CCc2cccs2)CC(=O)N1CCc1cccs1] | Ethyl 2-(N-(3,4-dimethoxy-phenethyl)-2-(3,6-dioxo-1,4-bis(2-(thiophen-2-yl)ethyl)piperazin-2-yl)acetamido)acetate | B | 3.836 | 642 |
| Ic.16.6 | 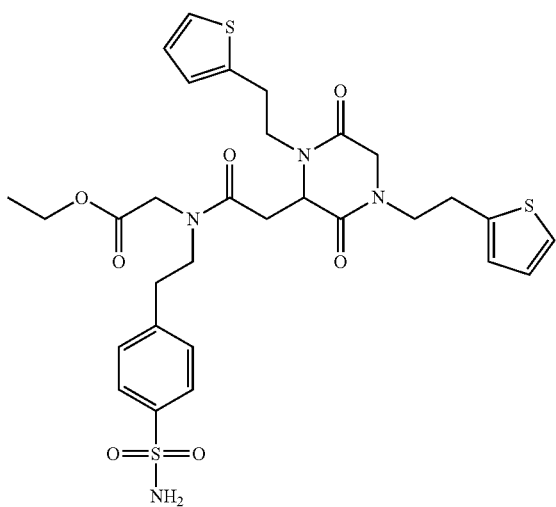 [SMILES: CCOC(=O)CN(CCc1ccc(S(N)(=O)=O)cc1)C(=O)CC1C(=O)N(CCc2cccs2)CC(=O)N1CCc1cccs1] | Ethyl 2-(2-(3,6-dioxo-1,4-bis(2-(thiophen-2-yl)ethyl)piperazin-2-yl)-N-(4-sulfamoyl-phenethyl)acetamido)acetate | B | 3.450 | 660 |
| Ic.16.7 | 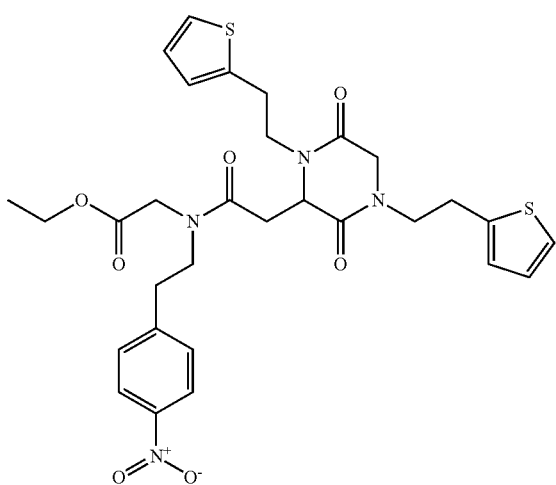 [SMILES: CCOC(=O)CN(CCc1ccc([N+](=O)[O-])cc1)C(=O)CC1C(=O)N(CCc2cccs2)CC(=O)N1CCc1cccs1] | Ethyl 2-(2-(3,6-dioxo-1,4-bis(2-(thiophen-2-yl)ethyl)piperazin-2-yl)-N-(4-nitro-phenethyl)acetamido)acetate | C | 4.522 | 627 |

| | | | | |
|---|---|---|---|---|
| Ic.16.8 | 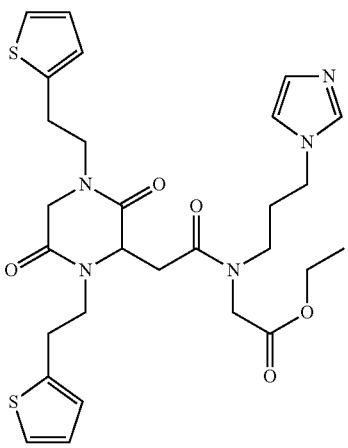 [SMILES: CCOC(=O)CN(CCCn1ccnc1)C(=O)CC1C(=O)N(CCc2cccs2)CC(=O)N1CCc1cccs1] | Ethyl 2-(N-(3-(1H-imidazol-1-yl)propyl)-2-(3,6-dioxo-1,4-bis(2-(thiophen-2-yl)ethyl)piperazin-2-yl)acetamido)acetate | B | 2.709 586 |
| Ic.16.9 | 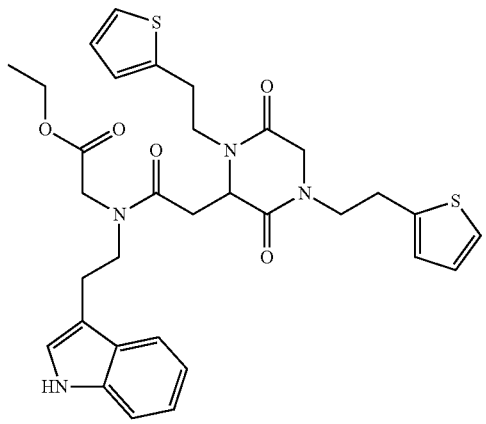 [SMILES: CCOC(=O)CN(CCc1c[nH]c2ccccc12)C(=O)CC1C(=O)N(CCc2cccs2)CC(=O)N1CCc1cccs1] | Ethyl 2-(N-(2-(1H-indol-3-yl)ethyl)-2-(3,6-dioxo-1,4-bis(2-(thiophen-2-yl)ethyl)piperazin-2-yl)acetamido)acetate | B | 3.937 621 |
| Ic.16.11 | 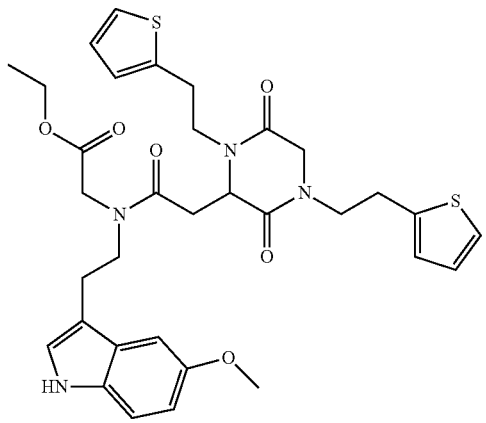 [SMILES: CCOC(=O)CN(CCc1c[nH]c2ccc(OC)cc12)C(=O)CC1C(=O)N(CCc2cccs2)CC(=O)N1CCc1cccs1] | Ethyl 2-(2-(3,6-dioxo-1,4-bis(2-(thiophen-2-yl)ethyl)piperazin-2-yl)-N-(2-(5-methoxy-1H-indol-3-yl)ethyl)acetamido)acetate | B | 3.857 651 |

| | | | | |
|---|---|---|---|---|
| Ic.16.13 | 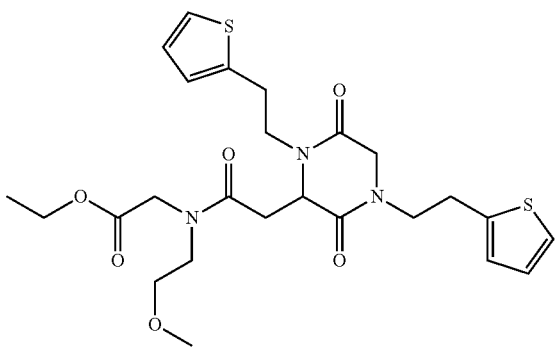 [SMILES: CCOC(=O)CN(CCOC)C(=O)CC1C(=O)N(CCc2cccs2)CC(=O)N1CCc1cccs1] | Ethyl 2-(2-(3,6-dioxo-1,4-bis(2-(thiophen-2-yl)ethyl)piperazin-2-yl)-N-(2-methoxy-ethyl)acetamido)acetate | B | 3.530 536 |
| Ic.16.19.2 | 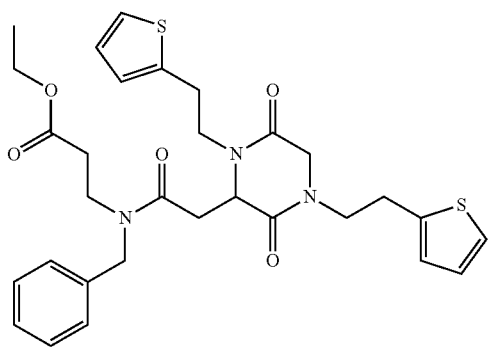 [SMILES: CCOC(=O)CCN(Cc1ccccc1)C(=O)CC1C(=O)N(CCc2cccs2)CC(=O)N1CCc1cccs1] | Ethyl 3-(N-benzyl-2-(3,6-dioxo-1,4-bis(2-(thiophen-2-yl)ethyl)piperazin-2-yl)acetamido)propanoate | B | 4.040 582 |
| Ic.21.2 | 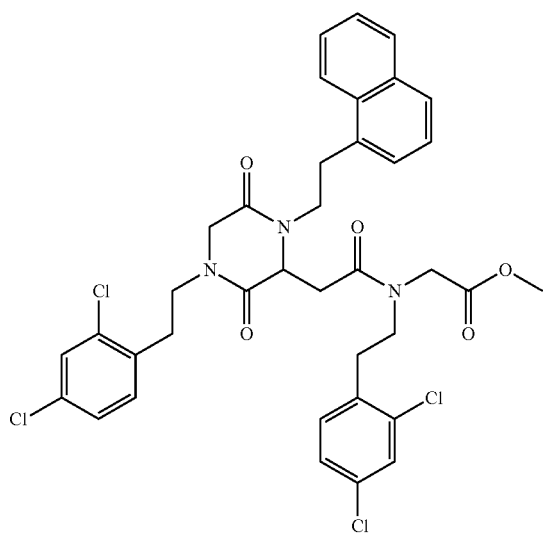 [SMILES: COC(=O)CN(CCc1ccc(Cl)cc1Cl)C(=O)CC1C(=O)N(CCc2ccc(Cl)cc2Cl)CC(=O)N1CCc1cccc2ccccc12] | Methyl 2-(N-(2,4-dichloro-phenethyl)-2-(4-(2,4-dichloro-phenethyl)-1-(2-(naphthalen-1-yl)ethyl)-3,6-dioxo-piperazin-2-yl)acetamido)acetate | B | 5.087 743 745 |

Compounds of formula Id

Id.1.2 N-(2,4-dichlorophenethyl)-2-(4-(2,4-dichlorophenethyl)-1-(3,3-diphenylpropyl)-3,6-dioxopiperazin-2-yl)acetamide

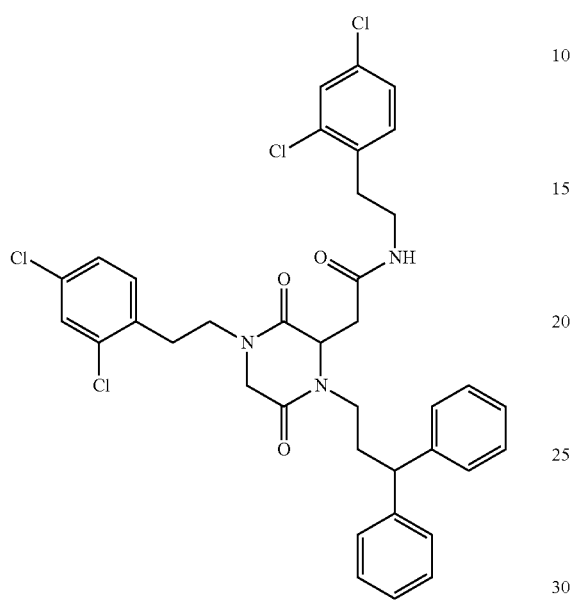

Acid X.1 (100 mg, 1 eq.) was added to a solution of 2,4-dichlorophenethylamine (IVc, 28 µL, 1 eq.), DIC (85 µL, 3 eq.) and triethylamine (80 µL, 3 eq.) in 2 ml of DCM and the reaction mixture was stirred at room temperature for 3 h. The crude reaction product was neutralized with NaOH and was extracted with DCM. The organic extracts were washed with saturated sodium chloride, dried on anhydrous $MgSO_4$ and evaporated at reduced pressure to obtain 96 mg of the desired compound Id.1.2 (73% yield, 89% purity). HRMS (M+H)$^+$ calculated for $C_{37}H_{36}Cl_4N_3O_3$, 710.1511, experimental, 710.1522.

| Ex | Structure | Compound | HRMS (M + H)$^+$: Calculated | Experimental |
|---|---|---|---|---|
| Id.2.2 | 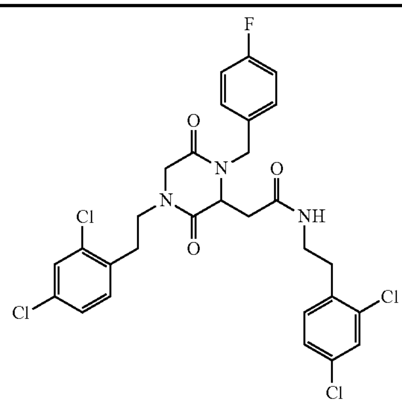 | N-(2,4-dichlorophenethyl)-2-(4-(2,4-dichlorophenethyl)-1-(4-fluorobenzyl)-3,6-dioxopiperazin-2-yl)acetamide | $C_{29}H_{26}Cl_4FN_3O_3$ 624.0791 | 624.25 |
| Id.3.2 | 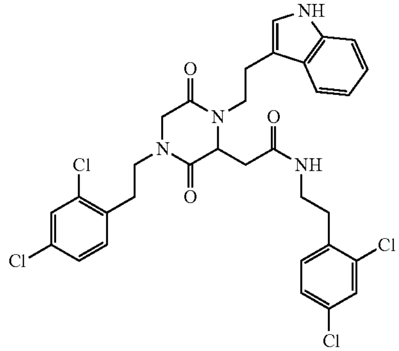 [SMILES: O=C(CC1C(=O)N(CCc2ccc(Cl)cc2Cl)CC(=O)N1CCc1c[nH]c2ccccc12)NCCc1ccc(Cl)cc1Cl] | 2-(1-(2-(1H-indol-3-yl)ethyl)-4-(2,4-dichlorophenethyl)-3,6-dioxopiperazin-2-yl)-N-(2,4-dichlorophenethyl)acetamide | $C_{32}H_{30}Cl_4N_4O_3$ 659.115 | 659.1163 |

-continued
| Id.4.2 | 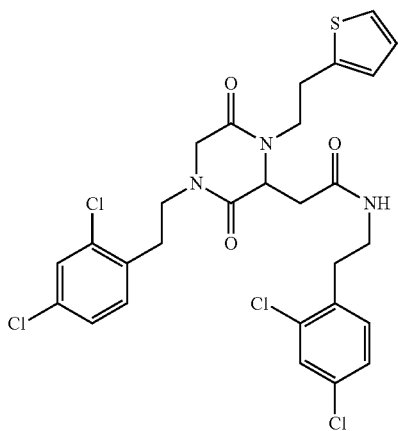 [SMILES: O=C(CC1C(=O)N(CCc2ccc(Cl)cc2Cl)CC(=O)N1CCc1cccs1)NCCc1ccc(Cl)cc1Cl] | N-(2,4-dichlorophen-ethyl)-2-(4-(2,4-dichlorophen-ethyl)-3,6-dioxo-1-(2-(thiophen-2-yl)ethyl)piperazin-2-yl)acetamide | $C_{28}H_{27}Cl_4N_3O_3S$ 626.0605 | 626.0589 |
| --- | --- | --- | --- | --- |
| Id.5.2 | 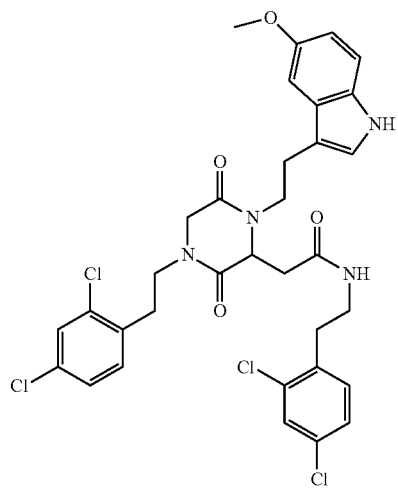 [SMILES: COc1ccc2[nH]cc(CCN3C(=O)CN(CCc4ccc(Cl)cc4Cl)C(=O)C3CC(=O)NCCc3ccc(Cl)cc3Cl)c2c1] | N-(2,4-dichlorophen-ethyl)-2-(4-(2,4-dichlorophenethyl)-1-(2-(5-methoxy-1H-indol-3-yl)ethyl)-3,6-dioxopiperazin-2-yl)acetamide | $C_{33}H_{32}Cl_4N_4O_4$ 689.1256 | 689.30 |
| Id.6.2 | 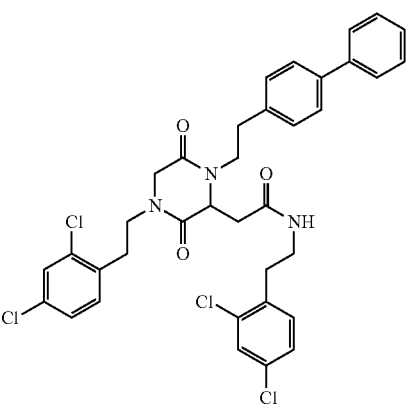 [SMILES: O=C(CC1C(=O)N(CCc2ccc(Cl)cc2Cl)CC(=O)N1CCc1ccc(-c2ccccc2)cc1)NCCc1ccc(Cl)cc1Cl] | 2-(1-(2-([1,1'-biphenyl]-4-yl)ethyl)-4-(2,4-dichlorophenethyl)-3,6-dioxopiperazin-2-yl)-N-(2,4-dichlorophen-ethyl)acetamide | $C_{36}H_{33}Cl_4N_3O_3$ 696.1354 | 696.1335 |

-continued

| Ex. | Structure | Compound | | | |
|---|---|---|---|---|---|
| Id.7.2 | 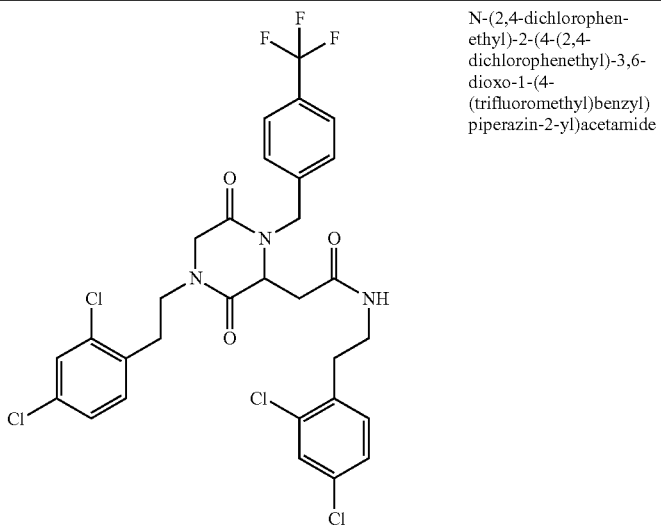 | N-(2,4-dichlorophen-ethyl)-2-(4-(2,4-dichlorophenethyl)-3,6-dioxo-1-(4-(trifluoromethyl)benzyl)piperazin-2-yl)acetamide | $C_{30}H_{26}Cl_4F_3N_3O_3$ 674.0759 | | 674.35 |

| Ex. | Structure | Compound | method | tr | m/z |
|---|---|---|---|---|---|
| Id.4.1 | 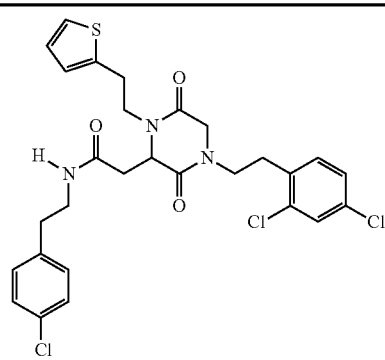 | N-(4-chlorophen-ethyl)-2-(4-(2,4-dichlorophenethyl)-3,6-dioxo-1-(2-(thiophen-2-yl)ethyl)piperazin-2-yl)acetamide | C | 4.869 | 592 594 |
| Id.4.3 | 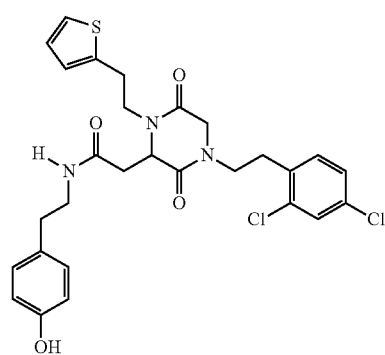 [SMILES: O=C(CC1C(=O)N(CCc2ccc(Cl)cc2Cl)CC(=O)N1CCc1cccs1)NCCc1ccc(O)cc1] | 2-(4-(2,4-dichlorophen-ethyl)-3,6-dioxo-1-(2-(thiophen-2-yl)ethyl)piperazin-2-yl)-N-(4-hydroxyphenethyl)acetamide | C | 4.193 | 574 576 |
| Id.4.4 | 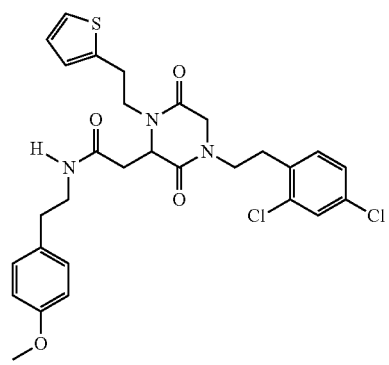 [SMILES: COc1ccc(CCNC(=O)CC2C(=O)N(CCc3ccc(Cl)cc3Cl)CC(=O)N2CCc2cccs2)cc1] | 2-(4-(2,4-dichlorophen-ethyl)-3,6-dioxo-1-(2-(thiophen-2-yl)ethyl)piperazin-2-yl)-N-(4-methoxyphenethyl)acetamide | C | 4.62 | 588 590 |

| | | | | | |
|---|---|---|---|---|---|
| Id.4.5 | 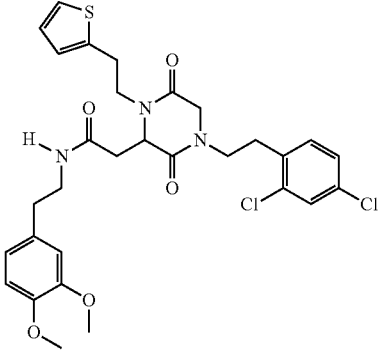 [SMILES: COc1ccc(CCNC(=O)CC2C(=O)N(CCc3ccc(Cl)cc3Cl)CC(=O)N2CCc2cccs2)cc1OC] | 2-(4-( 2,4-dichlorophen-ethyl)-3,6-dioxo-1-(2-(thiophen-2-yl)ethyl)piperazin-2-yl)-N-(3,4-dimethoxy-phenethyl)acetamide | C | 4.455 | 618 620 |
| Id.4.6 | 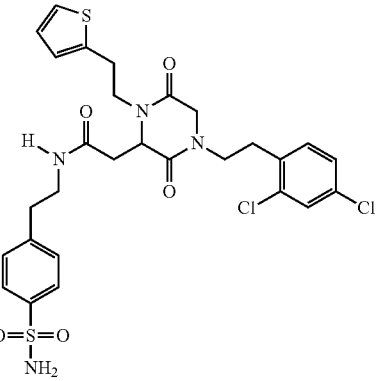 | 2-(4-(2,4-dichlorophen-ethyl)-3,6-dioxo-1-(2-(thiophen-2-yl)ethyl)piperazin-2-yl)-N-(4-sulfamoylphenethyl)acetamide | C | 4.079 | 637 639 |
| Id.4.7 | 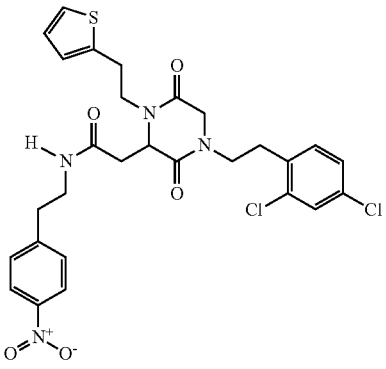 [SMILES: O=C(CC1C(=O)N(CCc2ccc(Cl)cc2Cl)CC(=O)N1CCc1cccs1)NCCc1ccc([N+](=O)[O-])cc1] | 2-(4-(2,4-dichlorophen-ethyl)-3,6-dioxo-1-(2-(thiophen-2-yl)ethyl)piperazin-2-yl)-N-(4-nitrophenethyl)acetamide | C | 4.599 | 603 605 |
| Id.4.8 | 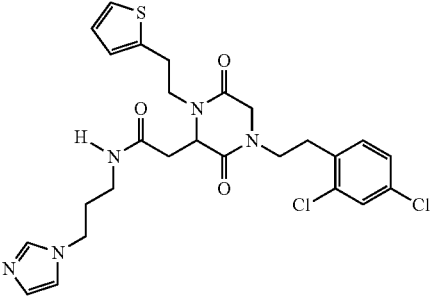 [SMILES: O=C(CC1C(=O)N(CCc2ccc(Cl)cc2Cl)CC(=O)N1CCc1cccs1)NCCCn1ccnc1] | N-(3-(1H-imidazol-1-yl)propyl)-2-(4-(2,4-dichlorophenethyl)-3,6-dioxo-1-(2-(thiophen-2-yl)ethyl)piperazin-2-yl)acetamide | C | 3.410 | 543 545 |

-continued

| | | | | | |
|---|---|---|---|---|---|
| Id.4.9 | 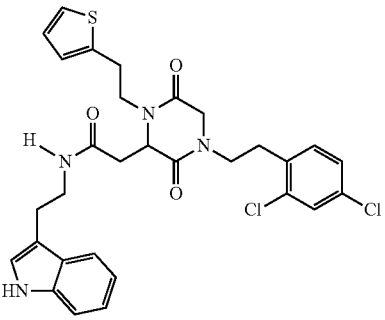 [SMILES: O=C(CC1C(=O)N(CCc2ccc(Cl)cc2Cl)CC(=O)N1CCc1cccs1)NCCc1c[nH]c2ccccc12] | N-(2-(1H-indol-3-yl)ethyl)-2-(4-(2,4-dichlorophenethyl)-3,6-dioxo-1-(2-(thiophen-2-yl)ethyl)piperazin-2-yl)acetamide | C | 4.565 | 597 599 |
| Id.4.11 | 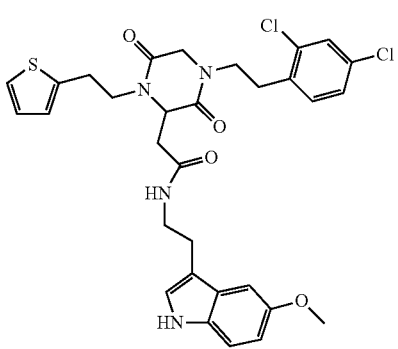 [SMILES: COc1ccc2[nH]cc(CCNC(=O)CC3C(=O)N(CCc4ccc(Cl)cc4Cl)CC(=O)N3CCc3cccs3)c2c1] | 3-(2-(3-(2-aminoethyl)-5-methoxy-1H-indol-1-yl)-2-oxoethyl)-1-(2,4-dichlorophenethyl)-4-(2-(thiophen-2-yl)ethyl)piperazine-2,5-dione | C | 4.498 | 627 629 |
| Id.4.12 | 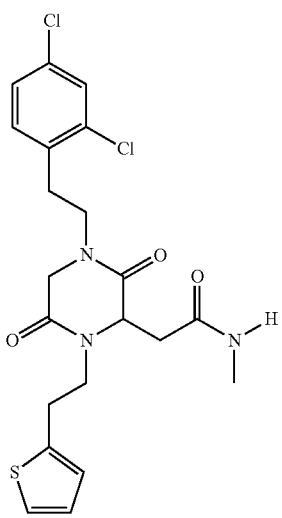 [SMILES: CNC(=O)CC1C(=O)N(CCc2ccc(Cl)cc2Cl)CC(=O)N1CCc1cccs1] | 2-(4-(2,4-dichlorophen-ethyl)-3,6-dioxo-1-(2-(thiophen-2-yl)ethyl)piperazin-2-yl)-N-methylacetamide | C | 3.988 | 468 470 |
| Id.4.13 | 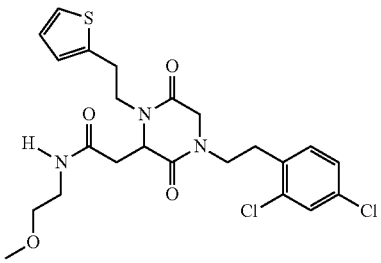 [SMILES: COCCNC(=O)CC1C(=O)N(CCc2ccc(Cl)cc2Cl)CC(=O)N1CCc1cccs1] | 2-(4-(2,4-dichlorophen-ethyl)-3,6-dioxo-1-(2-(thiophen-2-yl)ethyl)piperazin-2-yl)-N-(2-methoxyethyl)acetamide | C | 4.086 | 512 514 |

-continued

| | | | | | |
|---|---|---|---|---|---|
| Id.4.14 | 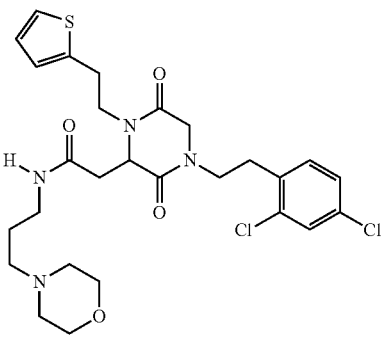 [SMILES: O=C(CC1C(=O)N(CCc2ccc(Cl)cc2Cl)CC(=O)N1CCc1cccs1)NCCCN1CCOCC1] | 2-(4-(2,4-dichlorophen-ethyl)-3,6-dioxo-1-(2-(thiophen-2-yl)ethyl)piperazin-2-yl)-N-(3-morpholinopropyl)acetamide | C | 3.440 | 581 583 |
| Id.4.15 | 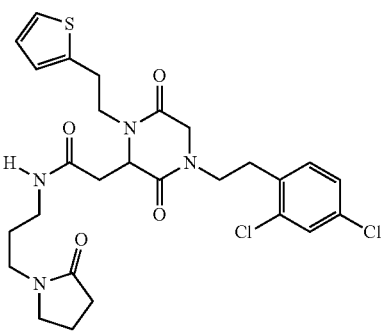 [SMILES: O=C(CC1C(=O)N(CCc2ccc(Cl)cc2Cl)CC(=O)N1CCc1cccs1)NCCCN1CCCC1=O] | 2-(4-(2,4-dichlorophen-ethyl)-3,6-dioxo-1-(2-(thiophen-2-yl)ethyl)piperazin-2-yl)-N-(3-(2-oxopyrrolidin-1-yl)propyl)acetamide | C | 3.953 | 579 581 |
| Id.4.19 | 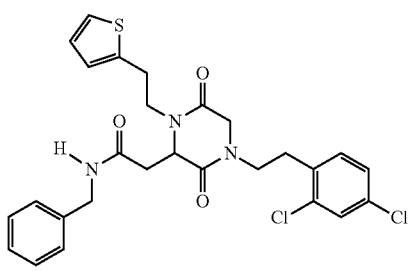 [SMILES: O=C(CC1C(=O)N(CCc2ccc(Cl)cc2Cl)CC(=O)N1CCc1cccs1)NCc1ccccc1] | N-benzyl-2-(4-(2,4-dichlorophenethyl)-3,6-dioxo-1-(2-(thiophen-2-yl)ethyl)piperazin-2-yl)acetamide | C | 4.584 | 544 546 |
| Id.4.23 | 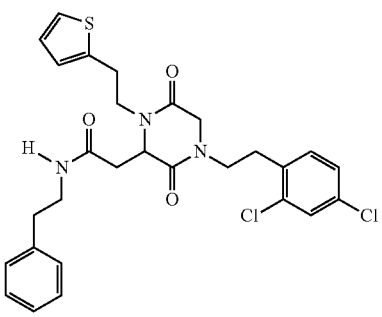 [SMILES: O=C(CC1C(=O)N(CCc2ccc(Cl)cc2Cl)CC(=O)N1CCc1cccs1)NCCc1ccccc1] | 2-(4-(2,4-dichlorophen-ethyl)-3,6-dioxo-1-(2-(thiophen-2-yl)ethyl)piperazin-2-yl)-N-phenethylacetamide | C | 4.661 | 558 560 |
| Id.4.24 | 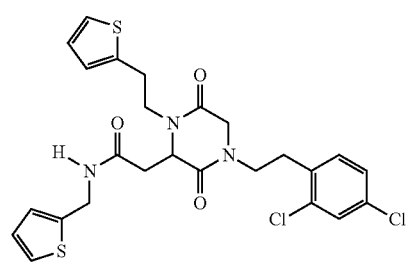 [SMILES: O=C(CC1C(=O)N(CCc2ccc(Cl)cc2Cl)CC(=O)N1CCc1cccs1)NCc1cccs1] | 2-(4-(2,4-dichlorophen-ethyl)-3,6-dioxo-1-(2-(thiophen-2-yl)ethyl)piperazin-2-yl)-N-(thiophen-2-ylmethyl)acetamide | C | 4.501 | 550 552 |

-continued

| | | | | | |
|---|---|---|---|---|---|
| Id.4.25 | | 2-(4-(2,4-dichlorophenethyl)-3,6-dioxo-1-(2-(thiophen-2-yl)ethyl)piperazin-2-yl)-N-(3-phenylpropyl)acetamide | C | 4.796 | 572 574 |
| Id.4.26 | | 2-(4-(2,4-dichlorophenethyl)-3,6-dioxo-1-(2-(thiophen-2-yl)ethyl)piperazin-2-yl)-N-(prop-2-yn-1-yl)acetamide | C | 4.175 | 492 494 |
| Id.4.27 | | N-allyl-2-(4-(2,4-dichlorophenethyl)-3,6-dioxo-1-(2-(thiophen-2-yl)ethyl)piperazin-2-yl)acetamide | C | 4.269 | 494 496 |
| Id.13.1 | | N-(4-chlorophenethyl)-2-(3,6-dioxo-4-(2-(pyridin-2-yl)ethyl)-1-(2-(thiophen-2-yl)ethyl)piperazin-2-yl)acetamide | C | 3.382 | 525 |
| Id.13.2 | | N-(2,4-dichlorophenethyl)-2-(3,6-dioxo-4-(2-(pyridin-2-yl)ethyl)-1-(2-(thiophen-2-yl)ethyl)piperazin-2-yl)acetamide | C | 3.561 | 559 561 |

-continued

| | | | | | |
|---|---|---|---|---|---|
| Id.13.5 | 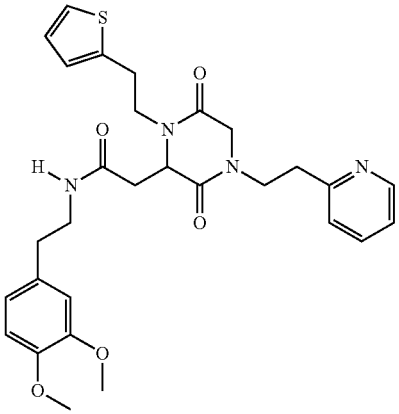 [SMILES: COc1ccc(CCNC(=O)CC2C(=O)N(CCc3ccccn3)CC(=O)N2CCc2cccs2)cc1OC] | N-(3,4-dimethoxyphenethyl)-2-(3,6-dioxo-4-(2-(pyridin-2-yl)ethyl)-1-(2-(thiophen-2-yl)ethyl)piperazin-2-yl)acetamide | C | 3.018 | 551 |
| Id.13.7 | 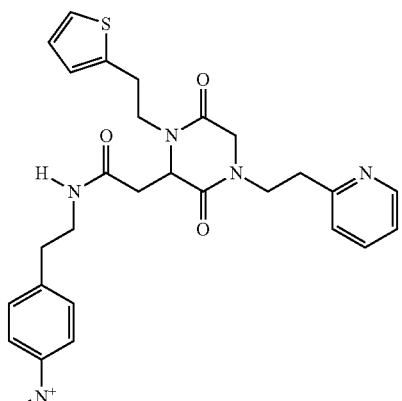 | 2-(3,6-dioxo-4-(2-(pyridin-2-yl)ethyl)-1-(2-(thiophen-2-yl)ethyl)piperazin-2-yl)-N-(4-nitrophenethyl)acetamide | C | 3.149 | 536 |
| Id.13.9 | 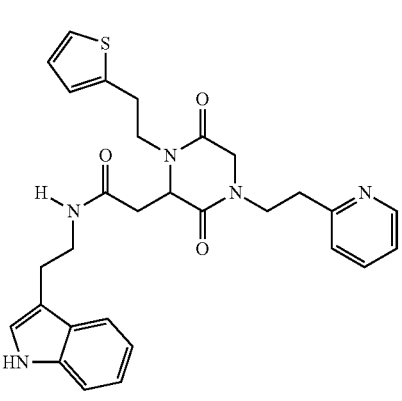 [SMILES: O=C(CC1C(=O)N(CCc2ccccn2)CC(=O)N1CCc1cccs1)NCCc1c[nH]c2ccccc12] | N-(2-(1H-indol-3-yl)ethyl)-2-(3,6-dioxo-4-(2-(pyridin-2-yl)ethyl)-1-(2-(thiophen-2-yl)ethyl)piperazin-2-yl)acetamide | C | 3.170 | 530 |
| Id.13.11 | 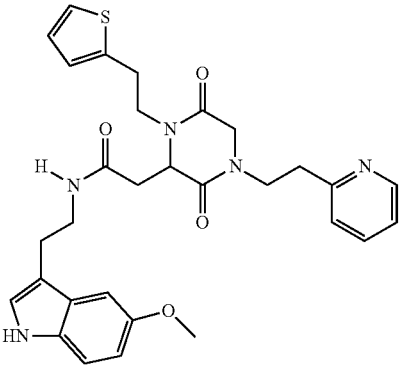 [SMILES: COc1ccc2[nH]cc(CCNC(=O)CC3C(=O)N(CCc4ccccn4)CC(=O)N3CCc3cccs3)c2c1] | 2-(3,6-dioxo-4-(2-(pyridin-2-yl)ethyl)-1-(2-(thiophen-2-yl)ethyl)piperazin-2-yl)-N-(2-(5-methoxy-1H-indol-3-yl)ethyl)acetamide | C | 3.123 | 560 |

-continued
| Id.14.1 | 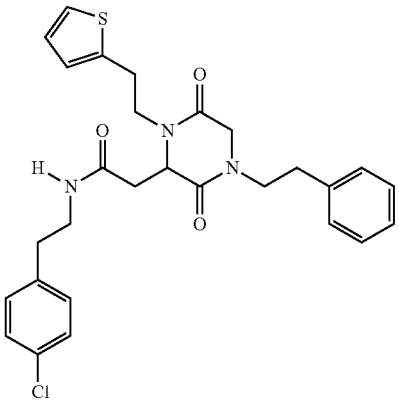 [SMILES: O=C(CC1C(=O)N(CCc2ccccc2)CC(=O)N1CCc1cccs1)NCCc1ccc(Cl)cc1] | N-(4-chlorophenethyl)-2-(3,6-dioxo-4-phenethyl-1-(2-(thiophen-2-yl)ethyl)piperazin-2-yl)acetamide | B | 3.931 | 524 526 |
| Id.14.2 | 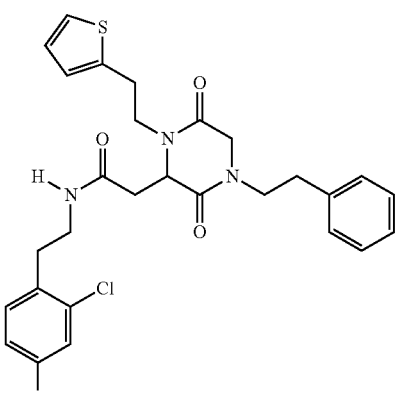 | N-(2,4-dichlorophen-ethyl)-2-(3,6-dioxo-4-phenethyl-1-(2-(thiophen-2-yl)ethyl)piperazin-2-yl)acetamide | B | 4.163 | 558 560 |
| Id.14.3 | 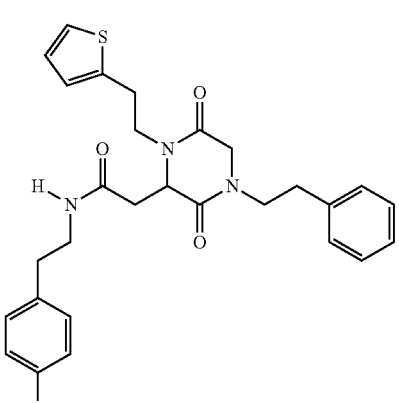 | 2-(3,6-dioxo-4-phenethyl-1-(2-(thiophen-2-yl)ethyl)piperazin-2-yl)-N-(4-hydroxyphen-ethyl)acetamide | B | 3.225 | 506 |
| Id.14.4 | 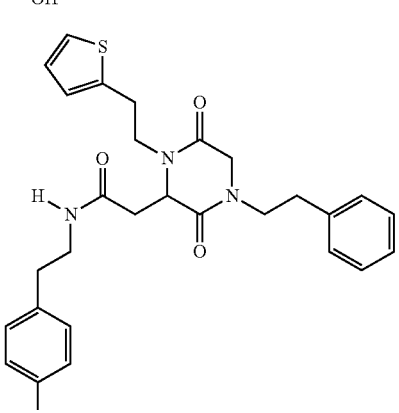 | 2-(3,6-dioxo-4-phenethyl-1-(2-(thiophen-2-yl)ethyl)piperazin-2-yl)-N-(4-methoxyphenethyl)acetamide | B | 3.671 | 520 |

-continued
| Id.14.5 | 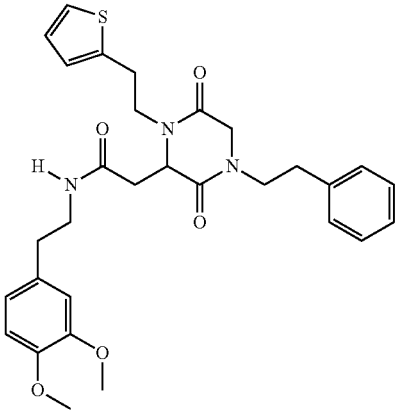 [SMILES: COc1ccc(CCNC(=O)CC2C(=O)N(CCc3ccccc3)CC(=O)N2CCc2cccs2)cc1OC] | N-(3,4-dimethoxyphen-ethyl)-2-(3,6-dioxo-4-phenethyl-1-(2-(thiophen-2-yl)ethyl)piperazin-2-yl)acetamide | B | 3.487 | 550 |
| Id.14.6 | 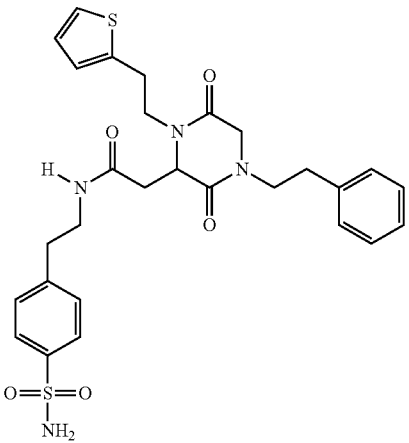 [SMILES: NS(=O)(=O)c1ccc(CCNC(=O)CC2C(=O)N(CCc3ccccc3)CC(=O)N2CCc2cccs2)cc1] | 2-(3,6-dioxo-4-phenethyl-1-(2-(thiophen-2-yl)ethyl)piperazin-2-yl)-N-(4-sulfamoylphenethyl)acetamide | B | 3.112 | 569 |
| Id.14.7 | 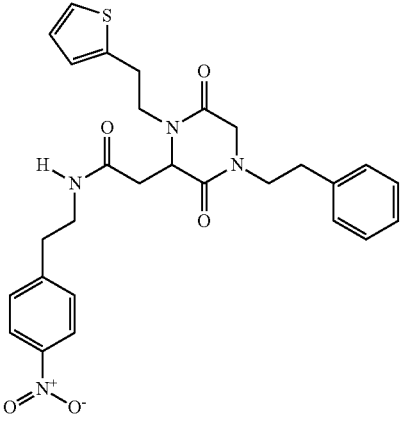 [SMILES: O=C(CC1C(=O)N(CCc2ccccc2)CC(=O)N1CCc1cccs1)NCCc1ccc([N+](=O)[O-])cc1] | 2-(3,6-dioxo-4-phenethyl-1-(2-(thiophen-2-yl)ethyl)piperazin-2-yl)-N-(4-nitrophenethyl)acetamide | B | 4.184 | 535 |
| Id.14.8 | 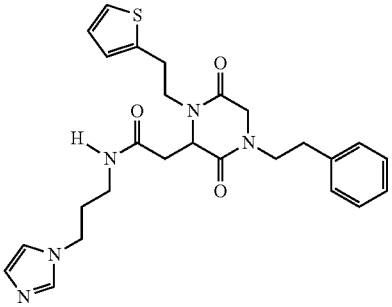 [SMILES: O=C(CC1C(=O)N(CCc2ccccc2)CC(=O)N1CCc1cccs1)NCCCn1ccnc1] | N-(3-(1H-imidazol-1-yl)propyl)-2-(3,6-dioxo-4-phenethyl-1-(2-(thiophen-2-yl)ethyl)piperazin-2-yl)acetamide | B | 2.456 | 494 |

| | | | | | |
|---|---|---|---|---|---|
| Id.14.9 | 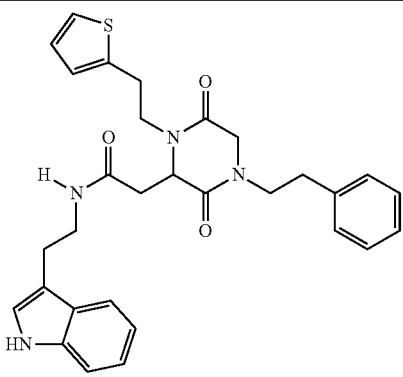 | N-(2-(1H-indol-3-yl)ethyl)-2-(3,6-dioxo-4-phenethyl-1-(2-(thiophen-2-yl)ethyl)piperazin-2-yl)acetamide | B | 3.626 | 529 |
| Id.14.11 | 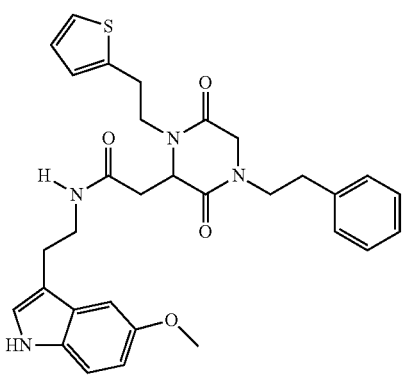 [SMILES: COc1ccc2[nH]cc(CCNC(=O)CC3C(=O)N(CCc4ccccc4)CC(=O)N3CCc3cccs3)c2c1] | 2-(3,6-dioxo-4-phenethyl-1-(2-(thiophen-2-yl)ethyl)piperazin-2-yl)-N-(2-(5-methoxy-1H-indol-3-yl)ethyl)acetamide | B | 3.552 | 559 |
| Id.14.13 | 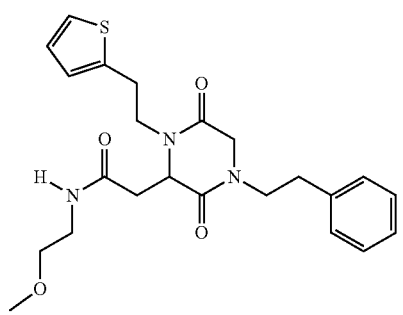 [SMILES: COCCNC(=O)CC1C(=O)N(CCc2ccccc2)CC(=O)N1CCc1cccs1] | 2-(3,6-dioxo-4-phenethyl-1-(2-(thiophen-2-yl)ethyl)piperazin-2-yl)-N-(2-methoxyethyl)acetamide | B | 3.044 | 444 |
| Id.14.19 | 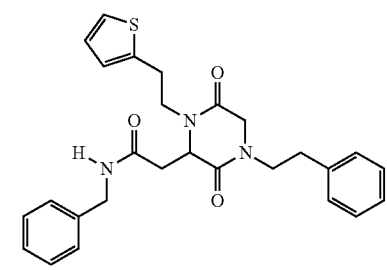 [SMILES: O=C(CC1C(=O)N(CCc2ccccc2)CC(=O)N1CCc1cccs1)NCc1ccccc1] | N-benzyl-2-(3,6-dioxo-4-phenethyl-1-(2-(thiophen-2-yl)ethyl)piperazin-2-yl)acetamide | B | 3.600 | 476 |

-continued
| | | | | | |
|---|---|---|---|---|---|
| Id.15.1 | 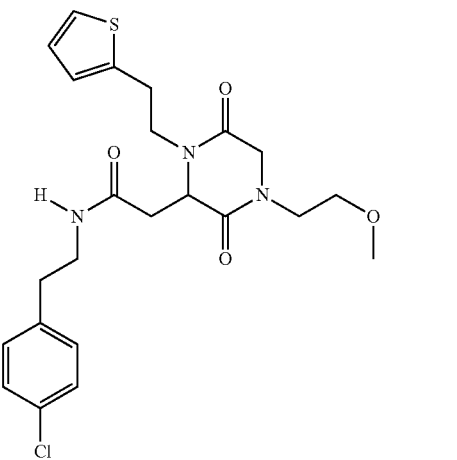 [SMILES: COCCN1CC(=O)N(CCc2cccs2)C(CC(=O)NCCc2ccc(Cl)cc2)C1=O] | N-(4-chlorophenethyl)-2-(4-(2-methoxyethyl)-3,6-dioxo-1-(2-(thiophen-2-yl)ethyl)piperazin-2-yl)acetamide | B | 3.346 | 478 480 |
| Id.15.2 | 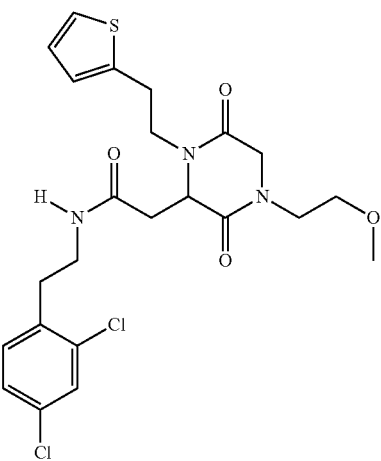 [SMILES: COCCN1CC(=O)N(CCc2cccs2)C(CC(=O)NCCc2ccc(Cl)cc2Cl)C1=O] | N-(2,4-dichlorophen-ethyl)-2-(4-(2-methoxyethyl)-3,6-dioxo-1-(2-(thiophen-2-yl)ethyl)piperazin-2-yl)acetamide | B | 3.596 | 512 514 |
| Id.15.3 | 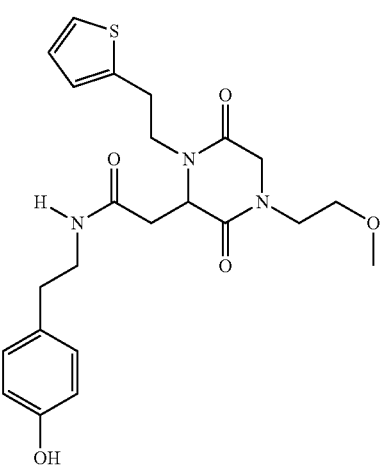 [SMILES: COCCN1CC(=O)N(CCc2cccs2)C(CC(=O)NCCc2ccc(O)cc2)C1=O] | N-(4-hydroxyphenethyl)-2-(4-(2-methoxyethyl)-3,6-dioxo-1-(2-(thiophen-2-yl)ethyl)piperazin-2-yl)acetamide | B | 2.547 | 460 |

-continued
| Id.15.4 | 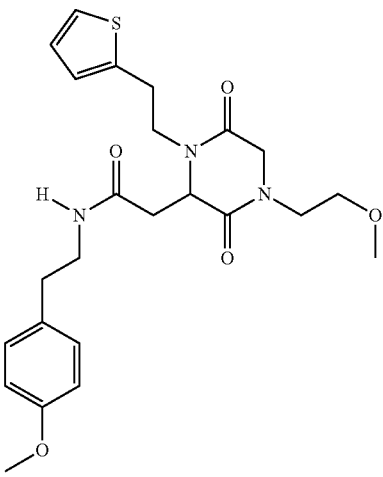 [SMILES: COCCN1CC(=O)N(CCc2cccs2)C(CC(=O)NCCc2ccc(OC)cc2)C1=O] | 2-(4-(2-methoxyethyl)-3,6-dioxo-1-(2-(thiophen-2-yl)ethyl)piperazin-2-yl)-N-(4-methoxyphenethyl)acetamide | B | 3.046 | 474 |
| Id.15.5 | 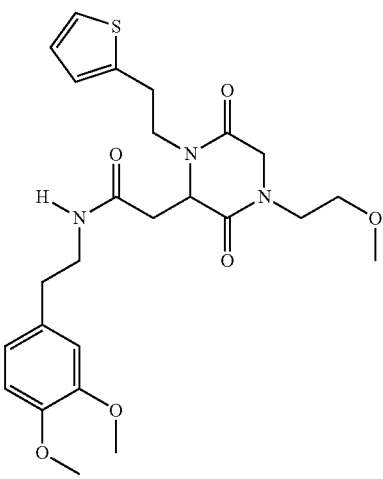 [SMILES: COCCN1CC(=O)N(CCc2cccs2)C(CC(=O)NCCc2ccc(OC)c(OC)c2)C1=O] | N-(3,4-dimethoxyphenethyl)-2-(4-(2-methoxyethyl)-3,6-dioxo-1-(2-(thiophen-2-yl)ethyl)piperazin-2-yl)acetamide | B | 2.850 | 504 |
| Id.15.6 | 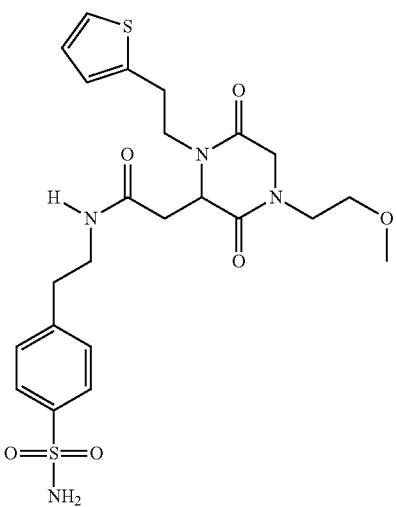 [SMILES: COCCN1CC(=O)N(CCc2cccs2)C(CC(=O)NCCc2ccc(S(N)(=O)=O)cc2)C1=O] | 2-(4-(2-methoxyethyl)-3,6-dioxo-1-(2-(thiophen-2-yl)ethyl)piperazin-2-yl)-N-(4-sulfamoylphenethyl)acetamide | B | 2.433 | 523 |

-continued
| Id.15.7 | 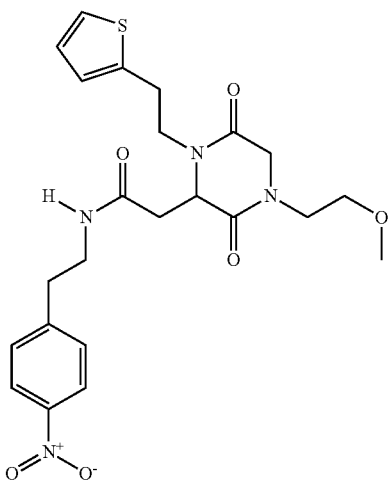 [SMILES: COCCN1CC(=O)N(CCc2cccs2)C(CC(=O)NCCc2ccc([N+](=O)[O-])cc2)C1=O] | 2-(4-(2-methoxyethyl)-3,6-dioxo-1-(2-(thiophen-2-yl)ethyl)piperazin-2-yl)-N-(4-nitrophenethyl)acetamide | B | 3.041 | 489 |
|---|---|---|---|---|---|
| Id.15.8 | 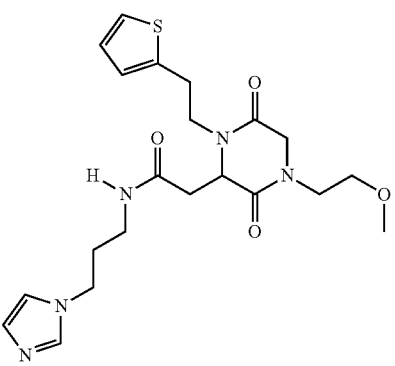 [SMILES: COCCN1CC(=O)N(CCc2cccs2)C(CC(=O)NCCCn2ccnc2)C1=O] | N-(3-(1H-imidazol-1-yl)propyl)-2-(4-(2-methoxyethyl)-3,6-dioxo-1-(2-(thiophen-2-yl)ethyl)piperazin-2-yl)acetamide | B | 1.847 | 448 |
| Id.15.9 | 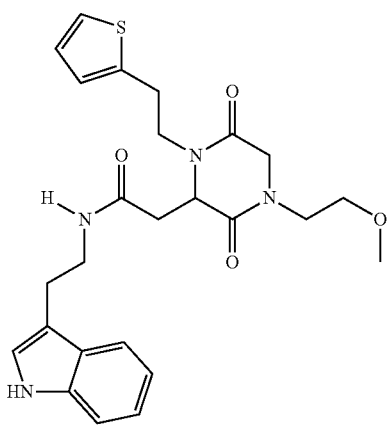 [SMILES: COCCN1CC(=O)N(CCc2cccs2)C(CC(=O)NCCc2c[nH]c3ccccc23)C1=O] | N-(2-(1H-indol-3-yl)ethyl)-2-(4-(2-methoxy-ethyl)-3,6-dioxo-1-(2-(thiophen-2-yl)ethyl)piperazin-2-yl)acetamide | B | 3.033 | 483 |

-continued
| | | | | | |
|---|---|---|---|---|---|
| Id.15.11 | 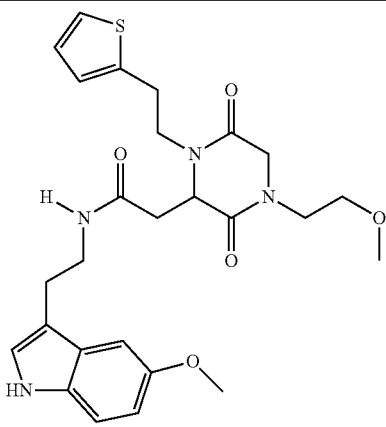 | N-(2-(5-methoxy-1H-indol-3-yl)ethyl)-2-(4-(2-methoxyethyl)-3,6-dioxo-1-(2-(thiophen-2-yl)ethyl)piperazin-2-yl)acetamide | B | 2.962 | 513 |
| Id.15.13 | 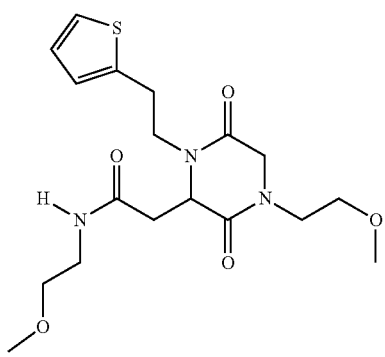 | N-(2-methoxyethyl)-2-(4-(2-methoxyethyl)-3,6-dioxo-1-(2-(thiophen-2-yl)ethyl)piperazin-2-yl)acetamide | B | 2.275 | 398 |
| Id.15.19 | 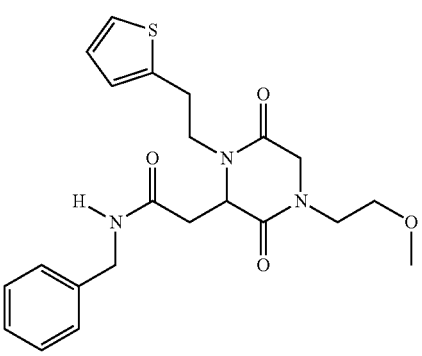 [SMILES: COCCN1CC(=O)N(CCc2cccs2)C(CC(=O)NCc2ccccc2)C1=O] | N-benzyl-2-(4-(2-methoxyethyl)-3,6-dioxo-1-(2-(thiophen-2-yl)ethyl)piperazin-2-yl)acetamide | B | 2.919 | 430 |
| Id.16.1 | 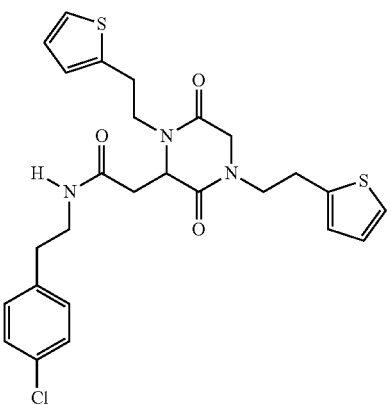 [SMILES: O=C(CC1C(=O)N(CCc2cccs2)CC(=O)N1CCc1cccs1)NCCc1ccc(Cl)cc1] | N-(4-chlorophenethyl)-2-(3,6-dioxo-1,4-bis(2-(thiophen-2-yl)ethyl)piperazin-2-yl)acetamide | B | 3.861 | 530<br>532 |

-continued

| Id.16.2 | | N-(2,4-dichlorophen-ethyl)-2-(3,6-dioxo-1,4-bis(2-(thiophen-2-yl)ethyl)piperazin-2-yl)acetamide | B | 4.094 | 564 566 |
|---|---|---|---|---|---|
| Id.16.3 | | 2-(3,6-dioxo-1,4-bis(2-(thiophen-2-yl)ethyl)piperazin-2-yl)-N-(4-hydroxyphenethyl)acetamide | B | 3.145 | 512 |
| Id.16.4 | | 2-(3,6-dioxo-1,4-bis(2-(thiophen-2-yl)ethyl)piperazin-2-yl)-N-(4-methoxyphenethyl)acetamide | B | 3.600 | 526 |
| Id.16.5 | | N-(3,4-dimethoxyphen-ethyl)-2-(3,6-dioxo-1,4-bis(2-(thiophen-2-yl)ethyl)piperazin-2-yl)acetamide | B | 3.409 | 556 |

| | | | | | |
|---|---|---|---|---|---|
| Id.16.6 | 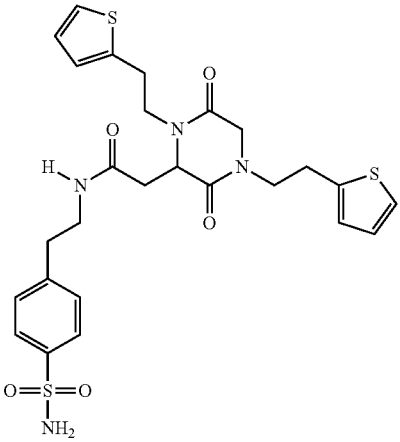 [SMILES: NS(=O)(=O)c1ccc(CCNC(=O)CC2C(=O)N(CCc3cccs3)CC(=O)N2CCc2cccs2)cc1] | 2-(3,6-dioxo-1,4-bis(2-(thiophen-2-yl)ethyl)piperazin-2-yl)-N-(4-sulfamoylphenethyl)acetamide | B | 3.029 | 575 |
| Id.16.7 | 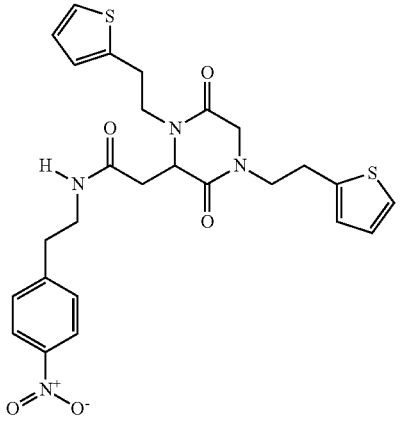 [SMILES: O=C(CC1C(=O)N(CCc2cccs2)CC(=O)N1CCc1cccs1)NCCc1ccc([N+](=O)[O-])cc1] | 2-(3,6-dioxo-1,4-bis(2-(thiophen-2-yl)ethyl)piperazin-2-yl)-N-(4-nitrophenethyl)acetamide | B | 3.578 | 541 |
| Id.16.8 | 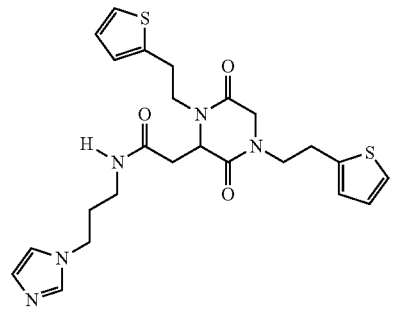 [SMILES: O=C(CC1C(=O)N(CCc2cccs2)CC(=O)N1CCc1cccs1)NCCCn1ccnc1] | N-(3-(1H-imidazol-1-yl)propyl)-2-(3,6-dioxo-1,4-bis(2-(thiophen-2-yl)ethyl)piperazin-2-yl)acetamide | B | 2.377 | 500 |
| Id.16.9 | 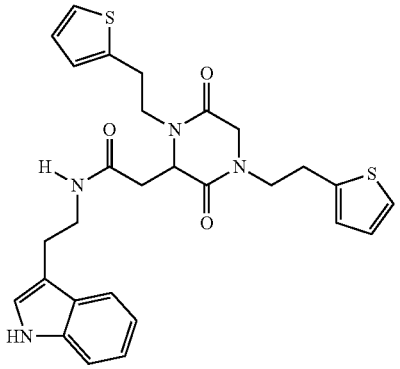 [SMILES: O=C(CC1C(=O)N(CCc2cccs2)CC(=O)N1CCc1cccs1)NCCc1c[nH]c2ccccc12] | N-(2-(1H-indol-3-yl)ethyl)-2-(3,6-dioxo-1,4-bis(2-(thiophen-2-yl)ethyl)piperazin-2-yl)acetamide | B | 3.554 | 535 |

-continued
| | | | | | |
|---|---|---|---|---|---|
| Id.16.11 | 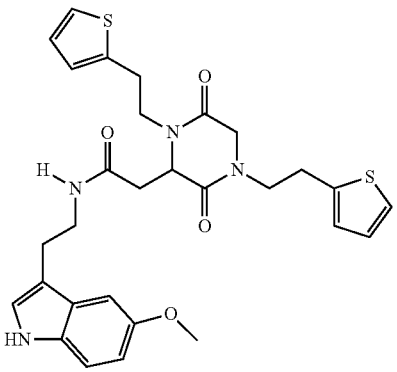 [SMILES: COc1ccc2[nH]cc(CCNC(=O)CC3C(=O)N(CCc4cccs4)CC(=O)N3CCc3cccs3)c2c1] | 2-(3,6-dioxo-1,4-bis (2-(thiophen-2-yl)ethyl) piperazin-2-yl)-N-(2- (5-methoxy-1H-indol-3- yl)ethyl)acetamide | B | 3.481 | 565 |
| Id.16.13 | 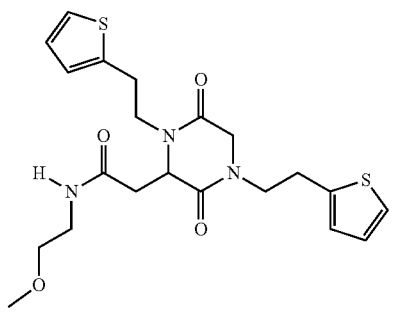 [SMILES: COCCNC(=O)CC1C(=O)N(CCc2cccs2)CC(=O)N1CCc1cccs1] | 2-(3,6-dioxo-1,4-bis(2- (thiophen-2-yl)ethyl) piperazin-2-yl)-N-(2- methoxyethyl) acetamide | B | 2.948 | 450 |
| Id.16.19 | 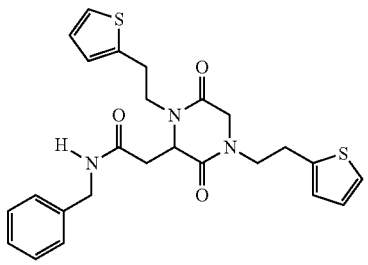 [SMILES: O=C(CC1C(=O)N(CCc2cccs2)CC(=O)N1CCc1cccs1)NCc1ccccc1] | N-benzyl-2-(3,6-dioxo- 1,4-bis(2-(thiophen-2- yl)ethyl)piperazin-2-yl) acetamide | B | 3.519 | 482 |
| Id.17.1 | 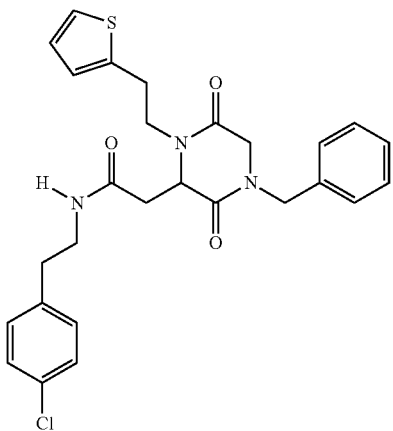 [SMILES: O=C(CC1C(=O)N(Cc2ccccc2)CC(=O)N1CCc1cccs1)NCCc1ccc(Cl)cc1] | 2-(4-benzyl-3,6-dioxo- 1-(2-(thiophen-2-yl) ethyl)piperazin-2-yl)- N-(4-chlorophenethyl) acetamide | C | 4.354 | 510 512 |

| | | | | | |
|---|---|---|---|---|---|
| Id.17.11 | 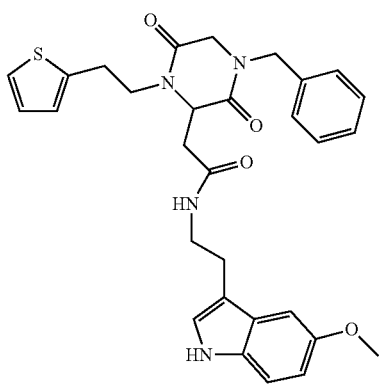 [SMILES: COc1ccc2[nH]cc(CCNC(=O)CC3C(=O)N(Cc4ccccc4)CC(=O)N3CCc3cccs3)c2c1] | 3-(2-(3-(2-aminoethyl)-5-methoxy-1H-indol-1-yl)-2-oxoethyl)-1-benzyl-4-(2-(thiophen-2-yl)ethyl)piperazin-2,5-dione | C | 3.984 | 545 |
| Id.17.12 | 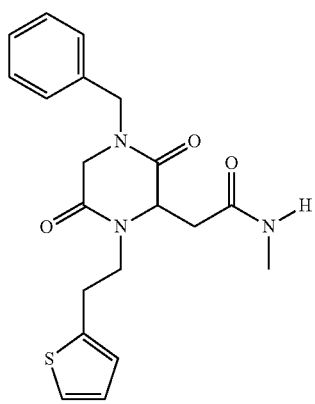 [SMILES: CNC(=O)CC1C(=O)N(Cc2ccccc2)CC(=O)N1CCc1cccs1] | 2-(4-benzyl-3,6-dioxo-1-(2-(thiophen-2-yl)ethyl)piperazin-2-yl)-N-methylacetamide | C | 3.355 | 386 |
| Id.17.13 | 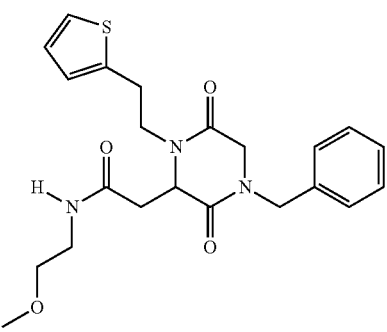 [SMILES: COCCNC(=O)CC1C(=O)N(Cc2ccccc2)CC(=O)N1CCc1cccs1] | 2-(4-benzyl-3,6-dioxo-1-(2-(thiophen-2-yl)ethyl)piperazin-2-yl)-N-(2-methoxyethyl)acetamide | C | 3.472 | 430 |
| Id.17.14 | 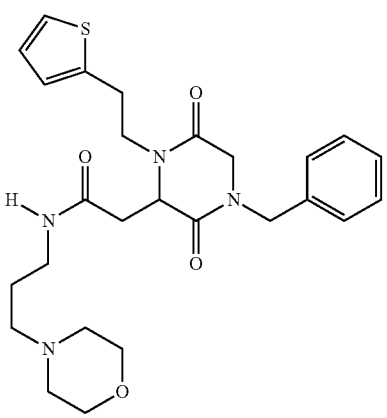 [SMILES: O=C(CC1C(=O)N(Cc2ccccc2)CC(=O)N1CCc1cccs1)NCCCN1CCOCC1] | 2-(4-benzyl-3,6-dioxo-1-(2-(thiophen-2-yl)ethyl)piperazin-2-yl)-N-(3-morpholinopropyl)acetamide | C | 2.984 | 499 |

-continued
| Id.17.15 | 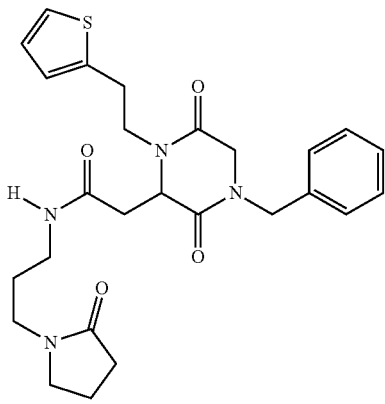 [SMILES: O=C(CC1C(=O)N(Cc2ccccc2)CC(=O)N1CCc1cccs1)NCCCN1CCCC1=O] | 2-(4-benzyl-3,6-dioxo-1-(2-(thiophen-2-yl)ethyl)piperazin-2-yl)-N-(3-(2-oxopyrrolidin-1-yl)propyl)acetamide | C | 3.407 | 497 |
| --- | --- | --- | --- | --- | --- |
| Id.17.19 | 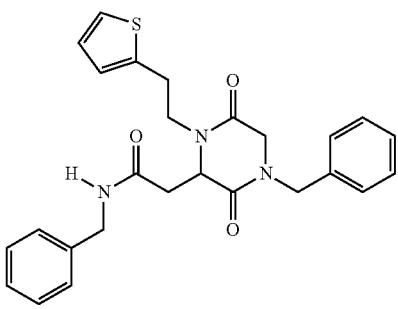 [SMILES: O=C(CC1C(=O)N(Cc2ccccc2)CC(=O)N1CCc1cccs1)NCc1ccccc1] | N-benzyl-2-(4-benzyl-3,6-dioxo-1-(2-(thiophen-2-yl)ethyl)piperazin-2-yl)acetamide | C | 4.021 | 462 |
| Id.17.2 | 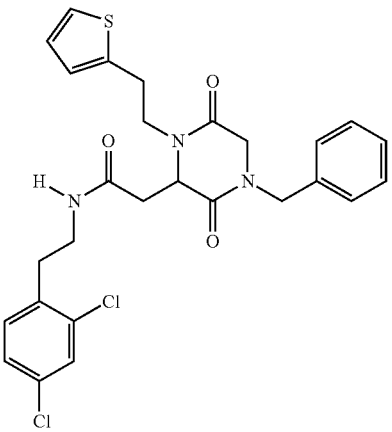 [SMILES: O=C(CC1C(=O)N(Cc2ccccc2)CC(=O)N1CCc1cccs1)NCCc1ccc(Cl)cc1Cl] | 2-(4-benzyl-3,6-dioxo-1-(2-(thiophen-2-yl)ethyl)piperazin-2-yl)-N-(2,4-dichlorophenethyl)acetamide | C | 4.596 | 544<br>546 |
| Id.17.23 | 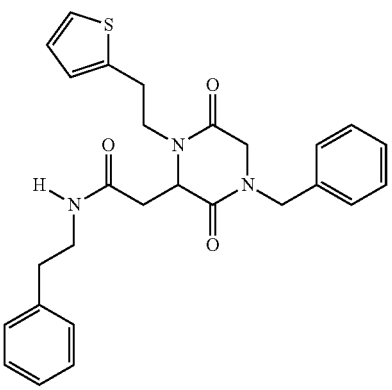 [SMILES: O=C(CC1C(=O)N(Cc2ccccc2)CC(=O)N1CCc1cccs1)NCCc1ccccc1] | 2-(4-benzyl-3,6-dioxo-1-(2-(thiophen-2-yl)ethyl)piperazin-2-yl)-N-phenethylacetamide | C | 4.131 | 476 |

-continued

| | | | | | |
|---|---|---|---|---|---|
| Id.17.24 | 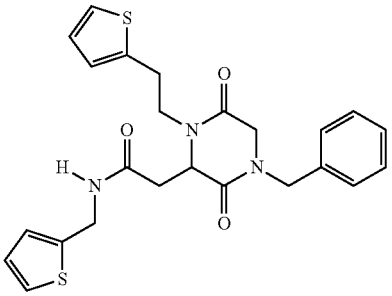 [SMILES: O=C(CC1C(=O)N(Cc2ccccc2)CC(=O)N1CCc1cccs1)NCc1cccs1] | 2-(4-benzyl-3,6-dioxo-1-(2-(thiophen-2-yl)ethyl)piperazin-2-yl)-N-(thiophen-2-ylmethyl)acetamide | C | 3.936 | 468 |
| Id.17.25 | 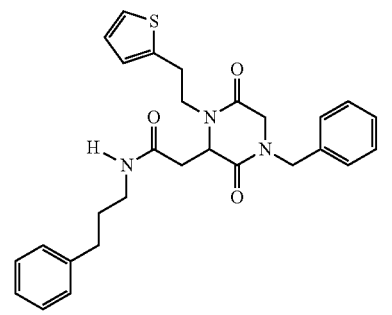 [SMILES: O=C(CC1C(=O)N(Cc2ccccc2)CC(=O)N1CCc1cccs1)NCCCc1ccccc1] | 2-(4-benzyl-3,6-dioxo-1-(2-(thiophen-2-yl)ethyl)piperazin-2-yl)-N-(3-phenylpropyl)acetamide | C | 4.294 | 490 |
| Id.17.26 | 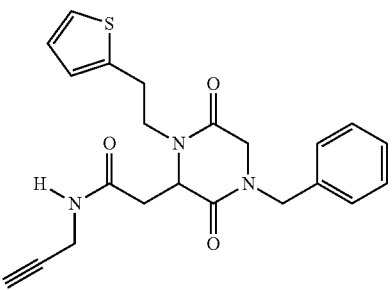 [SMILES: C#CCNC(=O)CC1C(=O)N(Cc2ccccc2)CC(=O)N1CCc1cccs1] | 2-(4-benzyl-3,6-dioxo-1-(2-(thiophen-2-yl)ethyl)piperazin-2-yl)-N-(prop-2-yn-1-yl)acetamide | C | 3.568 | 410 |
| Id.17.27 | 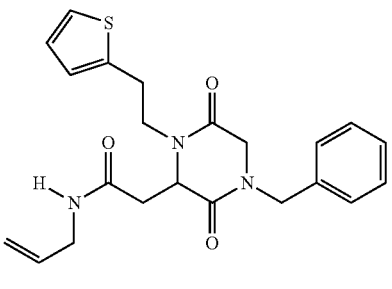 [SMILES: C=CCNC(=O)CC1C(=O)N(Cc2ccccc2)CC(=O)N1CCc1cccs1] | N-allyl-2-(4-benzyl-3,6-dioxo-1-(2-(thiophen-2-yl)ethyl)piperazin-2-yl)acetamide | C | 3.651 | 412 |
| Id.17.3 | 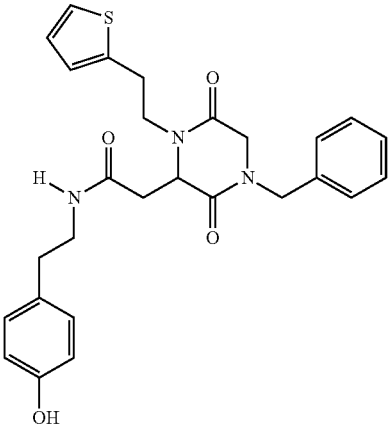 [SMILES: O=C(CC1C(=O)N(Cc2ccccc2)CC(=O)N1CCc1cccs1)NCCc1ccc(O)cc1] | 2-(4-benzyl-3,6-dioxo-1-(2-(thiophen-2-yl)ethyl)piperazin-2-yl)-N-(4-hydroxyphenethyl)acetamide | C | 3.656 | 492 |

-continued
| Id.17.4 | 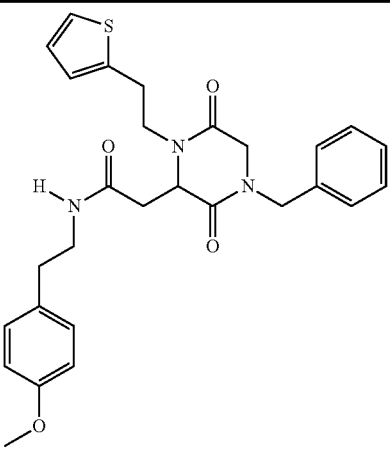 | 2-(4-benzyl-3,6-dioxo-1-(2-(thiophen-2-yl)ethyl)piperazin-2-yl)-N-(4-methoxyphenethyl)acetamide | C | 4.091 | 506 |
| Id.17.5 | 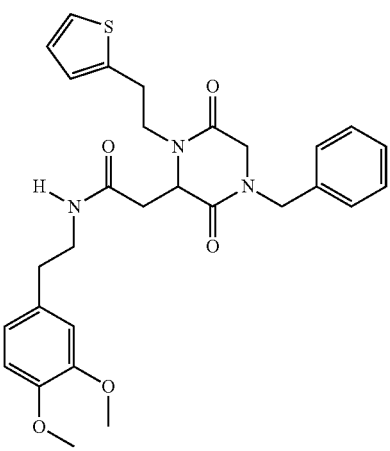 [SMILES: COc1ccc(CCNC(=O)CC2C(=O)N(Cc3ccccc3)CC(=O)N2CCc2cccs2)cc1OC] | 2-(4-benzyl-3,6-dioxo-1-(2-(thiophen-2-yl)ethyl)piperazin-2-yl)-N-(3,4-dimethoxyphenethyl)acetamide | C | 3.917 | 536 |
| Id.17.6 | 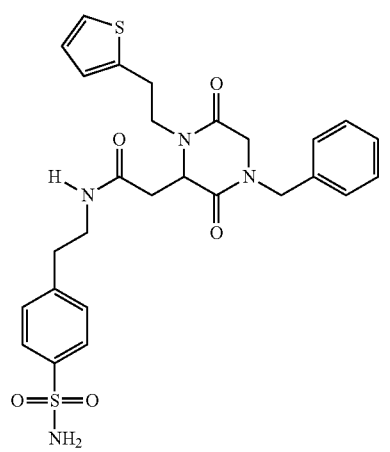 [SMILES: NS(=O)(=O)c1ccc(CCNC(=O)CC2C(=O)N(Cc3ccccc3)CC(=O)N2CCc2cccs2)cc1] | 2-(4-benzyl-3,6-dioxo-1-(2-(thiophen-2-yl)ethyl)piperazin-2-yl)-N-(4-sulfamoylphenethyl)acetamide | C | 3.548 | 555 |

| | | | | | |
|---|---|---|---|---|---|
| Id.17.7 | 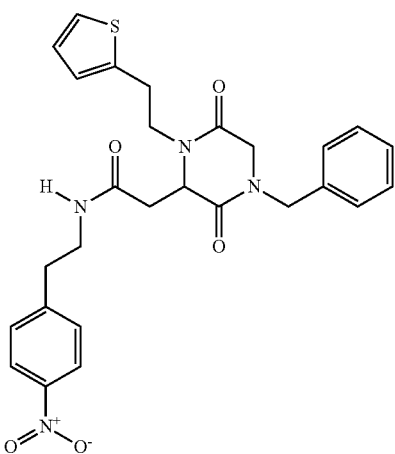 [SMILES: O=C(CC1C(=O)N(Cc2ccccc2)CC(=O)N1CCc1cccs1)NCCc1ccc([N+](=O)[O-])cc1] | 2-(4-benzyl-3,6-dioxo-1-(2-(thiophen-2-yl)ethyl)piperazin-2-yl)-N-(4-nitrophenethyl)acetamide | C | 4.086 | 521 |
| Id.17.8 | 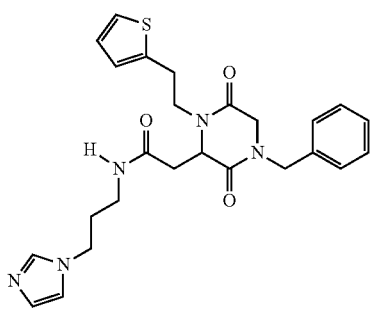 [SMILES: O=C(CC1C(=O)N(Cc2ccccc2)CC(=O)N1CCc1cccs1)NCCCn1ccnc1] | N-(3-(1H-imidazol-1-yl)propyl)-2-(4-benzyl-3,6-dioxo-1-(2-(thiophen-2-yl)ethyl)piperazin-2-yl)acetamide | C | 3.000 | 480 |
| Id.17.9 | 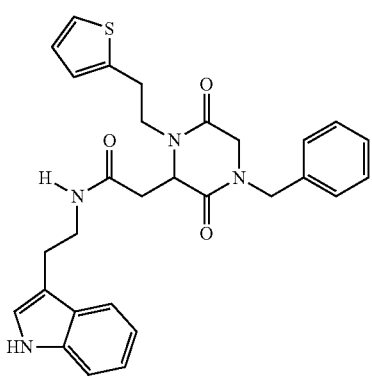 [SMILES: O=C(CC1C(=O)N(Cc2ccccc2)CC(=O)N1CCc1cccs1)NCCc1c[nH]c2ccccc12] | N-(2-(1H-indol-3-yl)ethyl)-2-(4-benzyl-3,6-dioxo-1-(2-(thiophen-2-yl)ethyl)piperazin-2-yl)acetamide | C | 4.059 | 515 |
| Id.19.1 | 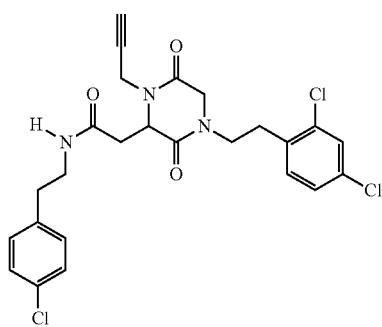 [SMILES: C#CCN1C(=O)CN(CCc2ccc(Cl)cc2Cl)C(=O)C1CC(=O)NCCc1ccc(Cl)cc1] | N-(4-chlorophenethyl)-2-(4-(2,4-dichlorophenethyl)-3,6-dioxo-1-(prop-2-yn-1-yl)piperazin-2-yl)acetamide | C | 4.548 | 520 522 |

| | | | | | |
|---|---|---|---|---|---|
| Id.19.11 | | 2-(4-(2,4-dichlorophen-ethyl)-3,6-dioxo-1-(prop-2-yn-1-yl)piperazin-2-yl)-N-(2-(5-methoxy-1H-indol-3-yl)ethyl)acetamide | C | 4.166 | 555 557 |
| Id.19.12 | | 2-(4-(2,4-dichlorophen-ethyl)-3,6-dioxo-1-(prop-2-yn-1-yl)piperazin-2-yl)-N-methylacetamide | C | 3.552 | 396 398 |
| Id.19.13 | | 2-(4-(2,4-dichlorophen-ethyl)-3,6-dioxo-1-(prop-2-yn-1-yl)piperazin-2-yl)-N-(2-methoxyethyl)acetamide | C | 3.670 | 440 442 |
| Id.19.14 | | 2-(4-(2,4-dichlorophen-ethyl)-3,6-dioxo-1-(prop-2-yn-1-yl)piperazin-2-yl)-N-(3-morpholinopropyl)acetamide | C | 3.081 | 509 511 |
| Id.19.15 | | 2-(4-(2,4-dichlorophen-ethyl)-3,6-dioxo-1-(prop-2-yn-1-yl)piperazin-2-yl)-N-(3-(2-oxopyrrolidin-1-yl)propyl)acetamide | C | 3.579 | 507 509 |

-continued

| | | | | | |
|---|---|---|---|---|---|
| Id.19.19 | (structure) | N-benzyl-2-(4-(2,4-dichlorophenethyl)-3,6-dioxo-1-(prop-2-yn-1-yl)piperazin-2-yl)acetamide | C | 4.214 | 472<br>474 |
| Id.19.2 | (structure) | N-(2,4-dichlorophen-ethyl)-2-(4-(2,4-dichlorophenethyl)-3,6-dioxo-1-(prop-2-yn-1-yl)piperazin-2-yl)acetamide | C | 4.798 | 554<br>556<br>558 |
| Id.19.23 | (structure) | 2-(4-(2,4-dichlorophen-ethyl)-3,6-dioxo-1-(prop-2-yn-1-yl)piperazin-2-yl)-N-phenethylacetamide | C | 4.329 | 486<br>488 |
| Id.19.24 | (structure) | 2-(4-(2,4-dichlorophen-ethyl)-3,6-dioxo-1-(prop-2-yn-1-yl)piperazin-2-yl)-N-(thiophen-2-ylmethyl)acetamide | C | 4.147 | 478<br>480 |
| Id.19.25 | (structure) | 2-(4-(2,4-dichlorophen-ethyl)-3,6-dioxo-1-(prop-2-yn-1-yl)piperazin-2-yl)-N-(3-phenylpropyl)acetamide | C | 4.493 | 500<br>502 |
| Id.19.26 | (structure) | 2-(4-(2,4-dichlorophen-ethyl)-3,6-dioxo-1-(prop-2-yn-1-yl)piperazin-2-yl)-N-(prop-2-yn-1-yl)acetamide | C | 3.779 | 420<br>422 |

| | | | | | |
|---|---|---|---|---|---|
| Id.19.27 | 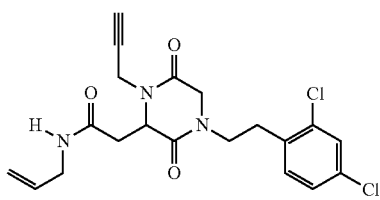 [SMILES: C#CCN1C(=O)CN(CCc2ccc(Cl)cc2Cl)C(=O)C1CC(=O)NCC=C] | N-allyl-2-(4-(2,4-dichlorophenethyl)-3,6-dioxo-1-(prop-2-yn-1-yl)piperazin-2-yl)acetamide | C | 3.864 | 422 424 |
| Id.19.3 | 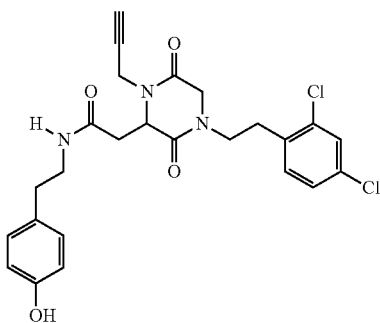 [SMILES: C#CCN1C(=O)CN(CCc2ccc(Cl)cc2Cl)C(=O)C1CC(=O)NCCc1ccc(O)cc1] | 2-(4-(2,4-dichlorophen-ethyl)-3,6-dioxo-1-(prop-2-yn-1-yl)piperazin-2-yl)-N-(4-hydroxyphenethyl)acetamide | C | 3.840 | 502 504 |
| Id.19.4 | 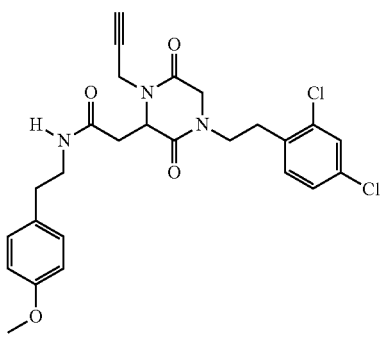 [SMILES: C#CCN1C(=O)CN(CCc2ccc(Cl)cc2Cl)C(=O)C1CC(=O)NCCc1ccc(OC)cc1] | 2-(4-(2,4-dichlorophen-ethyl)-3,6-dioxo-1-(prop-2-yn-1-yl)piperazin-2-yl)-N-(4-methoxyphenethyl)acetamide | C | 4.289 | 516 518 |
| Id.19.5 | 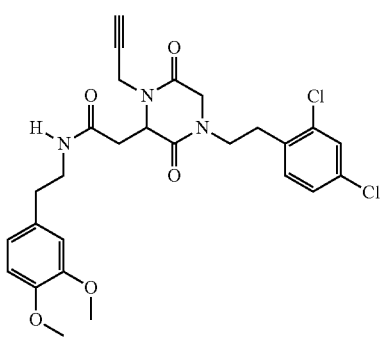 [SMILES: C#CCN1C(=O)CN(CCc2ccc(Cl)cc2Cl)C(=O)C1CC(=O)NCCc1ccc(OC)c(OC)c1] | 2-(4-(2,4-dichlorophen-ethyl)-3,6-dioxo-1-(prop-2-yn-1-yl)piperazin-2-yl)-N-(3,4-dimethoxyphenethyl)acetamide | C | 4.109 | 546 548 |
| Id.19.6 | 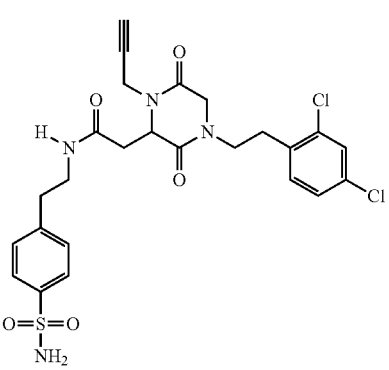 [SMILES: C#CCN1C(=O)CN(CCc2ccc(Cl)cc2Cl)C(=O)C1CC(=O)NCCc1ccc(S(N)(=O)=O)cc1] | 2-(4-(2,4-dichlorophen-ethyl)-3,6-dioxo-1-(prop-2-yn-1-yl)piperazin-2-yl)-N-(4-sulfamoylphenethyl)acetamide | C | 3.717 | 565 567 |

-continued

| | | | | | |
|---|---|---|---|---|---|
| Id.19.7 | 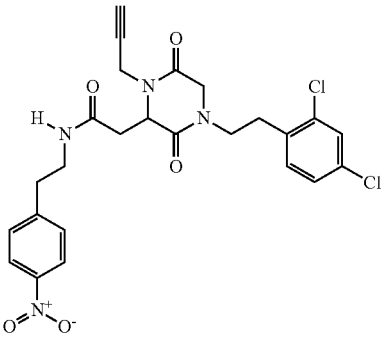 [SMILES: C#CCN1C(=O)CN(CCc2ccc(Cl)cc2Cl)C(=O)C1CC(=O)NCCc1ccc([N+](=O)[O-])cc1] | 2-(4-(2,4-dichlorophen-ethyl)-3,6-dioxo-1-(prop-2-yn-1-yl)piperazin-2-yl)-N-(4-nitrophenethyl)acetamide | C | 4.275 | 531 533 |
| Id.19.8 | 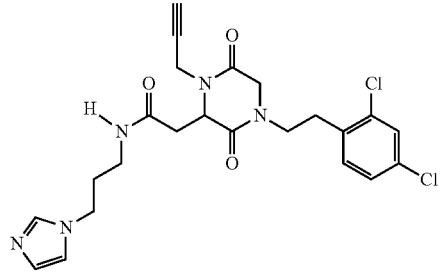 [SMILES: C#CCN1C(=O)CN(CCc2ccc(Cl)cc2Cl)C(=O)C1CC(=O)NCCCn1ccnc1] | N-(3-(1H-imidazol-1-yl)propyl)-2-(4-(2,4-dichlorophenethyl)-3,6-dioxo-1-(prop-2-yn-1-yl)piperazin-2-yl)acetamide | C | 3.099 | 490 492 |
| Id.19.9 | 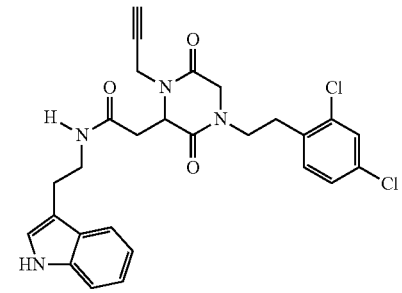 [SMILES: C#CCN1C(=O)CN(CCc2ccc(Cl)cc2Cl)C(=O)C1CC(=O)NCCc1c[nH]c2ccccc12] | N-(2-(1H-indol-3-yl)ethyl)-2-(4-(2,4-dichlorophenethyl)-3,6-dioxo-1-(prop-2-yn-1-yl)piperazin-2-yl)acetamide | C | 4.245 | 525 527 |
| Id.22.1 | 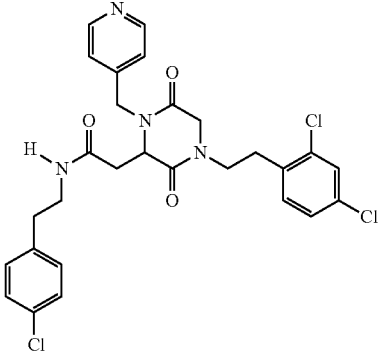 [SMILES: O=C(CC1C(=O)N(CCc2ccc(Cl)cc2Cl)CC(=O)N1Cc1ccncc1)NCCc1ccc(Cl)cc1] | N-(4-chlorophenethyl)-2-(4-(2,4-dichlorophen-ethyl)-3,6-dioxo-1-(pyridin-4-ylmethyl)piperazin-2-yl)acetamide | C | 3.822 | 573 575 |
| Id.22.11 | 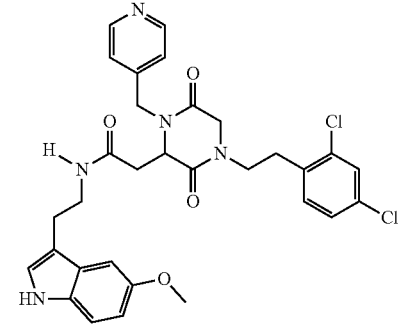 [SMILES: COc1ccc2[nH]cc(CCNC(=O)CC3C(=O)N(CCc4ccc(Cl)cc4Cl)CC(=O)N3Cc3ccncc3)c2c1] | 2-(4-(2,4-dichlorophen-ethyl)-3,6-dioxo-1-(pyridin-4-ylmethyl)piperazin-2-yl)-N-(2-(5-methoxy-1H-indol-3-yl)ethyl)acetamide | C | 3.511 | 608 610 |

-continued

| | | | | | |
|---|---|---|---|---|---|
| Id.22.12 | 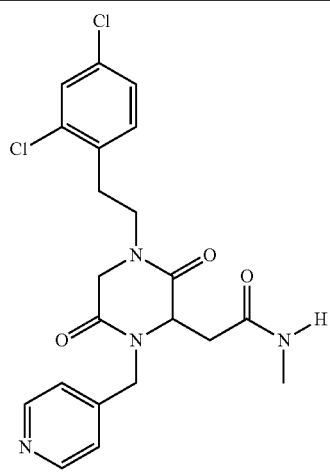 | 2-(4-(2,4-dichlorophen-ethyl)-3,6-dioxo-1-(pyridin-4-ylmethyl)piperazin-2-yl)-N-methylacetamide | C | 3.015 | 449<br>451 |
| Id.22.13 | 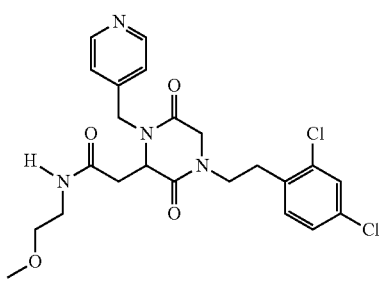 [SMILES: COCCNC(=O)CC1C(=O)N(CCc2ccc(Cl)cc2Cl)CC(=O)N1Cc1ccncc1] | 2-(4-(2,4-dichlorophen-ethyl)-3,6-dioxo-1-(pyridin-4-ylmethyl)piperazin-2-yl)-N-(2-methoxyethyl)acetamide | C | 3.103 | 493<br>495 |
| Id.22.14 | 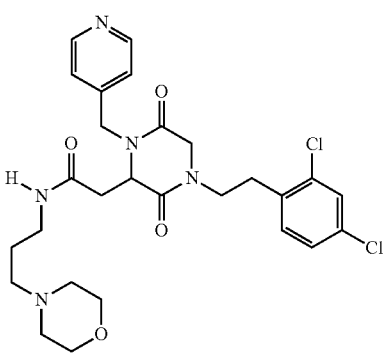 [SMILES: O=C(CC1C(=O)N(CCc2ccc(Cl)cc2Cl)CC(=O)N1Cc1ccncc1)NCCCN1CCOCC1] | 2-(4-(2,4-dichlorophen-ethyl)-3,6-dioxo-1-(pyridin-4-ylmethyl)piperazin-2-yl)-N-(3-morpholinopropyl)acetamide | C | 2.680 | 562<br>564 |
| Id.22.15 | 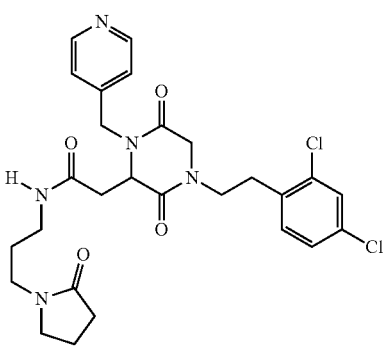 [SMILES: O=C(CC1C(=O)N(CCc2ccc(Cl)cc2Cl)CC(=O)N1Cc1ccncc1)NCCCN1CCCC1=O] | 2-(4-(2,4-dichlorophen-ethyl)-3,6-dioxo-1-(pyridin-4-ylmethyl)piperazin-2-yl)-N-(3-(2-oxopyrrolidin-1-yl)propyl)acetamide | C | 3.098 | 560<br>562 |

-continued

| Id. | Structure | Name | | | |
|---|---|---|---|---|---|
| Id.22.19 | 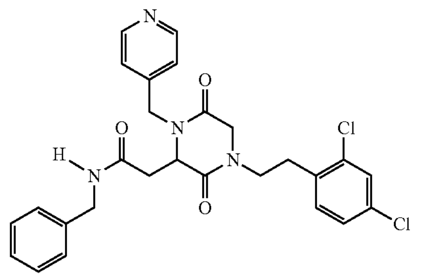 [SMILES: O=C(CC1C(=O)N(CCc2ccc(Cl)cc2Cl)CC(=O)N1Cc1ccncc1)NCc1ccccc1] | N-benzyl-2-(4-(2,4-dichlorophenethyl)-3,6-dioxo-1-(pyridin-4-ylmethyl)piperazin-2-yl)acetamide | C | 3.524 | 525 527 |
| Id.22.2 | 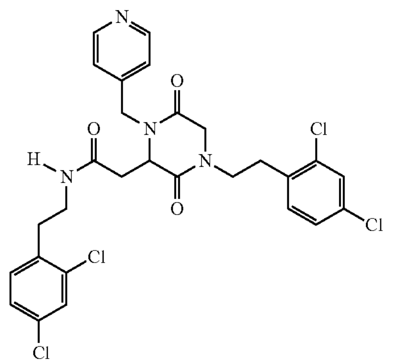 [SMILES: O=C(CC1C(=O)N(CCc2ccc(Cl)cc2Cl)CC(=O)N1Cc1ccncc1)NCCc1ccc(Cl)cc1Cl] | N-(2,4-dichlorophenethyl)-2-(4-(2,4-dichlorophenethyl)-3,6-dioxo-1-(pyridin-4-ylmethyl)piperazin-2-yl)acetamide | C | 4.012 | 607 609 |
| Id.22.23 | 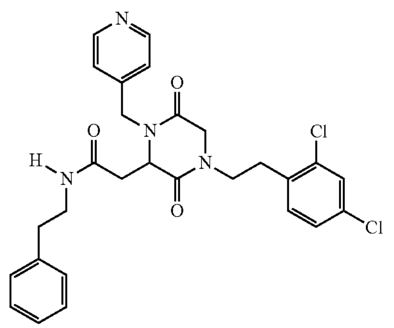 [SMILES: O=C(CC1C(=O)N(CCc2ccc(Cl)cc2Cl)CC(=O)N1Cc1ccncc1)NCCc1ccccc1] | 2-(4-(2,4-dichlorophenethyl)-3,6-dioxo-1-(pyridin-4-ylmethyl)piperazin-2-yl)-N-phenethylacetamide | C | 3.545 | 539 542 |
| Id.22.24 | 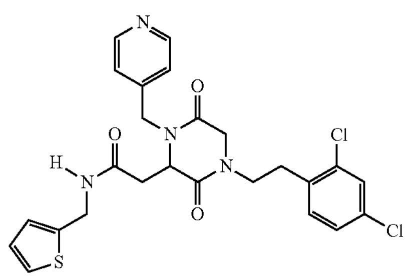 [SMILES: O=C(CC1C(=O)N(CCc2ccc(Cl)cc2Cl)CC(=O)N1Cc1ccncc1)NCc1cccs1] | 2-(4-(2,4-dichlorophenethyl)-3,6-dioxo-1-(pyridin-4-ylmethyl)piperazin-2-yl)-N-(thiophen-2-ylmethyl)acetamide | C | 3.441 | 531 533 |
| Id.22.25 | 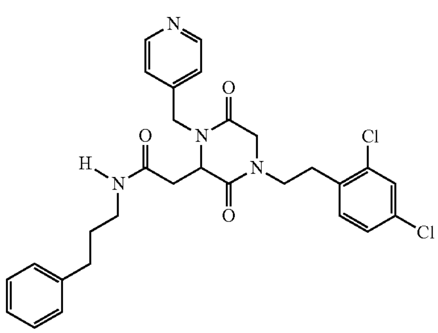 [SMILES: O=C(CC1C(=O)N(CCc2ccc(Cl)cc2Cl)CC(=O)N1Cc1ccncc1)NCCCc1ccccc1] | 2-(4-(2,4-dichlorophenethyl)-3,6-dioxo-1-(pyridin-4-ylmethyl)piperazin-2-yl)-N-(3-phenylpropyl)acetamide | C | 3.732 | 553 555 |

| | | | | | |
|---|---|---|---|---|---|
| Id.22.26 | 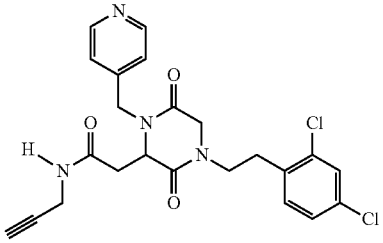 [SMILES: C#CCNC(=O)CC1C(=O)N(CCc2ccc(Cl)cc2Cl)CC(=O)N1Cc1ccncc1] | 2-(4-(2,4-dichlorophen-ethyl)-3,6-dioxo-1-(pyridin-4-ylmethyl)piperazin-2-yl)-N-(prop-2-yn-1-yl)acetamide | C | 3.143 | 473 475 |
| Id.22.27 | 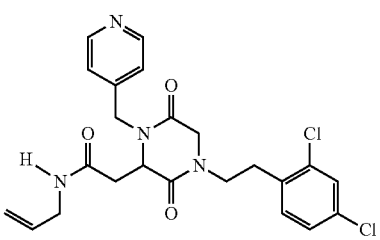 [SMILES: C=CCNC(=O)CC1C(=O)N(CCc2ccc(Cl)cc2Cl)CC(=O)N1Cc1ccncc1] | N-allyl-2-(4-(2,4-dichloro-phenethyl)-3,6-dioxo-1-(pyridin-4-ylmethyl)piperazin-2-yl)acetamide | C | 3.227 | 475 477 |
| Id.22.3 | 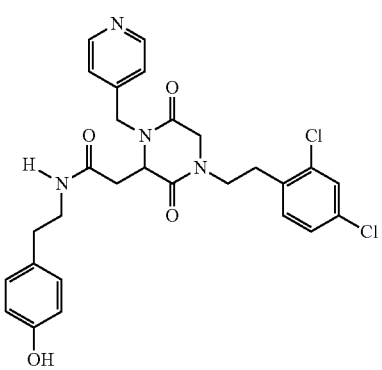 [SMILES: O=C(CC1C(=O)N(CCc2ccc(Cl)cc2Cl)CC(=O)N1Cc1ccncc1)NCCc1ccc(O)cc1] | 2-(4-(2,4-dichlorophen-ethyl)-3,6-dioxo-1-(pyridin-4-ylmethyl)piperazin-2-yl)-N-(4-hydroxyphenethyl)acetamide | C | 3.273 | 555 557 |
| Id.22.4 | 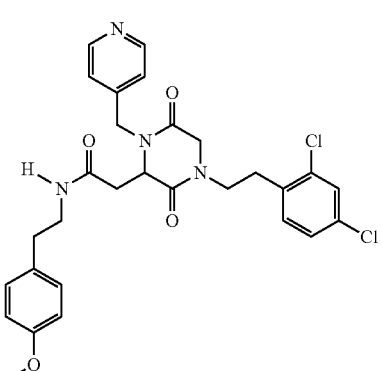 | 2-(4-(2,4-dichlorophen-ethyl)-3,6-dioxo-1-(pyridin-4-ylmethyl)piperazin-2-yl)-N-(4-methoxyphenethyl)acetamide | C | 3.603 | 569 571 |
| Id.22.5 | 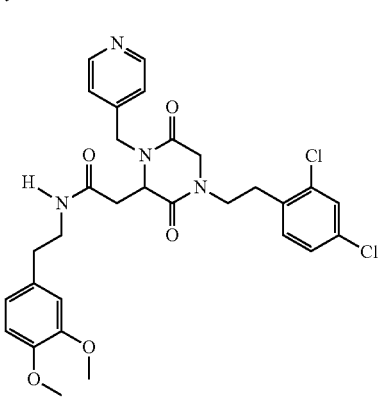 | 2-(4-(2,4-dichlorophen-ethyl)-3,6-dioxo-1-(pyridin-4-ylmethyl)piperazin-2-yl)-N-(3,4-dimethoxyphenethyl)acetamide | C | 3.466 | 599 601 |

-continued

| | | | | | |
|---|---|---|---|---|---|
| Id.22.6 | 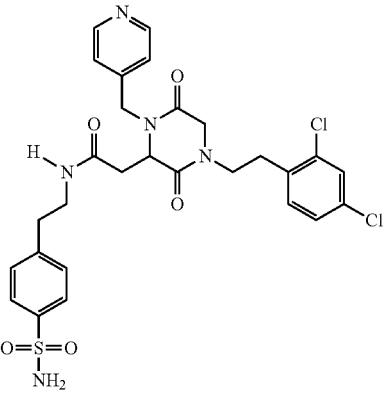 [SMILES: NS(=O)(=O)c1ccc(CCNC(=O)CC2C(=O)N(CCc3ccc(Cl)cc3Cl)CC(=O)N2Cc2ccncc2)cc1] | 2-(4-(2,4-dichlorophen-ethyl)-3,6-dioxo-1-(pyridin-4-ylmethyl)piperazin-2-yl)-N-(4-sulfamoylphenethyl)acetamide | C | 3.173 | 618 620 |
| Id.22.7 | 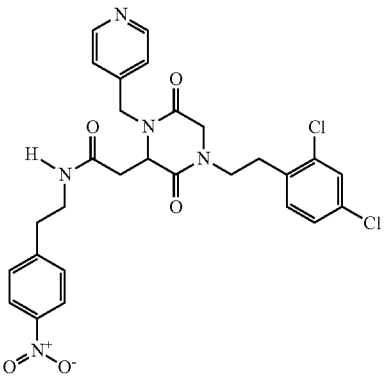 [SMILES: O=C(CC1C(=O)N(CCc2ccc(Cl)cc2Cl)CC(=O)N1Cc1ccncc1)NCCc1ccc([N+](=O)[O-])cc1] | 2-(4-(2,4-dichlorophen-ethyl)-3,6-dioxo-1-(pyridin-4-ylmethyl)piperazin-2-yl)-N-(4-nitrophenethyl)acetamide | C | 3.607 | 584 586 |
| Id.22.8 | 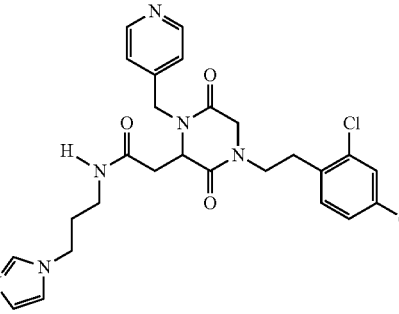 | N-(3-(1H-imidazol-1-yl)propyl)-2-(4-(2,4-dichlorophenethyl)-3,6-dioxo-1-(pyridin-4-ylmethyl)piperazin-2-yl)acetamide | C | 2.668 | 543 545 |
| Id.22.9 | 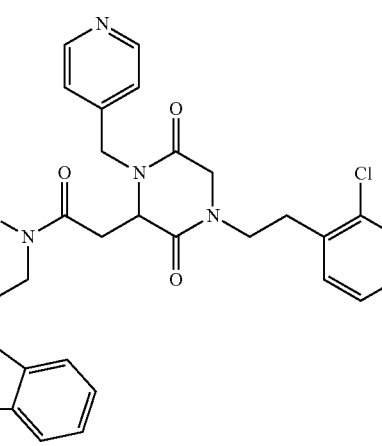 | N-(2-(1H-indol-3-yl)ethyl)-2-(4-(2,4-dichloro-phenethyl)-3,6-dioxo-1-(pyridin-4-ylmethyl)piperazin-2-yl)acetamide | C | 3.569 | 578 580 |

181

Compounds of formula Ie

Ie.1 6-amino-2-(2-(4-(2,4-dichlorophenethyl)-1-(3,3-diphenylpropyl)-3,6-dioxopiperazin-2-yl)acetamido)hexanamide

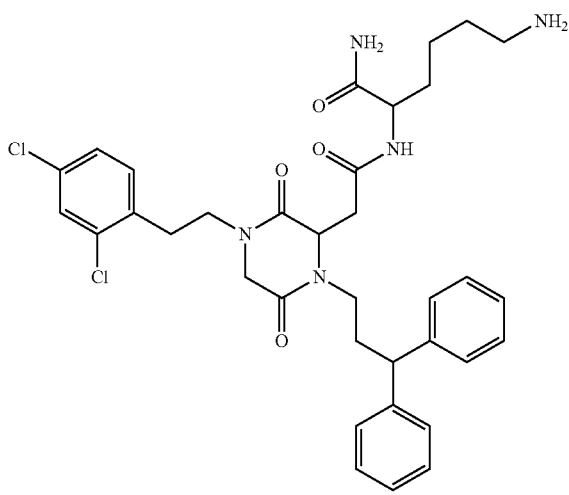 [SMILES: NCCCCC(NC(=O)CC1C(=O)N(CCc2ccc(Cl)cc2Cl)CC(=O)N1CCC(c1ccccc1)c1ccccc1)C(N)=O]

182

Compounds of formula If

If.1.2 6-amino-2-(2-(N-(2,4-dichlorophenethyl)-2-(4-(2,4-dichlorophenethyl)-1-(3,3-diphenylpropyl)-3,6-dioxopiperazin-2-yl)acetamido)acetamido)hexanamide

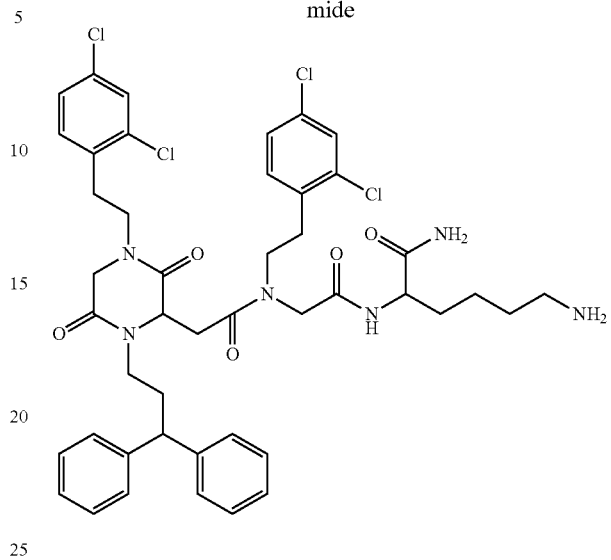

Rink amide-Fmoc resin (II, 500 mg, 0.305 mmol) was deprotected with 5 ml of 20% piperidine in DMF stirring in a microwave reactor for 2 min at 60° C. The resin was filtered and washed with DMF (3×15 ml), isopropyl alcohol (3×15 ml) and DCM (3×15 ml). The Fmoc-L-Lys(Boc)-OH amino acid (XI, 286 mg, 2 eq.) was then bound to the resin using HOBT (82 mg, 2 eq.) and DIC (96 µL, 2 eq.) in 5 ml of DMF. The mixture was stirred at room temperature for 1 h. The resin was filtered and washed with DMF (3×15 ml), isopropyl alcohol (3×15 ml) and DCM (3×15 ml). Once the Fmoc group was removed with 5 ml of 20% piperidine in DMF for 20 min, the resin was filtered and washed with DMF (3×15 ml), isopropyl alcohol (3×15 ml) and DCM (3×15 ml). Subsequently the resin was treated with a solution of acid X (181 mg, 1.1 eq.), HATU (348 mg, 3 eq.), HOBT (123 mg, 3 eq.) and DIPEA (0.313 ml, 6 eq.) in 5 ml of DMF. The reaction mixture was stirred at room temperature for 16 h. The resin was dried and washed with DMF (3×3 ml), isopropyl alcohol (3×3 ml) and DCM (3×3 ml) and was subsequently treated with a mixture of 80:20:2.5:2.5 TFA/DCM/water/triisopropylsilane (5 ml) for 30 min at room temperature. The resin was filtered and the filtrate was evaporated at reduced pressure. The residue obtained is purified by normal phase chromatography using a gradient of a dichloromethane-methanol-ammonia mixture to obtain 15 mg of the desired compound (Ie.1, 8% yield, 100% purity). MS (M+H)$^+$ calculated for $C_{35}H_{41}Cl_2N_5O_4$, 666.26, experimental, 666.40.

Rink amide-Fmoc resin (II, 800 mg, 0.42 mmol) was deprotected with 8 ml of 20% piperidine in DMF stirring in a microwave reactor for 2 min at 60° C. The resin was filtered and washed with DMF (3×15 ml), isopropyl alcohol (3×15 ml) and DCM (3×15 ml). The Fmoc-L-Lys(Boc)-OH amino acid (XII, 497 mg, 2 eq.) was the bound to the resin using HOBT (143 mg, 2 eq.) and DIC (165 µL, 2 eq.) in 8 ml of DMF. The mixture was stirred at room temperature for 1 h. The resin was filtered and washed with DMF (3×15 ml), isopropyl alcohol (3×15 ml) and DCM (3×15 ml). Once the Fmoc group was removed with 8 ml of 20% piperidine in DMF for 20 min, the resin was filtered and washed with DMF (3×15 ml), isopropyl alcohol (3×15 ml) and DCM (3×15 ml). The resin was treated with a solution of bromoacetic acid (III, 295 mg, 4 eq.) and DIC (0.33 ml, 4 eq.) in 1:2 DMF:DCM (8 ml) and the mixture was stirred for 20 min at room temperature. The resin was filtered and washed with DMF (3×15 ml), isopropyl alcohol (3×15 ml) and DCM (3×15 ml). A solution of 2,4-dichlorophenethylamine (IVd, 0.32 ml, 4 eq.) and triethylamine (0.295 ml, 4 eq.) in 12 ml of DMF was added to the resin and the suspension was stirred for 3 h at room temperature. The supernatant was removed and the reaction was repeated in the same conditions. The resin was filtered and washed with DMF (3×15 ml), isopropyl alcohol (3×15 ml) and DCM (3×15 ml) to obtain the resin XIV, which was treated with a solution of acid X (274 mg, 2 eq.), HATU (116 mg, 1.6 eq.), HOBT and DIPEA (0.295 ml, 3.2 eq.) in 8 ml of DMF. The reaction mixture was stirred at room temperature for 3 h. The resin was dried and washed with DMF (3×3 ml), isopropyl alcohol (3×3 ml) and DCM (3×3 ml) and was subsequently treated with a mixture of 80:20:2.5:2.5 TFA/DCM/water/triisopropylsilane (5 ml) for 30 min at room temperature. The resin was filtered and the filtrate was evaporated at reduced pressure. The residue obtained was purified by semi-preparative RP-HPLC using a gradient of an acetonitrile-water mixture to obtain 128 mg of the desired compound (If.1.2, 34% yield, 99% purity). HRMS (M+H)+ calculated for $C_{45}H_{50}Cl_4N_6O_5$, 895.2675; experimental, 895.2648.

Pharmacological Examples

In Vitro Apoptosome Formation Inhibition Assay

Recombinant Apaf-1 produced in insect cells (rApaf-1) was incubated in the presence (at a concentration of 10 µM) or absence (as control) of the compounds to be evaluated in the assay buffer (20 mM Hepes-KOH pH 7.5, 10 mM KCl, 1.5 mM $MgCl_2$, 1 mM EDTA, 1 mM EGTA, 1 mM DTT, 0.1 mM PMSF) for 15 minutes at 30° C. The final rApaf-1 concentration was 40 nM. dATP/Mg (Sigma) and purified horse cytochrome c (Sigma) were then added achieving final concentrations of 100 µM and 0.1 µM, respectively. It was incubated for 60 minutes at 30° C. and recombinant procaspase-9 produced in E. coli (rprocaspase-9, final concentration 0.1 µM) was then added and it was incubated for 10 minutes at 30° C. before adding the caspase-9 fluorogenic substrate Ac-LEDH-afc (final concentration 50 µM). The total assay volume was 200 µL. The caspase activity was continuously monitored by means of the afc release at 37° C. in a Wallac 1420 Workstation ($\lambda_{exc}$=390 nm, $\lambda_{em}$=510 nm).

The activity values of some compounds described in the examples are indicated in the following table expressed as the percentage of Apaf-1 inhibition.

| Example | % Apaf-1 inhibition |
| --- | --- |
| I.1.20 | 36 |
| I.1.16 | 46 |
| I.1.25 | 26 |
| Ia.6.2 | 29 |
| Ib.1.2 | 72 |
| Ib.2.2 | 28 |
| Ib.3.2 | 48 |
| Ic.3.2 | 29 |
| Ic.5.2 | 23 |
| Id.5.2 | 40 |
| If.1.2 | 80 |

The invention claimed is:
1. A compound of formula (I)

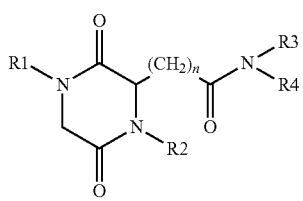

(I)

or pharmaceutically acceptable salts thereof, wherein:
R1 is —$(CH_2)_{0-3}$-aryl,
R2 is selected from —$C_{1-5}$ alkyl, —$C_{2-5}$ alkenyl, —$(CH_2)_{0-3}$-cycloalkyl, —$(CH_2)_{1-3}$-heterocycle, —$(CH_2)_{0-3}$-aryl, —$(CH_2)_{0-3}$-heteroaryl, —$(CH_2)_{1-2}$—$CH(aryl)_2$, —$(CH_2)_{1-2}$—CH(aryl)(heteroaryl) and —$(CH_2)_{1-2}$—$CH(heteroaryl)_2$,
R3 is selected from —H, —$C_{1-5}$ alkyl, —$C_{2-5}$ alkenyl, —$(CH_2)_{0-3}$-cycloalkyl, —$(CH_2)_{1-3}$-heterocycle, —$(CH_2)_{1-3}$-aryl, —$(CH_2)_{1-3}$-heteroaryl, —$(CH_2)_{1-3}$—CONR5R6, —$(CH_2)_{1-2}$—$CH(aryl)_2$, —$(CH_2)_{1-2}$—CH(aryl)(heteroaryl) and —$(CH_2)_{1-2}$—$CH(heteroaryl)_2$,
R4 is selected from —H, —$C_{1-5}$ alkyl, —$(CHR7)_{1-3}$—CO—NR5R6, —$(CHR7)_{1-3}$—CO—OR5, —$(CH_2)_{1-3}$—NR5R6, —$(CH_2)_{1-3}$—CO[NCHR7CO]$_m$NH$_2$ and —$(CH_2)_{1-3}$—CO[NCHR7CO]$_m$OR5, n is an integer selected from 1 and 2;

m is an integer selected from 1, 2 and 3;

R5 and R6 are independently selected from —H, —$C_{1-5}$ alkyl and —$(CH_2)_{0-3}$-aryl, R7 is selected from —H, —$C_{1-5}$ alkyl, —$(CH_2)_{1-3}$-aryl and —$(CH_2)_{1-3}$-heteroaryl, such that when m is greater than 1 the R7 substituents can be equal to or different from one another, wherein the $C_{1-5}$ alkyl, $C_{2-5}$ alkenyl, cycloalkyl and heterocycle groups can be optionally substituted with one or several substituents selected independently from halogen, OH, OR5, $OCF_3$, SH, SR5, $NH_2$, NR5R6, NHCOR5; COOH, COOR5, OCOR5, aryl and heteroaryl, wherein the aryl and heteroaryl groups can be optionally substituted with one or several substituents selected independently from halogen, CF3, OH, ORS, $OCF_3$, SH, SR5, $NH_2$, NHCOR5; $NO_2$, CN, COR5, COOR5, OCOR5, CONR5R6, —$(CH_2)_{0-3}$NR5R6, $SO_2NH_2$, $NHSO_2CH3$, $C_{1-5}$ alkyl, aryl and heteroaryl, wherein the heterocycle and heteroaryl groups can be optionally substituted on a secondary nitrogen atom with $C_{1-5}$ alkyl, cycloalkyl or —$(CH_2)_{0-3}$-aryl, on the condition that when R2 is 2-(4-fluorophenyl)ethyl, R4 is —$CH_2$—CO—$NH_2$ and n is 1, then:
 if R1 is 2-(4-fluorophenyl)ethyl, R3 is not 2-(4-methoxyphenyl)ethyl, 2-(2-pyridyl)ethyl or 2-(2,4-dichlorophenyl)ethyl, and
 if R1 is 2-(2,4-dichlorophenyl)ethyl, R3 is not 2-(4-methoxyphenyl)ethyl or 2-(2-pyridyl)ethyl.

2. The compound according to claim 1, wherein R2 is —$C_{1-5}$ alkyl, —$(CH_2)_{0-3}$-aryl, —$(CH_2)_{0-3}$-heteroaryl or —$(CH_2)_{1-2}$—$CH(aryl)_2$.

3. The compound according to claim 1, wherein R3 is —H, —$C_{1-5}$ alkyl, —$(CH_2)_{1-3}$-heterocycle, —$(CH_2)_{1-3}$-aryl or —$(CH_2)_{1-3}$-heteroaryl.

4. The compound according to claim 1, wherein R4 is —H, —$(CHR7)_{1-3}$—CO—NR5R6, —$(CHR7)_{1-3}$—CO—OR5 or —$(CH_2)_{1-3}$—CO[NCHR7CO]$_m$NH$_2$.

5. The compound according to claim 1, wherein n is 1.

6. The compound according to claim 1, wherein m is 1.

7. The compound according to claim 1, wherein R5 is —H or —$C_{1-5}$ alkyl.

8. The compound according to claim 1, wherein R6 is —H.

9. The compound according to claim 1, wherein R7 is —H, —$C_{1-5}$ alkyl, —$(CH_2)_{1-3}$-aryl or —$(CH_2)_{1-3}$-heteroaryl.

10. The compound according to claim 1, wherein R2 is —$C_{1-5}$ alkyl, —$(CH_2)_{0-3}$-aryl, —$(CH_2)_{0-3}$-heteroaryl or —$(CH_2)_{1-2}$—$CH(aryl)_2$; R3 is —H, —$C_{1-5}$ alkyl, —$(CH_2)_{1-3}$-heterocycle, —$(CH_2)_{1-3}$-aryl or —$(CH_2)_{1-3}$-heteroaryl; R4 is —H, —$(CHR7)_{1-3}$—CO—NR5R6, —$(CHR7)_{1-3}$—CO—OR5 or —$(CH_2)_{1-3}$—CO[NCHR7CO]$_m$ $NH_2$; and n is 1.

11. The compound according to claim 1 which is
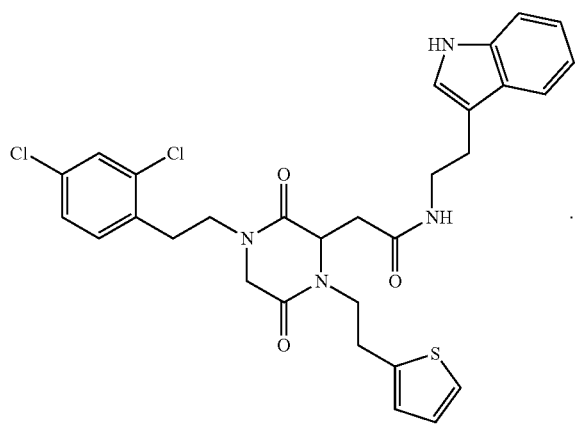 [SMILES: O=C(CC1C(=O)N(CCc2ccc(Cl)cc2Cl)CC(=O)N1CCc1cccs1)NCCc1c[nH]c2ccccc12]
12. The compound according to claim 1 which is
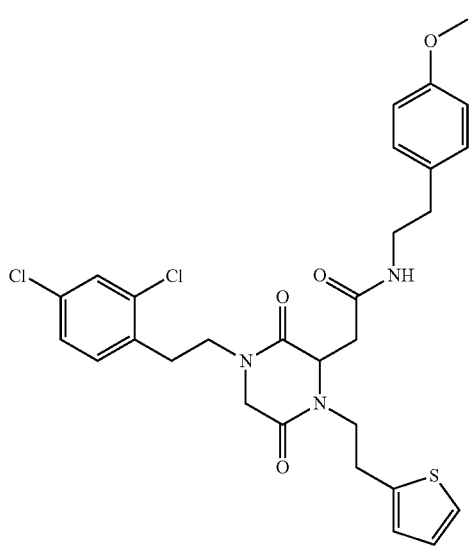
13. The compound according to claim 1 which is selected from the group consisting of:
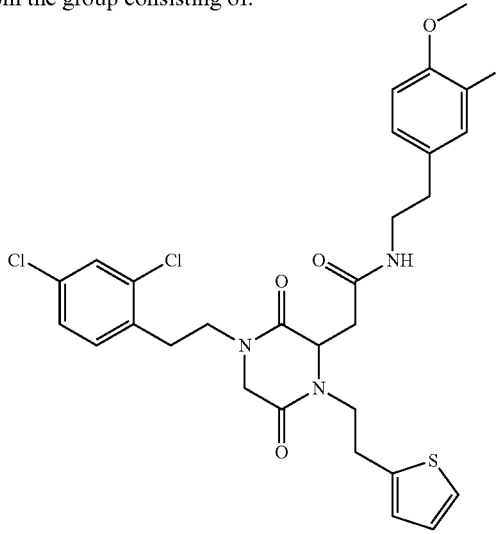
-continued
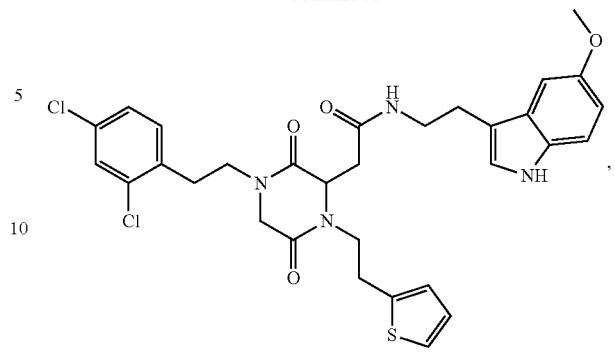
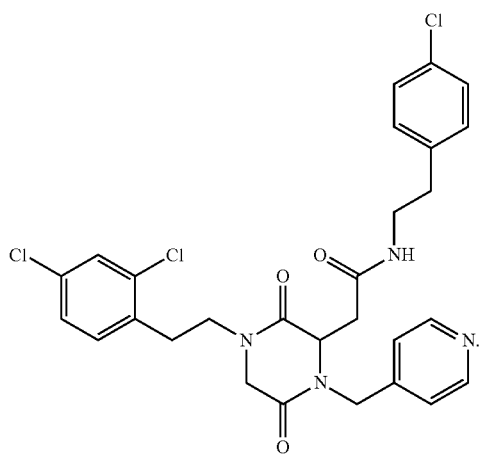
and
* * * * *

UNITED STATES PATENT AND TRADEMARK OFFICE
CERTIFICATE OF CORRECTION

PATENT NO. : 9,040,701 B2  
APPLICATION NO. : 13/387240  
DATED : May 26, 2015  
INVENTOR(S) : Ángel Messeguer Peypoch et al.

Page 1 of 1

It is certified that error appears in the above-identified patent and that said Letters Patent is hereby corrected as shown below:

In the Claims

Column 184, Line 26: change "ORS" to --OR5--

Signed and Sealed this  
Third Day of November, 2015

Michelle K. Lee  
*Director of the United States Patent and Trademark Office*